US009453232B2

(12) United States Patent
Qvit-Raz et al.

(10) Patent No.: US 9,453,232 B2
(45) Date of Patent: *Sep. 27, 2016

(54) TOPICAL COMPOSITION COMPRISING TRANSFORMED BACTERIA EXPRESSING A COMPOUND OF INTEREST

(71) Applicant: TOPGENIX, INC., Menlo Park, CA (US)

(72) Inventors: Noga Qvit-Raz, Menlo Park, CA (US); Tahel Altman, Menlo Park, CA (US)

(73) Assignee: TOPGENIX, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/863,236

(22) Filed: Sep. 23, 2015

(65) Prior Publication Data

US 2016/0000701 A1    Jan. 7, 2016

Related U.S. Application Data

(63) Continuation of application No. 13/961,845, filed on Aug. 7, 2013, now Pat. No. 9,234,204.

(60) Provisional application No. 61/680,620, filed on Aug. 7, 2012, provisional application No. 61/836,594, filed on Jun. 18, 2013.

(51) Int. Cl.

| | |
|---|---|
| *A61K 8/18* | (2006.01) |
| *C12N 15/74* | (2006.01) |
| *A61Q 17/04* | (2006.01) |
| *A61Q 17/00* | (2006.01) |
| *A61K 8/99* | (2006.01) |
| *A61Q 19/00* | (2006.01) |
| *A61Q 19/08* | (2006.01) |
| *A61K 35/744* | (2015.01) |
| *A61K 8/27* | (2006.01) |
| *A61K 8/40* | (2006.01) |
| *C12N 1/20* | (2006.01) |
| *C12P 21/04* | (2006.01) |
| *C12P 21/06* | (2006.01) |

(52) U.S. Cl.
CPC ............... *C12N 15/746* (2013.01); *A61K 8/27* (2013.01); *A61K 8/40* (2013.01); *A61K 8/99* (2013.01); *A61K 35/744* (2013.01); *A61Q 17/00* (2013.01); *A61Q 17/04* (2013.01); *A61Q 19/007* (2013.01); *A61Q 19/08* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,259,444 A | 3/1981 | Chakrabarty | |
| 5,207,998 A * | 5/1993 | Robinson | ............... A61K 8/29 424/47 |
| 5,620,682 A | 4/1997 | Fogel | |
| 6,221,648 B1 | 4/2001 | Le Page et al. | |
| 6,605,286 B2 | 8/2003 | Steidler et al. | |
| 6,787,147 B1 * | 9/2004 | Huner | ................... A61K 8/44 424/400 |
| 7,081,442 B2 | 7/2006 | Seiberg et al. | |
| 2009/0130073 A1 | 5/2009 | Reindl et al. | |
| 2009/0232751 A1 | 9/2009 | Lott et al. | |
| 2012/0263661 A1 | 10/2012 | Grune | |
| 2012/0301452 A1 | 11/2012 | Gueniche et al. | |
| 2012/0308525 A1 | 12/2012 | Greenberg et al. | |
| 2014/0044653 A1 | 2/2014 | Qvit-Raz et al. | |
| 2014/0044677 A1 | 2/2014 | Qvit-Raz et al. | |

FOREIGN PATENT DOCUMENTS

| | | | |
|---|---|---|---|
| EP | 1473028 A1 | 11/2004 | |
| EP | 0975227 B1 | 11/2005 | |
| EP | 1789529 A2 | 2/2006 | |
| EP | 1 322 318 B1 * | 12/2010 | ............. A61K 35/74 |
| EP | 1322318 B1 | 12/2010 | |
| EP | 2364712 B1 | 3/2013 | |
| FR | 2803201 A1 | 7/2001 | |
| WO | WO86/02350 A1 | 4/1986 | |
| WO | WO89/01970 A2 | 3/1989 | |
| WO | WO96/11277 A1 | 4/1996 | |
| WO | WO02/39974 A1 | 5/2002 | |
| WO | WO03/020236 A2 | 3/2003 | |
| WO | WO2006/013441 A2 | 2/2006 | |
| WO | WO2007/039086 A1 | 4/2007 | |
| WO | WO2011/150127 A2 | 12/2011 | |
| WO | WO2011/151426 A2 | 12/2011 | |
| WO | WO2012/150269 A1 | 11/2012 | |
| WO | WO2013/044059 A2 | 3/2013 | |

OTHER PUBLICATIONS

Shick et al., "Mycosporine-Like Amino Acids and Related Gadusols: Biosynthesis, Accumulation, and UV-Protective Functions in Aquatic Organisms" 64 Annual Review of Physiology 223-262 (2002).*
Rastogi et al., "Photoprotective compounds from marine organisms" 37 Journal of Industrial Microbiology and Biotechnology 537-558 (2010).*
Balskus et al., "The Genetic and Molecular Basis for Sunscreen Biosynthesis in Cyanobacteria" 329 Science 1653-1656 (incl Supplemental Material) (2010).*
Perez-Arellano et al., "Construction of Compatible Wide-Host-Range Shuttle Vectors for Lactic Acid Bacteria and *Escherichia coli*" 46 Plasmid 106-116 (2001).*

(Continued)

*Primary Examiner* — Nancy J Leith
(74) *Attorney, Agent, or Firm* — Shay Glenn LLP

(57) ABSTRACT

Compositions comprised of a population of transformed bacteria formulated for topical application to a subject are described. The population of transformed bacteria are created from a non-pathogenic bacteria and transformed to express a compound of interest for a therapeutic or a cosmetic purpose. In one embodiment, the composition is for protection of the skin from ultraviolet rays.

20 Claims, 3 Drawing Sheets

(56) References Cited

OTHER PUBLICATIONS

Aethic; Aethic, King's college london to develop first sunscreen based on mycosporine-like amino acids; 1 page; retrieved from the internet http://www.news-medical.net/news/20120912/Aethic-Kings-College-London-to-develop-first-sunscreen-based-on-mycosporine-like-amino-acids.aspx; Published Sep. 12, 2012.

Balskus et al.; The genetic and molecular basis for sunscreen biosynthesis in cyanobacteria; Science; 329(5999); pp. 1653-1656; Sep. 24, 2010 (with Supporting Online Material).

Boyle; Bacteria could be engineered to produce natural bio-sunscreen; 5 pages; retrieved from the internet http://www.popsci.com/science/article/2010-09/algaes-natural-biosunscreen-could-lead-better-skin-protection; Sep. 9, 2010.

Costello et al.; Bacterial community variation in human body habitats across space and time; Science; 326(5960); pp. 1694-1697; Dec. 18, 2009 (Author Manuscript).

Davison; Risk mitigation of genetically modified bacteria and plants designed for bioremediation; J. Ind. Microbiol. Biotechnol.; 32(11-12); pp. 639-650; Dec. 2005.

Eichenbaum et al.; Use of the lactococcal nisA promoter to regulate gene expression in gram-positive bacteria: comparison of induction level and promoter strenght; Appl. Environ. Microbiol.; 64(8); pp. 2763-2769; Aug. 1998.

Elliot et al.; Defining a bacteriophage T4 late promoter: absence of a "-35" region; Cell; 36(1); pp. 211-219; Jan. 1984.

Fuller; Probiotics in human medicine; Gut; 32(4); pp. 439-442; Apr. 1991.

Gao et al.; Microbial ultraviolet sunscreens; Nat. Rev. Microbiol.; 9(11); pp. 791-802; Oct. 2011.

Gaudu et al.; Respiration capacity and consequences in *lactococcus lactis*; Antonie Van Leeuwenhoek; 82(1-4); pp. 263-269; Aug. 2002.

Gonzalez et al.; Photostability of commercial sunscreens upon sun exposure and irradiation by ultraviolet lamps; BMC Dermatol.; 7:1; 9 pages; Feb. 26, 2007.

Green; Microbial biogeography: from taxonomy to traits; Science; 320(5879); pp. 1039-1043; May 23, 2008.

Grice et al.; Topographical and temporal diversity of the human skin microbiome; Science; 324(5931); pp. 1190-1192; May 29, 2009 (Author Manuscript).

Grice et al.; The skin microbiome; Nat. Rev. Microbiol.; 9(4); pp. 244-253; Apr. 2011 (Author Manuscript).

Gueniche et al.; Bifidobacterium longum lysate, a new ingredient for reactive skin; Exp. Dermatol.; 19(8); pp. e1-e8; Aug. 2010.

Helionori; For a natural bioprotection against UVA, Esocert approved, Patent FR9916785; 4 pages; retrieved Apr. 3, 2009 from the internet http:www.biosiltech.com/sites/default/files/Helionori.pdf.

Hentges; The anaerobic microflora of the human body; Clin.Infect.Dis.; 16(4); pp. S175-S180; 1993 (year of pub. sufficiently earlier than effective US filed and any foreign priority date).

Huang et al.; Industrial production of recombinant therapeutics in *escherichia coli* and its recent advancements; J. Ind. Microbiol. Biotechnol.; 39(3); pp. 383-399; Mar. 2012.

IGEM 2012 Team Minnesota Project: Synthesizing uv-protective compounds in bacteria; 5 pages; retrieved Jul. 24, 2015 from the internet http://2012.igem.org/Team:Minnesota/Protective/UV_Absorption.

Joo et al.; Therapeutic advantages of medicinal herbs fermented with *lactobacillus plantarum*, in topical application and its activities on atopic dermatitis; Phytother. Res.; 23(7); pp. 913-919; Jul. 2009.

Kiatpapan et al.; Genetic manipulation system in propionibacterium; J. Biosci. Bioeng.; 93(1); pp. 1-8; 2002 (year of pub. sufficiently earlier than effective US filing date and any foreign priority date).

Kim et al.; A xylose-inducible *bacillus subtilis* integration vector and its application; Gene; 181(1-2); pp. 71-76; Nov. 28, 1996.

Kim et al.; Improvement of a nisin-inducible expression vector for use in lactic acid bacteria; Plasmid; 58(3); pp. 275-283; Nov. 2007.

Klann et al.; Estrogen-like effects of ultraviolet screen 3-(4-methylbenzlidene)-camphor (Eusolex 6300) on cell proliferation and gene induction in mammalian and amphibian cells; Environ. Res.; 97(3); pp. 274-281; Mar. 2005.

Kleerebezem et al.; Controlled gene expression systems for lactic acid bacteria: transferable nisin-inducible expression cassettes for lactococcus, leuconostoc, and lactobacillus app; Appl. Environ. Microbiol.; 63(11); pp. 4581-4584; Nov. 1997.

Knowland et al.; Sunlight-induced mutagenicity of a common sunscreen ingredient; FEBS Lett.; 324(3); pp. 309-313; Jun. 21, 1993.

Kok et al.; Construction of plasmid cloning vectors for *lactic streptococci* which also replicate in *bacillus subtilis* and *escherichia coli*; Appl. Environ. Microbiol.; 48(4); pp. 726-731; Oct. 1984.

Li et al.; Glutathione protects *lactococcus lactis* against oxidative stress; Appl. Environ. Microbial.; 69(10); pp. 5739-5745; Oct. 2003.

Luchansky et al.; Molecular cloning and deoxyribonucleic acid polymorphisms in *lactobacillus acidophilus* and *lactobacillus gasseri*; J. Dairy Sci..; 74(10); pp. 3293-3302; Oct. 1991.

Mierau et al.; 10 years of the nisin-controlled gene expression system (NICE) in *lactococcus lactis*; Appl. Microbiol. Biotechnol.; 68(6); pp. 705-717; Oct. 2005.

Nguyen et al.; A food-grade system for inducible gene expression in *lactobacillus plantarum* using an alanine racemase-encoding selection marker; J. Agric. Food Chem.; 59(10); pp. 5617-5624; May 25, 2011.

Nouaille et al.; Heterologous protein production and delivery systems for *lactococcus lactis*; Genet. Mol. Res.; 2(1); pp. 102-111; Mar. 31, 2003.

Ouwehand et al.; Probiotics for the skin: a new area of potential application; Lett. Appl. Microbiol.; 36(5); pp. 327-331; 2003 (year of pub. sufficiently earlier than effective US filed and any foreign priority date).

Packaged Facts; The U.S. market for suncare and lipcare products: market report; © 2015; 7 pages; retrieved Jul. 23, 2015 from the internet: http://www.packagedfacts.com/sitemap/product.asp-?productid=222308.

Perez-Arellano et al.; Construction of compatible wide-host-range shuttle vectors for lactic bacteria and *esherichia coli*; Plasmid; 46(2); pp. 106-116; Sep. 2001.

Pouwels et al.; Genetics of lactobacilli: plasmids and gene expression; Antonie Van Leeuwenhoek; 64(2); pp. 85-107; 1993 (year of pub. sufficiently earlier than effective US filed and any foreign priority date).

Rastogi et al.; Photoprotective compounds from marine organisms; J. Ind. Microbiol. Biotechnol.; 37(6); pp. 537-558; Jun. 2010.

Reid et al.; Potential uses of probiotics in clinical practice; Clin. Microbiol. Rev.; 16(4); pp. 658-672; Oct. 2003.

Rolfe; The role of probiotic cultures in the control of gastrointestinal health; J. Nutr.; 130(2S Suppl); pp. 396S-402S; Feb. 2000.

Rud et al.; A synthetic promoter library for constitutive gene expression in *lactobacillus plantarum*; Microbiology; 152(Pt 4); pp. 1011-1019; Apr. 2006.

Russo et al.; Learning how to manipulate dna's double helix has fuelled job growth in biotechnology during the past 50 years; 421(6921); pp. 456-457; Jan. 23, 2003.

Sambandan et al.; Sunscreens: an overview and update; J. Am. Acad. Dermatol.; 64(4); pp. 748-758; Apr. 2011.

Sanchez et al.; General and specialized vectors derived from pBM02, a new rolling circle replicating plasmid of *lactococcus lactis*; Plasmid.; 51(3); pp. 265-271; May 2004.

Shareck et al.; Cloning vectors based on cryptic plasmids isolated from lactic acid bacteria: their characteristics and potential applications in biotechnology; Crit. Rev. Biotechnol.; 24(4); pp. 155-208; 2004 (year of pub. sufficiently earlier than effective US filed and any foreign priority date).

Shick et al.; Mycosporine-like amino acids and related gadusols: biosynthesis, accumulation, and uv-protective functions in aquatic organisms; Ann. Rev. Physiol.; 64; pp. 223-262; 2002 (year of pub. sufficiently earlier than effective US filed and any foreign priority date).

Sorensen; Towards universal systems for recombinant gene expression; Microbial Cell Factories; 9:27; 4 pages; Apr. 2010.

(56) References Cited

OTHER PUBLICATIONS

Steidler et al.; Biological containment of genetically modified *lactococcus lactis* for intestinal delivery of human interleukin 10; Nat. Biotechnol.; 21(7); pp. 785-789; Jul. 2003.
Steidler et al.; Delivery of therapeutic proteins to the mucosa using genetically modified microflora; Expert Opin. Drug Deliv.; 2(4); pp. 737-746; Jul. 2005.
Steidler et al.; Therapeutic drug delivery by genetically modified *lactococcus lactis*; Ann. N Y Acad. Sci.; pp. 176-186; Sep. 3, Aug. 2006.
Stern; Clinical practice. Treatment of photoaging; N. Engl. J. Med.; 350(15); pp. 1526-1534; Apr. 2004.
Storm et al.; On in 3 prescriptions are never redeemed: primary nonadherence in an outpatient clinic; J. Am. Acad. Dermatol.; 59(1); pp. 27-33; Jul. 2008.
Tarras-Wahlberg et al.; Changes in ultraviolet absorption of sunscreens after ultraviolet irradiation; J. Invest. Dermatol.; 113(4); pp. 547-553; Oct. 1999.
Telemet Inc.; Make snow; © 2015; 6 pages; Jul. 23, 2015, retrieved from the internet http://www.telemet.com/snow/snomax.asp.
Torres et al. A new uv-b absorbing mycosporine with photo protective activity from the lichenized ascomycete *collema cristatum*; Eur. J. Biochem.; 271(4); pp. 780-784; Feb. 2004.
Van De Guchte et al.; Heterologous gene expression in *lactococcus lactis* subsp. Lactis: synthesis, secretion, and processing of the *bacillus subtilis* neutral protease; Appl. Environ. Microbiol.; 56(9); pp. 2606-2611; Sep. 1990.
Van Der Vossen et al.; Characterization of transcription initiation and termination signals of the proteinase genes of *lactococcus lactis* Wg2 and enhancement of proteolysis in *L. lactis*; Appl. Environ. Microbiol.; 58(9); pp. 3142-3149; Sep. 1992.
Vangelista et al.; Engineering of *lactobacillus jensenii* to RANTES and a CCR5 antagonist analogue as live HIV-1 blockers; Antimicrob. Agents Chemother.; 54(7); pp. 2994-3001; Jul. 2010.
Wallace et al.; A set of synthetic oligodeoxyribonucleotide primers for DNA sequencing in the plasmid vector pBR322; Gene; 16(1-3); pp. 21-26; Dec. 1981.
Wang et al.; Plasmids in lactobacillus; Crit. Rev. Biotechnol.; 17(3); pp. 227-272; 1997 (year of pub. sufficiently earlier than effective US filed and any foreign priority date).
Weickert et al.; Genetic analysis of the promoter region of the *bacillus subtilis* alpha-amylase gene; J. Bacteril.; 171(7); pp. 3656-3666; Jul. 1989.
Wells et al.; *Lactococcus lactis*: high-level expression of tetanus toxin fragment c and protection against lethal challenge; Mol. Microbiol.; 8(6); pp. 1155-1162; Jun. 1993.
Wells et al.; Mucosal delivery of therapeutic and prophylactic molecules using lactic acid bacteria; Nat. Rev. Microbiol.; 6(5); pp. 349-362; May 2008.
Yagur-Kroll et al.; Strategies for enhancing bioluminescent bacterial sensor performance by promoter region manipulation; Bioeng. Bugs; 1(2); pp. 151-153; Mar.-Apr. 2010.
Zhu et al.; Genetically engineered bacteria expressing alphaMelanocyte stimulating hormone alphaMSH as an inhibitor of traumatic ocular inflammatory reaction in rats; Invest. Opthalmol. Vis. Sci.; 2004; E-abstract-4005; retrieved Nov. 26, 2013 from the internet http://abstracts.iovs.org/cgi/content/abstract/45/5/4005.
Choffnes et al.; Microbial ecology in states of health and disease; Workshop Summary; National Academies Press; Washington (DC); 89 pages; Dec. 29, 2015; retrieved from the Internet (http://www.ncbi.nlm.nih.gov/books/NBK189987/?report+printable).
De La Coba et al.; Prevention of the ultraviolet effects on clinical and histopathological changes, as well as the heat shock protein-70 expression in mouse skin by topical application of algal uv-absorbing compounds; Journal of Dematological Science; 55(3); pp. 161-169; Sep. 30, 2009.
Ebanks et al.; Mechanisms regulating skin pigmentation: the rise and fall of complexion coloration; Int. J. Mol. Sci.; 10(9); pp. 4066-4087; Sep. 15, 2009.

\* cited by examiner

TOPICAL COMPOSITION COMPRISING TRANSFORMED BACTERIA EXPRESSING A COMPOUND OF INTEREST

CROSS-REFERENCE TO RELATED APPLICATIONS

This application is a continuation of U.S. application Ser. No. 13/961,845, filed Aug. 7, 2013, now U.S. Pat. No. 9,234,204, which application claims the benefit of U.S. Provisional Application No. 61/680,620, filed Aug. 7, 2012, and of U.S. Provisional Application No. 61/836,594, filed Jun. 18, 2013, each of which is incorporated herein by reference in its entirety.

REFERENCE TO SEQUENCE LISTING, TABLE OR COMPUTER PROGRAM

A Sequence Listing was submitted electronically via EFS in parent application Ser. No. 13/961,845 in the form of a text file, created Dec. 23, 2013, and named "093242-0016-seqlist_ST25.txt" (88,802 bytes), and is resubmitted herewith.

TECHNICAL FIELD

The subject matter described herein relates to the field of dermatology, and more particularly, to compositions and methods of treatment that comprise transformed bacteria that express a molecule or compound for a topical therapeutic, cosmetic or dermatological purpose.

BACKGROUND

There are a spectrum of dermatological disorders and conditions that are commonly treated with a topically applied agent. In some treatments, the agent offers a therapeutic purpose, for example for treating or ameliorating psoriasis, eczema or dermatitis. In other treatments, the agent offers a cosmetic or protective effect, such as a skin lightening agent or depigmenting agent or a sun protective agent. Topical application of agents for cosmetics and medical purposes has certain limitations. For example, the applied agent can be swept off easily from the skin or the formulation in which the agent is applied can include chemicals that may interfere with the balance of the natural skin microbiota. Creams and ointments can be messy, greasy, cumbersome, and patients can only treat a limited number of lesions on a limited area, and only on certain anatomic sites. As a result, nearly 35% of prescriptions for topical preparations remained behind the pharmacy counter, the patient opting to not pick up the topical prescription. In contrast, prescriptions for systemic agents fared much better, with reports that only 14% went unredeemed (Storm, A. et al., *J. Am. Acad. Dermatol.*, 59:27-33 (2008)).

There are also disadvantages with topical treatments in terms of the patient understanding of how often and how much to apply. In the case of sunscreens, as just one example, people typically apply sunscreens less than half as thickly as and less often than recommended, thus compromising their protection substantially (Stern, R. S., *N Engl J. Med*, 350:1526-1534 (2004)).

There remains a need for more effective topical treatment compositions, for medical, cosmetic and preventative purposes. By way of example, the need for more effective UV protection is recognized around the world, as it is the main cause for the increasing incidence of skin cancers and photoaging. By way of another example, topical treatment of psoriasis and eczema, and other skin disorders, with an effective, long-term therapy is needed.

Healthy human epidermis is colonized by thousands of bacterial species, including bacterial members from mainly five orders harboring about 60% of the total skin microbiome in all people. A healthy human epidermis is colonized with trillions of bacterial cells, creating, on average, approximately $10^8$ bacteria per square centimeter. The skin microflora has evolved into commensal relationship with the host, as they exploit the unique attributes of the skin and keep the skin ecosystem in a healthy balance (Grice A. E., *Science*, 324: 1190-1192 (2009)). A therapy that uses skin bacteria for different dermatological needs would be able to maintain the natural ecosystem of the skin, and also enhance those natural skin bacteria to address specific dermatological needs.

The use of probiotic micro-organisms for improving the skin's immune function under stress conditions, leading to immune suppression, specifically for normalizing the skin's immune activity and reducing the tendency to develop hyper-reactions under such conditions is described in the art, for example in EP Patent No. 1322318. Cosmetic use of probiotic microorganisms as an active agent useful for treating and/or preventing impairing radiance of the skin complexion has also been described (US2012/0301452). Use of solely probiotics, is one approach for topical skin treatments, yet there remains a need for a longer term and/or more potent approach.

Transformed bacteria are being used intensively in modern biotechnology for the production of recombinant proteins and various molecules for food, pharmaceutical, and biocatalysis applications. Bacteria able to produce and secrete proteins encoded by heterologous genes are used extensively for the industrial production of pharmaceutical proteins such as human and animal growth hormones, insulin, interferons, cytokines etc. Organisms other than *E. coli* thus far used or proposed for industrial production include cultured mammalian and insect cells, yeasts and fungi, and various bacteria species, including a number of *Bacillus* spp. Among the bacteria already widely used for industrial purposes are the lactic acid bacteria, which are employed as starter cultures for fermented foodstuffs, and as flavor enhancers, and preservatives. These properties depend on the ability of these organisms to produce certain enzymes, lactic acid and harmless antimicrobial polypeptides, such as nisin (see, for example. U.S. Pat. No. 6,221,648).

The foregoing examples of the related art and limitations related therewith are intended to be illustrative and not exclusive. Other limitations of the related art will become apparent to those of skill in the art upon a reading of the specification and a study of the drawings.

BRIEF SUMMARY

Figure 1A:
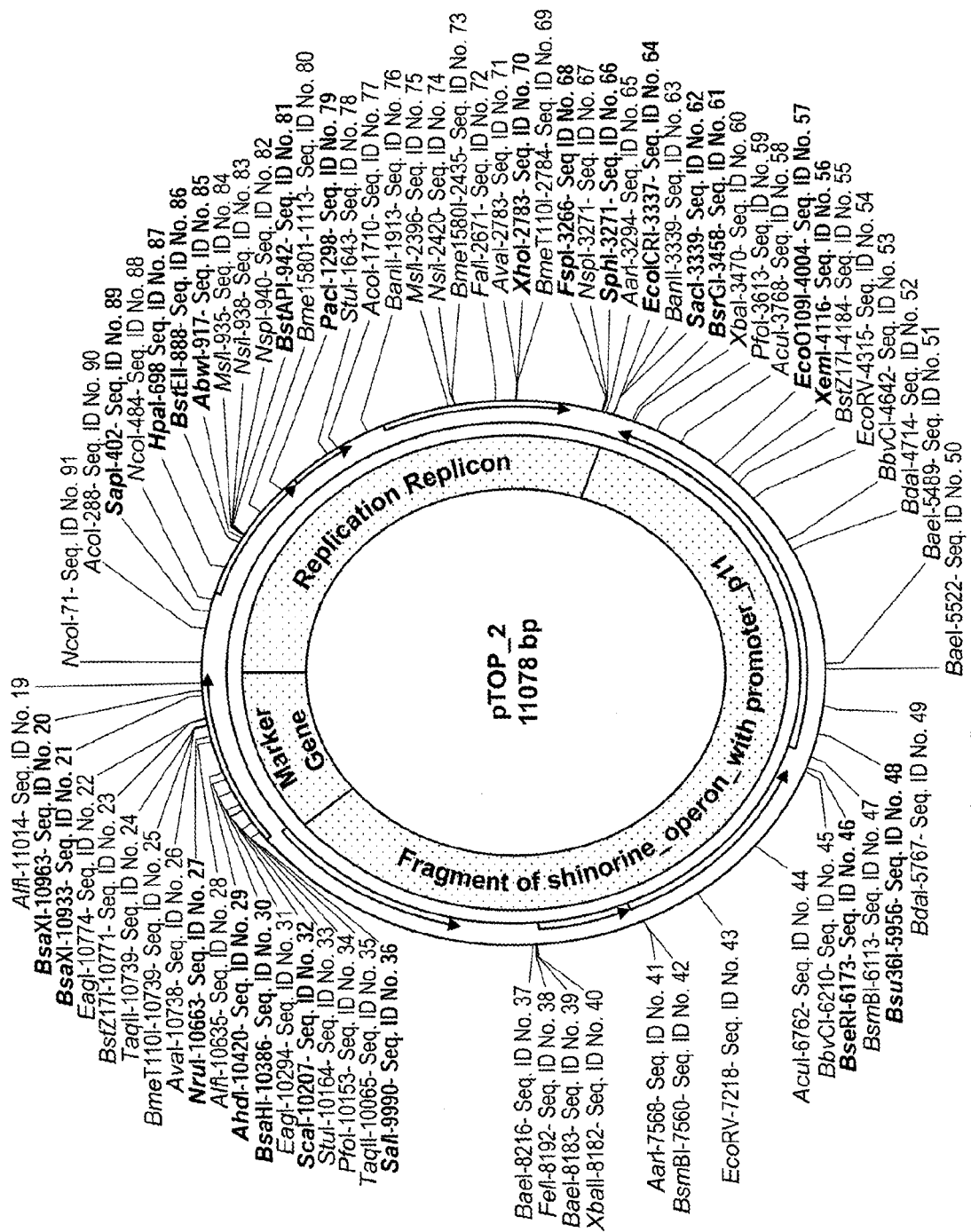
FIGS. 1A-1C are maps of exemplary plasmids or vectors for transforming a bacterium for expression of a compound of interest. Sequences corresponding to the restriction enzyme recognition sites indicated on the map of FIG. 1A are provided below in Table 1 with their respective SEQ ID NOs.

The following aspects and embodiments thereof described and illustrated below are meant to be exemplary and illustrative, not limiting in scope.

In one aspect, a composition comprising a population of transformed bacteria formulated for topical application to a subject is provided, where the population of transformed bacteria is created from a non-pathogenic bacteria transformed to express a compound of interest.

In one embodiment, the population of non-pathogenic bacteria comprises a bacteria that occurs naturally on the human skin; that is, the bacteria in the population are from the human skin microbiome. In another embodiment, the population of non-pathogenic bacteria is a population of live bacteria that express the compound of interest, and in one embodiment, that chronically express the compound of interest. In another embodiment, the population of non-pathogenic bacteria is a population of attenuated bacteria or killed (dead) bacteria, intact or fragments thereof, where the bacteria prior to attenuation or killing expressed the compound of interest.

In one embodiment, the compound of interest is one that can absorb or reflect ultraviolet light. In another embodiment, the compound can absorb or reflect ultraviolet A (320-400 nm), ultraviolet B (315-280 nm), or both.

In yet another embodiment, the compound of interest expressed by the transformed bacteria is selected from the group consisting of: mycosporine, gadusols, oxo-mycosporines, imino-mycosporines and mycosporine-like amino acids (MAAs), scytonemin, melanines, UV-screening/observing amino acids-like molecules, flavonoids, beta-lanines, UV-screening/observing pigments (e.g. carotenoids/cartenoproteins, xanthopylls and porphyrin-based/heme-porphyrin based), UV-screening/observing co-factors (e.g. tetrahydrobiopterin), phenylpropanoids, polyphenol (e.g. tannins), pycnogenol, tyrosinases (and its substrates and products), alpha hydroxy acids (AHAs), polysaccharides (e.g. glycosaminoglycans, (GAGs) or mucopolysaccharides), skin related cofactors, vitamin E, polymers, and additional skin related natural compounds, such as: collagen, keratin, elastin, linoleic acid, laminin, tretinoin, tazarotene, sargaquinoic acid, sargachromenol, fucoxanthin, retinoid, anti-inflammatory cytokines (as Il-2), cortisone, tacrolimus, ciclosporin, resveratrol, gallocatechol, gallocatechin, epigallocatechin gallate, retinoid, vitamin A, vitamin A derivatives, beta-carotene, vitamin D, vitamin A derivatives, moisture compounds; cortisone, tacrolimus and ciclosporin, DNA repair enzymes; photolyase, endonuclease and glycosylase.

In yet another embodiment, the population of transformed bacteria is formulated into the composition to provide at least about $10^2$ bacteria per $cm^2$, or at least about $10^3$, $10^4$, $10^5$, or $10^6$ bacteria per $cm^2$.

In another embodiment, the composition comprises a second population of transformed bacteria formulated for topical application to a subject, wherein the second population of transformed bacteria is either or both (i) created from a non-pathogenic bacteria that is different from the first population of transformed bacteria in the composition or (ii) transformed to express a compound of interest that is different from the first compound of interest expressed by the first population of transformed bacteria in the composition. In other embodiments, the composition comprises at least one population of transformed bacteria, at least two populations of transformed bacteria, or two or more populations of transformed bacteria.

In one embodiment, the second population of non-pathogenic bacteria is from the human skin microbiome. In another embodiment, the second population of non-pathogenic bacteria is a population of live bacteria that express the compound of interest, and in one embodiment, chronically express the compound of interest. In another embodiment, the second population of non-pathogenic bacteria is a population of attenuated bacteria or killed (dead) bacteria, intact or fragments thereof, where the bacteria prior to attenuation or killing expressed the compound of interest.

In still another embodiment, the compound of interest is one for treating psoriasis. Exemplary compounds include, but are not limited to, a compound selected from the group consisting of retinoid, vitamin A, beta-carotene, vitamin D, anti-inflammatory cytokines.

In one embodiment, the compound of interest is an anti-oxidant.

In yet another embodiment, the compound is selected from the group consisting of resveratrol, vitamin E, vitamin C, -epigallocatechin-3-gallate, and retinyl palmitate (retinoids), lutein, tamarind, flavonoids, pycnogenol, lycopene.

In another embodiment, the compound of interest provides a cosmetic effect. For example, the compound may be selected from the group consisting of coenzyme Q10, tyrosinases, collagen, laminin, ceramids, linoleic acid, tretinoin, tazarotene and collagen. In still another embodiment, the cosmetic effect is anti-aging.

In still another embodiment, the compound of interest is one that treats eczema. Exemplary compounds of interest include a compound is selected from the group consisting of cortisone, tacrolimus and ciclosporin.

In other embodiments, the composition comprising the population of transformed bacterial is formulated for topical application to the face. In another embodiment, the composition is formulation for topical application to the skin, excluding mucosal surfaces of the human body.

In another embodiment, the population of transformed bacteria is created from a population of non-pathogenic bacteria resident on the skin in humans. That is, the population of non-pathogenic bacteria comprise a bacteria typically resident on skin in healthy, non-diseased human beings.

The population of transformed bacteria is created, in some embodiments, from nonpathogenic bacterial members selected from those in the group consisting of Actinomycetales, *Anaerococcus*, Bacillales, *Bifidobacterium, Enhydrobacter, Finegoldia, Carnobacterium, Coryneobacterium, Lactobacillus, Lactococcus, Leunconostoc, Macrooccus, Micrococcineae, Oenococcus, Pediococcus, Peptoniphilus, Propionibacterium, Salinicoccus, Sphingomonas, Strepococcus, Tetragenoccus,* and *Weissella*.

In other embodiments, the transformed bacteria in the population of transformed bacterial are not *Propionibacterium acnes*, a pathogenic strain of *Coryneobacterium, S. aureus*, or *S. epidermidis*.

In still another embodiment, the population of transformed bacteria is created from a bacteria selected from those in the group consisting of *Lactobacillus casei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii*, and *Propionibacterium jensenii*.

In yet another embodiment, the population of transformed bacteria is created from a bacteria selected from those in a phylum selected from the group consisting of gamma-proteobacteria, alpha-proteobacteria, and bacteriodetes.

The topical composition that comprises the population of transformed bacteria can be, in various embodiments, a cream, lotion, emulsion, gel, ointment, liquid or spray. In one embodiment, the topical composition is formulated to provide at least about $10^2$ bacteria per $cm^2$.

In another aspect, a method of treatment is provided, wherein a composition as described herein is topically applied to the skin of a subject, preferably a human subject, for disease preventative, or for a therapeutic or cosmetic purpose. In embodiment, topically applying excludes topically applying to a mucosal surface (nasal, vaginal, rectal, oral surfaces) of a human body.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

As used in this specification, the singular forms "a," "an," and "the" include plural referents unless the context clearly dictates otherwise. Thus, for example, reference to an "excipient" includes a single excipient as well as two or more of the same or different excipients.

"Amphiphilic" refers to a molecule combining hydrophilic and lipophilic (hydrophobic) properties.

"Diluents" may be included in the formulations to dissolve, disperse or otherwise incorporate another component in the formulation. Examples of diluents include, but are not limited to, water, buffered aqueous solutions, organic hydrophilic diluents, such as monovalent alcohols, and low molecular weight glycols and polyols (e.g. propylene glycol, polypropylene glycol, glycerol, butylene glycol).

A "gel" is a colloid in which the dispersed phase has combined with the continuous phase to produce a semisolid material, such as jelly.

"Hydrophilic" as used herein refers to substances that have strongly polar groups that readily interact with water.

"Hydrophobic" as used herein refers to substances that lack an affinity for water; tending to repel and not absorb water as well as not dissolve in or mix with water.

"Lipid soluble" as used herein refers to substances that have a solubility of greater than or equal to 5 g/100 mL in a hydrophobic liquid, such as castor oil.

"Lipophilic" refers to compounds having an affinity for lipids. Examples of lipophilic substances include but are not limited to naturally occurring and synthetic oils, fats, fatty acids, lecithins, triglycerides and combinations thereof.

An "oil" is a composition containing at least 95% wt of a lipophilic substance.

"Skin" intends to denote all of the epidermis of an individual, in particular a human being, and in some embodiments to intend, where specified, particular regions of the skin, such as the face, neck, arms, legs, abdomen, hands, back, buttocks, or feet.

"Water soluble" as used herein refers to substances that have a solubility of greater than or equal to 5 g/100 mL water.

II. Topical Composition

The composition described herein is comprised of a population of transformed bacteria formulated for topical application to a subject. Described in section A below are exemplary non-pathogenic bacteria suitable for creating the population of transformed bacteria. In section B, compounds of interest to be expressed by the population of transformed bacteria are described, and in section C techniques for creating the transformed bacterial population are set forth. In section D, topical compositions comprising the population of transformed bacteria are disclosed.

A. Exemplary Bacteria

The population of bacteria in the compositions described herein and for use in the described methods is created from a non-pathogenic bacterium that has been genetically modified to express, produce and/or secrete a compound of interest. In this section, exemplary non-pathogenic bacteria are described. In one embodiment, the bacteria in the population are non-pathogenic and non-invasive microorganisms, and can be in certain embodiments a gram-positive food grade bacterial strain. In another embodiment, the populations of transformed bacteria are prepared from a bacterium that occurs naturally in the skin microbiome.

Human skin is populated with microorganisms that reside on the skin, referred to as the skin microbiome. The bacterial microorganisms resident on the skin (in a healthy (non-diseased) human) are usually non-pathogenic and commensal (not harmful to the host) and/or mutualistic (offer a benefit). The bacteria commonly resident on the human skin are set forth in below, and are indicated by phylogenetic levels, described with their phylogenetic lineage, down to the genus level (Grice, E. A. et al., Science, 324(5931): 11904192 (2009); Costello, E. K., et al. Science, 326(5960): 1694-1697 (2009), Grice E. A. and J. A. Segre, Nature Reviews Microbiology, 9:244-253 (2011)).

The bacteria forming the population of bacteria in the composition, and that are transformed to express one or more compounds of interest, can be a collection of the same bacteria or a mixture of different bacteria, at different phylogenetic levels. In one embodiment, the populations of bacteria for transformation are a group of individuals of one bacterial species in an area that is separate from other groups of bacteria, apart from rare migration events. In practice, the size and nature of the area (e.g., size and location of area on skin, such as chin, forehead) is defined, often arbitrarily, for a desired purpose. In another embodiment, the bacteria for transformation to prepare the composition are a community of bacteria, intending a collection of populations of different bacteria species that occur together in space and time. In one embodiment, the community of bacteria includes all species (that is, across all trophic levels and/or phylogenetic levels), or, alternatively, includes all trophically similar species (for example, all the plants in a rainforest). In another embodiment, the bacteria for transformation to prepare the composition are a metapopulation, intending a group of populations that are perceived to exist as a series of local populations that are linked by migration between them. In another embodiment, the bacteria for transformation to prepare the composition are a metacommunity, intending an assemblage of trophically similar individuals and species, each of which is perceived to exist as a series of local communities, linked by the dispersal of potentially interacting species (Green, J. L. et al., *Science,* 320(5879):1039-43 (2008)).

Bacteria resident on the skin of healthy humans include bacterial species typically resident on the face of humans, such as Actinobacteria, including bacterial in the genus *corynebacterium* and in the genus *propionibacterium*. In other embodiments, bacteria resident on the skin of healthy human subjects include bacterial species typically resident on skin other than the face, including for example bacteria in the genus *bacteroidetes* and *proteobacteria*. Other bacteria in the skin microbiome include those listed herein below.

In one embodiment, the bacteria are from the genus *Propionibacterium*, including but not limited to, *Propionibacterium acidifaciens, Propionibacterium acidipropionici, Propionibacterium acidipropionici* strain 4900, *Propionibacterium acnes, Propionibacterium australiense, Propionibacterium avidum, Propionibacterium cyclohexanicum, Propionibacterium freudenreichii* subsp. *Freudenreichii, P. freudenreichii* ssp. *freudenreichii* strain 20271, *Propionibacterium freudenreichii* subsp. *Shermanii, P. freudenreichii* ssp. *shermanii* strain 4902, *P. freudenreichii* ssp. *shermanii* strain 4902, *Propionibacterium granulosum, Propionibacterium innocuum, jensenii, P. jensenii* strain 20278, *Propionibacterium lymphophilum, Propionibacterium microaerophilum, Propionibacterium propionicum, Propionibacterium thoenii*, and *P. thoenii* strain 20277.

In another embodiment, the bacteria are a population of bacteria classified as "generally regarded as safe" (GRAS) in the *Propionibacterium* genus, including but not limited to *Propionibacterium acidipropionici, Propionibacterium freudenreichii* subsp. *Freudenreichii, Propionibacterium freudenreichii* subsp. *shermanii, Propionibacterium jensenii*, and *Propionibacterium thoenii*. In one embodiment, the bacteria is not *Propionibacterium acnes*.

In one embodiment, the bacteria are from the genus *Corynebacterium*, including but not limited to, *C. accolens, C. afermentan, C. amycolatum, C. argentoratense, C. aquaticum, C. auris, C. bovis, C. diphtheria, C. equi* (now *Rhodococcus equi*), *C. flavescens, C. glucuronolyticum, C. glutamicum, C. granulosum, C. haemolyticum, C. halofytica, C. jeikeium* (group JK), *C. macginleyi, C. matruchotii, C. minutissimum, C. parvum* (*Propionibacterium acnes*), *C. propinquum, C. pseudodiphtheriticum* (*C. hofmannii*), *C. pseudotuberculosis*, (*C. ovis*), *C. pyogenes, C. urealyticum* (group D2), *C. renale, C. spec, C. striatum, C. tenuis, C. ulcerans, C. urealyticum*, and *C. xerosis*. Bacterial with lipophilic and nonlipophilic groups are contemplated, and the nonlipophilic bacteria may include fermentative corynebacteria and nonfermentative corynebacteria.

In another embodiment, the bacteria are a population of bacteria classified as "generally regarded as safe" (GRAS) in the *Corynebacterium* genus, including but not limited to *Corynebacterium ammoniagenes, Corynebacterium casei, Corynebacterium flavescens*, and *Corynebacterium variabile*.

In one embodiment, the bacteria is not *C. diphtheria C. amicolatum, C. striatum, C. jeikeium, C. urealyticum*, and *C. xerosis, C. pseudotuberculosis, C. tenuis, C. striatum*, or *C. minutissimum*, as these may be pathogenic.

In one embodiment, the bacteria are from the suborder Micrococcineae, including but not limited to the GRAS bacteria species *Arthrobacter arilaitensis, Arthrobacter bergerei, Arthrobacter globiformis, Arthrobacter nicotianae, Kocuria rhizophila, Kocuria varians, Micrococcus luteus, Micrococcus lylae, Microbacterium gubbeenense, Brevibacterium aurantiacum, Brevibacterium casei, Brevibacterium linens, Brachybacterium alimentarium*, and *Brachybacterium tyrofermentans*.

In one embodiment, the bacteria are from the order Actinomycetales, including but not limited to the GRAS bacteria species *Streptomyces griseus* subsp. *Griseus*. In one embodiment, the bacteria *Streptomyces griseus* will not express tyrosinase.

In another embodiment, the bacteria are from the genus *Staphylococcus*, including but not limited to, *Staphylococcus agnetis, S. arlettae, S. auricularis, S. capitis, S. caprae, S. camosus, Staphylococcus caseolyticus, S. chromogenes, S. cohnii, S. condiment, S. delphini, S. devriesei, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostra, S. saccharolyticus, S. saprophyticus, S. schleiferi, S. sciuri, S. simiae, S. simulans, S. stepanovicii, S. succinus, S. vitulinus, S. wameri*, and *S. xylosus*.

In another embodiment, the bacteria are a population of bacteria classified as "generally regarded as safe" (GRAS) in the order of *Staphylococcus*, including but not limited to, *Staphylococcus camosus* subsp. *Camosus, Staphylococcus camosus* subsp. *Utilis, Staphylococcus cohnii, Staphylococcus condimenti, Staphylococcus equorum* subsp. *Equorum, Staphylococcus equorum* subsp. *Linens, Staphylococcus fleurettii, Staphylococcus piscifermentans, Staphylococcus saprophyticus, Staphylocrus sduri* subsp. *Sduri, Staphylococcus succinus* subsp *succinus, Staphylococcus succinus* subsp. *Casei, Staphylococcus vitulinus, Staphylococcus wameri*, and *Staphylocrus xylosus*.

In one embodiment, the bacteria is not *S. aureus* or *S. epidermidis*.

In another embodiment, the bacteria are from the genus *Streptococcus*, including but not limited to, *Streptococcus acidominimus, Streptococcus adjacens, Streptococcus agalactiae, Streptococcus alactolyticus, Streptococcus anginosus, Streptococcus australis, Streptococcus bovis, Streptococcus caballi, Streptococcus canis, Streptococcus caprinus, Streptococcus castoreus, Streptococcus cecorum, Streptococcus constellatus, Streptococcus constellatus* subsp. *Constellatus, Streptococcus constellatus* subsp. *Pharyngis, Streptococcus cremoris, Streptococcus criceti, Streptococcus cristatus, Streptococcus danieliae, Streptococcus defectives, Streptococcus dentapri, Streptococcus dentirousetti, Streptococcus didelphic, Streptococcus difficilis, Streptococcus durans, Streptococcus dysgalactiae, Streptococcus dysgalactiae* subsp. *Dysgalactiae, Streptococcus dysgalactiae* subsp. *Equisimilis, Streptococcus entericus, Streptococcus equi, Streptococcus equi* subsp. *Equi, Streptococcus equi* subsp. *Ruminatorum, Streptococcus equi* subsp. *Zooepi-* demicus, Streptococcus equines, Streptococcus faecalis, Streptococcus faecium, Streptococcus ferus, Streptococcus gallinaceus, Streptococcus gallolyticus, Streptococcus gallolyticus subsp. Gallolyticus, Streptococcus gallolyticus subsp. Macedonicus, Streptococcus gallolyticus subsp. Pasteurianus, Streptococcus garvieae, Streptococcus gordonii, Streptococcus halichoeri, Streptococcus hansenii, Streptococcus henryi, Streptococcus hyointestinalis, Streptococcus hyovaginalis, Streptococcus ictaluri, Streptococcus infantarius, Streptococcus infantarius subsp. Coli, Streptococcus infantarius subsp. Infantarius, Streptococcus infantis, Streptococcus iniae, Streptococcus intermedius, Streptococcus intestinalis, Streptococcus lactarius, Streptococcus lactis, Streptococcus lactis subsp. Cremoris, Streptococcus lactis subsp. Diacetilactis, Streptococcus lactis subsp. Lactis, Streptococcus lutetiensis, Streptococcus macacae, Streptococcus macedonicus, Streptococcus marimammalium, Streptococcus massiliensis, Streptococcus merionis, Streptococcus minor, Streptococcus mitis, Streptococcus morbillorum, Streptococcus mutans, Streptococcus oligofermentans, Streptococcus oxalis, Streptococcus orisratti, Streptococcus ovis, Streptococcus parasanguinis, Streptococcus parauberis, Streptococcus parvulus, Streptococcus pasteurianus, Streptococcus peroris, Streptococcus phocae, Streptococcus plantarum, Streptococcus pleomorphus, Streptococcus pluranimalium, Streptococcus plurextorum, Streptococcus pneumonia, Streptococcus porci, Streptococcus porcinus, Streptococcus porcorum, Streptococcus pseudopneumoniae, Streptococcus pseudoporcinus, Streptococcus pyogenes, Streptococcus raffinolactis, Streptococcus ratti, Streptococcus rupicaprae, Streptococcus saccharolyticus, Streptococcus salivarius, Streptococcus salivarius subsp. Salivarius, Streptococcus salivarius subsp. Thermophilus, Streptococcus sanguinis, Streptococcus shiloi, Streptococcus sinensis, Streptococcus sobrinus, Streptococcus suis, Streptococcus thermophilus, Streptococcus thoraltensis, Streptococcus tigurinus, Streptococcus troglodytae, Streptococcus troglodytidis, Streptococcus uberis, Streptococcus urinalis, Streptococcus vestibularis, and Streptococcus waius.

In another embodiment, the bacteria are a population of bacteria classified as "generally regarded as safe" (GRAS) in the genus *Streptococcus*, including but not limited to, *Streptococcus thermophilus* strain Th4, *Streptococcus gallolyticus* subsp. *Macedonicus*, *Streptococcus salivarius* subsp. *Salivarius*, and *Streptococcus salivarius* subsp. *Thermophilus*.

In another embodiment, the bacteria are from the genus *Lactobacillus*, including but not limited to, *Lactococcus garvieae, Lactococcus lactis, Lactococcus lactis* subsp. *cremoris, Lactococcus lactis* subsp. *hordniae, Lactococcus lactis, Lactococcus lactis* subsp. *Lactis, Lactococcus piscium, Lactococcus plantarum, Lactococcus raffinolactis, Lactobacillus acetotolerans, Lactobacillus acidophilus, Lactobacillus agilis, Lactobacillus algidus, Lactobacillus alimentarius, Lactobacillus amylolyticus, Lactobacillus amylophilus, Lactobacillus amylovorus, Lactobacillus animalis, Lactobacillus aviarius, Lactobacillus aviarius* subsp. *araffinosus, Lactobacillus aviarius* subsp. *aviarius, Lactobacillus bavaricus, Lactobacillus bifermentans, Lactobacillus brevis, Lactobacillus buchneri, Lactobacillus bulgaricus, Lactobacillus camis, Lactobacillus casei, Lactobacillus casei* subsp. *alactosus, Lactobacillus casei* subsp. *casei, Lactobacillus casei* subsp. *pseudoplantarum, Lactobacillus casei* subsp. *rhamnosus, Lactobacillus casei* subsp. *tolerans, Lactobacillus catenaformis, Lactobacillus cellobiosus, Lactobacillus collinoides, Lactobacillus confusus, Lactobacillus coryniformis, Lactobacillus coryniformis* subsp. *coryniformis, Lactobacillus coryniformis* subsp. *torquens, Lactobacillus crispatus, Lactobacillus curvatus, Lactobacillus curvatus* subsp. *curvatus, Lactobacillus curvatus* subsp. *melibiosus, Lactobacillus delbrueckii, Lactobacillus delbrueckii* subsp. *bulgaricus, Lactobacillus delbrueckii* subsp. *delbrueckii, Lactobacillus delbrueckii* subsp. *lactis, Lactobacillus divergens, Lactobacillus farciminis, Lactobacillus fermentum, Lactobacillus formicalis, Lactobacillus fructivorans, Lactobacillus fructosus, Lactobacillus gallinarum, Lactobacillus gasseri, Lactobacillus graminis, Lactobacillus halotolerans, Lactobacillus hamsteri, Lactobacillus helveticus, Lactobacillus heterohiochii, Lactobacillus hilgardii, Lactobacillus homohiochii, Lactobacillus iners, Lactobacillus intestinalis, Lactobacillus jensenii, Lactobacillus johnsonii, Lactobacillus kandleri, Lactobacillus kefiri, Lactobacillus kefuranofaciens, Lactobacillus kefirgranum, Lactobacillus kunkeei, Lactobacillus lactis, Lactobacillus leichmannii, Lactobacillus lindneri, Lactobacillus malefermentans, Lactobacillus mali, Lactobacillus maltaromicus, Lactobacillus manihotivorans, Lactobacillus minor, Lactobacillus minutus, Lactobacillus mucosae, Lactobacillus murinus, Lactobacillus nagelii, Lactobacillus oris, Lactobacillus panis, Lactobacillus parabuchneri, Lactobacillus paracasei, Lactobacillus paracasei* subsp. *paracasei, Lactobacillus paracasei* subsp. *tolerans, Lactobacillus parakefiri, Lactobacillus paralimentarius, Lactobacillus paraplantarum, Lactobacillus pentosus, Lactobacillus perolens, Lactobacillus piscicola, Lactobacillus plantarum, Lactobacillus pontis, Lactobacillus reuteri, Lactobacillus rhamnosus, Lactobacillus rhamnosus* strain 5 Æ 5a, *Lactobacillus rimae, Lactobacillus rogosae, Lactobacillus ruminis, Lactobacillus sakei, Lactobacillus sakei* subsp. *camosus, Lactobacillus sakei* subsp. *sakei, Lactobacillus salivarius, Lactobacillus salivarius* subsp. *salicinius, Lactobacillus salivarius* subsp. *salivarius, Lactobacillus sanfranciscensis, Lactobacillus sharpeae, Lactobacillus suebicus, Lactobacillus trichodes, Lactobacillus uli, Lactobacillus vaccinostercus, Lactobacillus vaginalis, Lactobacillus viridescens, Lactobacillus vitulinus, Lactobacillus xylosus, Lactobacillus yamanashiensis, Lactobacillus yamanashiensis* subsp. *mali, Lactobacillus yamanashiensis* subsp. *Yamanashiensis* and *Lactobacillus zeae*.

In another embodiment, the bacteria are a population of bacteria classified as "generally regarded as safe" (GRAS) in the genus *Lactobacillus*, including but not limited to, *Lactobacillus acidophilus* strain NP 28, *Lactobacillus acidophilus* strain NP51, *Lactobacillus* subsp. *lactis* strain NP7, *Lactobacillus reuteri* strain NCIMB 30242, *Lactobacillus casei* strain Shirota, *Lactobacillus reuteri* strain DSM 17938, *Lactobacillus reuteri* strain NCIMB 30242, *Lactobacillus acidophilus* NCFM, *Lactobacillus rhamnosus* strain HN001, *Lactobacillus rhamnosus* strain HN001 produced in a milk-based medium, *Lactobacillus reuteri* strain DSM 17938, *Lactobacillus casei* subsp. *rhamnosus* strain GG, *Lactobacillus acidophilus, Lactobacillus lactis, Lactobacillus acetotolerans, Lactobacillus acidifarinae, Lactobacillus acidipisds, Lactobacillus acidophilus, Lactobacillus alimenmrius, Lactobacillus amylolyticus, Lactobacillus amylovorus, Lactobacillus brevis, Lactobacillus buchneri, Lactobacillus cacaonum, Lactobacillus casei* subsp. *Casei, Lactobacillus collinoides, Lactobacillus composti, Lactobacillus coryniformis* subsp. *Coryniformis, Lactobacillus crispatus, Lactobacillus crustorum, Lactobacillus curvatus* subps. *Curvatus, Lactobacillus delbrueckii* subsp. *Bulgaricus, Lactobacillus delbrueckii* subsp. *Delbrueckii, Lactobacillus delbrueckii* subsp. *Lactis, Lactobacillus dextrinicus*,

*Lactobacillus dioliivorans, Lactobacillus fabifermentans, Lactobacillus farciminis, Lactobacillus fermentum, Lactobacillus fructivorans, Lactobacillus frumenti, Lactobacillus gasseri, Lactobacillus ghanensis, Lactobacillus hammesii, Lactobacillus harbinensis, Lactobacillus helveticus, Lactobacillus hilgardii, Lactobacillus homohiochii, Lactobacillus hordei, Lactobacillus jensenii, Lactobacillus johnsonii, Lactobacillus kefiri, Lactobacillus kefiranofadens* subsp. *Kefiranofaciens, Lactobacillus kefiranofadens* subsp. *Kefirgranum, Lactobacillus kimchii, Lactobacillus kisonensis, Lactobacillus mali, Lactobacillus manihotivorans, Lactobacillus mindensis, Lactobacillus mucosae, Lactobacillus nagelii, Lactobacillus namurensis, Lactobacillus nantensis, Lactobacillus nodensis, Lactobacillus oeni, Lactobacillus otakiensis, Lactobacillus panis, Lactobacillus parabrevis, Lactobacillus parabuchneri, Lactobacillus paracasei* subsp. *Paracasei, Lactobacillus parakefiri, Lactobacillus paralimentarius, Lactobacillus paraplantarum, Lactobacillus pentosus, Lactobacillus perolens, Lactobacillus plantarum* subsp. *Plantarum, Lactobacillus pobuzihii, Lactobacillus ponds, Lactobacillus rapi, Lactobacillus reuteri, Lactobacillus rhamnosus, Lactobacillus rossiae, Lactobacillus sakei* subsp *carnosus, Lactobacillus sakei* subsp. *Sakei, Lactobacillus sali varius* subsp. *Salivarius, Lactobacillus sanfranciscensis, Lactobacillus satsumensis, Lactobacillus secaliphilus, Lactobacillus senmaizukei, Lactobacillus siliginis, Lactobacillus spicheri, Lactobacillus suebicus, Lactobacillus sunkii, Lactobacillus tucceti, Lactobacillus vacdnosterrus, Lactobacillus versmoldensis,* and *Lactobacillus yamanashiensis.*

In another embodiment, the bacteria are from the genus *Lactococcus*, including but not limited to, *Lactococcus Schleifer, Lactococcus chungangensis, Lactococcus fujiensis, Lactococcus garvieae, Lactococcus lactis, Lactococcus lactis* subsp. *Cremoris, Lactococcus lactis* subsp. *Hordniae, Lactococcus lactis* subsp. *Lactis, Lactococcus lactis* subsp. *Tructae, Lactococcus piscium, Lactococcus plantarum,* and *Lactococcus raffinolacti.*

In another embodiment, the bacteria are a population of bacteria classified as "generally regarded as safe" (GRAS) in the genus *Lactococcus*, including but not limited to, *Lactococcus lactis* subsp. *Cremoris, Lactococcus lactis* subsp. *lactis,* and *Lactococcus raffinolactis.*

In another embodiment, the bacteria are from the genus *Enterococcus*, including but not limited to, the GRAS bacteria species *Enterococcus durans, Enterococcus faecalis,* and *Enterococcus faecium.*

In another embodiment, the bacteria are from the genus *Tetragenococcus*, including but not limited to, *Tetragenococcus halophilus* and *Tetragenococcus koreensis.*

In another embodiment, the bacteria are from the genus *Weissella*, including but not limited to, the GRAS bacteria species *Weissella koreensis, Weissella paramesenteroides, Weissella thailandensis, Weissella confusa, Weissella beninensis, Weissella cibaria, Weissella fabaria, Weissella ghanensis,* and *Weissella hellenica.*

In another embodiment, the bacteria are from the genus *Leuconostoc*, including but not limited to, the GRAS bacteria species *Leuconostoc carnosum, Leuconostoc citreum, Leuconostoc fallax, Leuconostoc holzapfelii, Leuconostoc inhae, Leuconostoc kimchii, Leuconostoc lactis, Leuconostoc mesenteroides* subsp. *Cremoris, Leuconostoc mesenteroides* subsp. *Dextranicum, Leuconostoc mesenteroides* subsp. *Mesenteroides, Leuconostoc palmae,* and *Leuconostoc pseudomesenteroides.*

In another embodiment, the bacteria are from the genus *Oenococcus*, including but not limited to, *Oenococcus oeni.*

In another embodiment, the bacteria are from the genus *Salinicoccus*, including but not limited to, *Salinicoccus Ventosa, Salinicoccus albus, Salinicoccus alkaliphilus, Salinicoccus carnicancri, Salinicoccus halodurans, Salinicoccus hispanicus, Salinicoccus iranensis, Salinicoccus jeotgali, Salinicoccus kunmingensis, Salinicoccus luteus, Salinicoccus qingdaonensis, Salinicoccus roseus, Salinicoccus salsiraiae, Salinicoccus sesuvii,* and *Salinicoccus siamensis.*

In another embodiment, the bacteria are from the genus of *Macrococcus*, including but not limited to, *Macrococcus caseolyticus.*

In another embodiment, the bacteria are from the order Bacillales, including but not limited to, the GRAS bacteria species *Bacillus amyloliquefaciens, Bacillus coagulans,* and *Bacillus subbtilis.*

In another embodiment, the bacteria in the population are not *Finegoldia magna.*

In another embodiment, the bacteria are from the genus of *Anaerococcus*, including but not limited to, the species *Anaerococcus hydrogenalis, Anaerococcus lactolyticus, Anaerococcus murdochii, Anaerococcus octavius, Anaerococcus prevotii, Anaerococcus tetradius,* and *Anaerococcus vaginalis.*

In another embodiment, the bacteria are from the genus of *Peptoniphilus*, including but not limited to, the species *Peptoniphilus asaccharolyticus, Peptoniphilus coxii, Peptoniphilus duerdenii, Peptoniphilus gorbachii, Peptoniphilus harei, Peptoniphilus indolicus, Peptoniphilus ivorii, Peptoniphilus koenoeneniae, Peptoniphilus lacrimalis, Peptoniphilus methioninivorax, Peptoniphilus olsenii,* and *Peptoniphilus tyrrelliae.*

In another embodiment, the bacteria are from the genus of *Enhydrobacter*, including but not limited to, the species *Enhydrobacter aerosaccus.*

In another embodiment, the bacteria are from the genus of *Sphingomonas*, including but not limited to, the species *Sphingomonas abaci, Sphingomonas adhaesiva, Sphingomonas aerolata, Sphingomonas aestuarii, Sphingomonas alaskensis, Sphingomonas alpine, Sphingomonas aquatilis, Sphingomonas aromaticivorans, Sphingomonas asaccharolytica, Sphingomonas astaxanthinifaciens, Sphingomonas aurantiaca, Sphingomonas azotifigens, Sphingomonas capsulate, Sphingomonas changbaiensis, Sphingomonas chlorophenolica, Sphingomonas chungbukensis, Sphingomonas cloacae, Sphingomonas cynarae, Sphingomonas desiccabilis, Sphingomonas dokdonensis, Sphingomonas echinoides, Sphingomonas endophytica, Sphingomonas faeni, Sphingomonas fennica, Sphingomonas formosensis, Sphingomonas ginsengisoli, Sphingomonas ginsenosidimutans, Sphingomonas glacialis, Sphingomonas haloaromaticamans, Sphingomonas hankookensis, Sphingomonas herbicidovorans, Sphingomonas histidinilytica, Sphingomonas indica, Sphingomonas insulae, Sphingomonas japonica, Sphingomonas jaspsi, Sphingomonas jejuensis, Sphingomonas jinjuensis, Sphingomonas kaistensis, Sphingomonas koreensis, Sphingomonas laterariae, Sphingomonas leidyi, Sphingomonas macrogolitabida, Sphingomonas macrogoltabidus, Sphingomonas mali, Sphingomonas melonis, Sphingomonas molluscorum, Sphingomonas mucosissima, Sphingomonas natatoria, Sphingomonas oligophenolica, Sphingomonas oryziterrae, Sphingomonas panni, Sphingomonas parapaucimobilis, Sphingomonas paucimobilis, Sphingomonas phyllosphaerae, Sphingomonas pituitosa, Sphingomonas polyaromaticivorans, Sphingomonas pruni, Sphingomonas pseudosanguinis, Sphingomonas rosa, Sphingomonas roseiflava, Sphingomonas rubra, Sphin-*

*gomonas sanguinis, Sphingomonas sanxanigenens, Sphingomonas sediminicola, Sphingomonas soli, Sphingomonas starnbergensis, Sphingomonas stygia, Sphingomonas subarctica, Sphingomonas suberifaciens, Sphingomonas subterranean, Sphingomonas taejonensis, Sphingomonas terrae, Sphingomonas trueperi, Sphingomonas ursincola, Sphingomonas wittichii, Sphingomonas xenophaga, Sphingomonas xinjiangensis, Sphingomonas yabuuchiae, Sphingomonas yanoikuyae*, and *Sphingomonas yunnanensis*.

In another embodiment, the bacteria are GRAS species in the gamma-proteobacteria phylum, such as *Halomonas elongata, Hafnia alvei*, excluding *Hafnia alvei*.

In another embodiment, the bacteria are from the genus of Alpha-proteobacteria phylum, including but not limited to, the GRAS species *Acetobacter aceti* subsp. *Aceti, Acetobacter fabarum, Acetobacter lovaniensis, Acetobacter malorum, Acetobacter orientalis, Acetobacter pasteurianus* subsp. *Pasteurianus, Acetobacter pomorum, Acetobacter syzygii, Acetobacter tropicalis Gluconacetobacter azotocaptans, Gluconacetobacter diazotrophicus, Gluconacetobacter entanii, Gluconacetobacter europaeus, Gluconacetobacter hansenii, Gluconacetobacter johannae, Gluconacetobacter oboediens, Gluconobacter oxydans*, and *Gluconacetobacter xylinus*.

In another embodiment, the bacteria are *Zymomonas mobilis* subsp. *Mobilis*.

In another embodiment, the bacteria are from the Bacteriodetes phylum, including but not limited to, *Bacteroides xylanisolvens* strain DSM 23964.

In another embodiment, the bacteria are from the genus of *Bifidobacterium*, including but not limited to, *Bifidobacterium adolescentis, Bifidobacterium adolescentis* ATCC 15703, *Bifidobacterium adolescentis* L2-32, *Bifidobacterium angulatum, Bifidobacterium, angulatum* DSM 20098=JCM 7096, *Bifidobacterium animalis, Bifidobacterium animalis* subsp. *Animalis, Bifidobacterium animalis* subsp. *animalis* ATCC 25527, *Bifidobacterium animalis* subsp. *Lactis, Bifidobacterium animalis* subsp. *lactis* AD011, *Bifidobacterium animalis* subsp. *lactis* ATCC 27673, *Bifidobacterium animalis* subsp. *lactis* B420, *Bifidobacterium animalis* subsp. *lactis* BB-12, *Bifidobacterium animalis* subsp. *lactis* Bi-07, *Bifidobacterium animalis* subsp. *lactis* B1-04, *Bifidobacterium animalis* subsp. *lactis* BLC1, *Bifidobacterium animalis* subsp. *lactis* BS 01, *Bifidobacterium animalis* subsp. *lactis* CNCM 1-2494, *Bifidobacterium animalis* subsp. *lactis* DSM 10140, *Bifidobacterium animalis* subsp. *lactis* HN019, *Bifidobacterium animalis* subsp. *lactis* V9, *Bifidobacterium asteroids, Bifidobacterium asteroides* PRL2011, *Bifidobacterium biavatii, Bifidobacterium bifidum, Bifidobacterium bifidum* ATCC 29521=JCM 1255, *Bifidobacterium bifidum* BGN4, *Bifidobacterium bifidum* CECT 7366, *Bifidobacterium bifidum* DSM 20215, *Bifidobacterium bifidum* IPLA 20015, *Bifidobacterium bifidum* JCM 1254, *Bifidobacterium bifidum* LMG 13195, *Bifidobacterium bifidum* NCIMB 41171, *Bifidobacterium bifidum* PRL2010, *Bifidobacterium bifidum* S17, *Bifidobacterium bombi, Bifidobacterium boum, Bifidobacterium breve, Bifidobacterium breve* ACS-071-V-Sch8b, *Bifidobacterium breve* CECT 7263, *Bifidobacterium breve* DPC 6330, *Bifidobacterium breve* DSM 20213=JCM 1192, *Bifidobacterium breve* EX336960VC18, *Bifidobacterium breve* EX336960VC19, *Bifidobacterium breve* EX336960VC21, *Bifidobacterium breve* EX533959VC21, *Bifidobacterium breve* HPH0326, *Bifidobacterium breve* JCP7499, *Bifidobacterium breve* S27, *Bifidobacterium breve* UCC2003, *Bifidobacterium callitrichos, Bifidobacterium catenulatum, Bifidobacterium catenulatum* DSM 16992=JCM 1194, *Bifidobacterium choerinum, Bifidobacterium choerinum* DSM 20434, *Bifidobacterium coagulans, Bifidobacterium indicum, Bifidobacterium kashiwanohense, Bifidobacterium kashiwanohense* JCM 15439, *Bifidobacterium longum, Bifidobacterium longum* 3_1_37 DFAAB, *Bifidobacterium longum* AGR2137, *Bifidobacterium longum* BORI, *Bifidobacterium longum* D2957, *Bifidobacterium longum* DJO10A, *Bifidobacterium longum* NCC2705, *Bifidobacterium longum* subsp. *Infantis, Bifidobacterium longum* subsp. *infantis* 157F, *Bifidobacterium longum* subsp. *infantis* ATCC 15697=JCM 1222, *Bifidobacterium longum* subsp. *infantis* CCUG 52486, *Bifidobacterium longum* subsp. *Longum, Bifidobacterium longum* subsp. *longum* 1-6B, *Bifidobacterium longum* subsp. *longum* 2-2B, *Bifidobacterium longum* subsp. *longum* 35B, *Bifidobacterium longum* subsp. *longum* 44B, *Bifidobacterium longum* subsp. *longum* ATCC 55813, *Bifidobacterium longum* subsp. *longum* BBMN68, *Bifidobacterium longum* subsp. *longum* CECT 7347, *Bifidobacterium longum* subsp. *longum* CMCC P0001, *Bifidobacterium longum* subsp. *longum* F8, *Bifidobacterium longum* subsp. *longum* JCM 1217, *Bifidobacterium longum* subsp. *longum* JDM301, *Bifidobacterium longum* subsp. *longum* KACC 91563, *Bifidobacterium longum* subsp. *Suis, Bifidobacterium magnum, Bifidobacterium magnum* DSM 20222, *Bifidobacterium coryneforme, Bifidobacterium crudilactis, Bifidobacterium cuniculi, Bifidobacterium dentium, Bifidobacterium dentium* ATCC 27678, *Bifidobacterium dentium* ATCC 27679, *Bifidobacterium dentium* Bd1, *Bifidobacterium dentium* JCM 1195, *Bifidobacterium dentium* JCVIHMP022, *Bifidobacterium gallicum, Bifidobacterium gallicum* DSM 20093, *Bifidobacterium gallinarum, Bifidobacterium simiae, Bifidobacterium stellenboschense, Bifidobacterium stercoris, Bifidobacterium subtile, Bifidobacterium subtile* DSM 20096, *Bifidobacterium merycicum, Bifidobacterium minimum, Bifidobacterium minimum* DSM 20102, *Bifidobacterium mongoliense, Bifidobacterium pseudocatenulatum, Bifidobacterium pseudocatenulatum* D2CA, *Bifidobacterium pseudocatenulatum* DSM 20438=JCM 1200, *Bifidobacterium pseudolongum, Bifidobacterium pseudolongum* AGR2145, *Bifidobacterium pseudolongum* subsp. *Globosum, Bifidobacterium pseudolongum* subsp. *Pseudolongum, Bifidobacterium psychraerophilum, Bifidobacterium pullorum, Bifidobacterium pullorum* ATCC 49618, *Bifidobacterium reuteri, Bifidobacterium ruminantium, Bifidobacterium saeculare, Bifidobacterium saguini, Bifidobacterium scardovii, Bifidobacterium scardovii* JCM 12489, *Bifidobacterium thermacidophilum, Bifidobacterium thermacidophilum* subsp. *Porcinum, Bifidobacterium thermacidophilum* subsp. *Thermacidophilum, Bifidobacterium thermophilum, Bifidobacterium thermophilum* RBL67, *Bifidobacterium tsurumiense, Bifidobacterium tsurumiense* DSM 17777, *Bifidobacterium* sp. *Bifidobacterium breve* M-16V, *Bifidobacterium animalis* subsp. *lactis* strains HN019, Bi-07, B1-04 and B420, *Bifidobacterium animalis* subsp. *lactis* strain Bf-6, *Bifidobacterium longum* strain BB536, and *Bifidobacterium lactis* strain Bb12.

In another embodiment, the bacteria are from the genus of *Carnobacterium*, including but not limited to, *Carnobacterium alterfunditum, Carnobacterium divergens, Carnobacterium funditum, Carnobacterium gallinarum, Carnobacterium inhibens, Carnobacterium jeotgali, Carnobacterium maltaromaticum, Carnobacterium maltaromaticum* 38b, *Carnobacterium maltaromaticum* ATCC 35586, *Carnobacterium maltaromaticum* LMA28, *Carnobacterium mobile, Carnobacterium pleistocenium, Carnobacterium viridians, Carnobacterium* sp., *Carnobacterium* sp. 'eilaticum 021211', *Carnobacterium* sp. 11-1, *Carnobacterium* sp. 12266/2009, *Carnobacterium* sp. 13-3, *Carnobacterium* sp. 17-4, *Carnobacterium* sp. 22-6, *Carnobacterium* sp. 2673, *Carnobacterium* sp. 27L, *Carnobacterium* sp. 35L, *Carnobacterium* sp. 37-3-1, *Carnobacterium* sp. 38ANAV, *Carnobacterium* sp. 40L, *Carnobacterium* sp. 7196, *Carnobacterium* sp. A, *Carnobacterium* sp. A2S10L14, *Carnobacterium* sp. A4, *Carnobacterium* sp. A726, *Carnobacterium* sp. aG53, *Carnobacterium* sp. ARCTIC-P2, *Carnobacterium* sp. ARCTIC-P26, *Carnobacterium* sp. ARCTIC-P35, *Carnobacterium* sp. AT12, *Carnobacterium* sp. AT7, *Carnobacterium* sp. B, *Carnobacterium* sp. B5, *Carnobacterium* sp. BA-81, *Carnobacterium* sp. BBDP54, *Carnobacterium* sp. BBDP71, *Carnobacterium* sp. BM-8, *Carnobacterium* sp. BM-81, *Carnobacterium* sp. C-13, *Carnobacterium* sp. c58, *Carnobacterium* sp. cG53, *Carnobacterium* sp. CM1, *Carnobacterium* sp. D35, *Carnobacterium* sp. D4, *Carnobacterium* sp. D5, *Carnobacterium* sp. EK-153, *Carnobacterium* sp. ES-11, *Carnobacterium* sp. FBT1-19, *Carnobacterium* sp. FBT1-22, *Carnobacterium* sp. FBT3-14, *Carnobacterium* sp. FBT3-9, *Carnobacterium* sp. FBT4-1, *Carnobacterium* sp. FBT4-18, *Carnobacterium* sp. G1516J1L, *Carnobacterium* sp. G4a-1, *Carnobacterium* sp. G5a-1, *Carnobacterium* sp. GCM1, *Carnobacterium* sp. H126a, *Carnobacterium* sp. Hg4-03, *Carnobacterium* sp. I-Bh20-14, *Carnobacterium* sp. I-Bh4-26, *Carnobacterium* sp. KA-2, *Carnobacterium* sp. KA-8, *Carnobacterium* sp. KH1, *Carnobacterium* sp. KOPRI80142, *Carnobacterium* sp. KOPRI80153, *Carnobacterium* sp. KOPRI80155, *Carnobacterium* sp. L02-6127, *Carnobacterium* sp. LIV10, *Carnobacterium* sp. LMG 26642, *Carnobacterium* sp. LV62:W1, *Carnobacterium* sp. LV66, *Carnobacterium* sp. M7-C10, *Carnobacterium* sp. MARL15, *Carnobacterium* sp. MKJ37, *Carnobacterium* sp. NFU35-25, *Carnobacterium* sp. NJ-46, *Carnobacterium* sp. R-36982, *Carnobacterium* sp. RI234, *Carnobacterium* sp. S171, *Carnobacterium* sp. S181, *Carnobacterium* sp. Sd5t18, *Carnobacterium* sp. Sd5t5, *Carnobacterium* sp. Sd6t1, *Carnobacterium* sp. Sd6t15, *Carnobacterium* sp. Sd6t17, *Carnobacterium* sp. Sd6t18, *Carnobacterium* sp. SR2-31-1, *Carnobacterium* sp. St2, *Carnobacterium* sp. T301, *Carnobacterium* sp. UI49, *Carnobacterium* sp. UPAA77, *Carnobacterium* sp. UST050418-652, *Carnobacterium* sp. WFPIS001, *Carnobacterium* sp. WN1359, *Carnobacterium* sp. WN1370, *Carnobacterium* sp. WN1371, *Carnobacterium* sp. WN1372, *Carnobacterium* sp. WN1373, *Carnobacterium* sp. WN1374, *Carnobacterium* sp. Y6, *Carnobacterium divergens*, *Carnobacterium maltaromaticum*, *Carnobacterium piscicola*, *Carnobacterium maltaromaticum* strain CB1 (viable and heat-treated), and *Carnobacterium maltaromaticum* strain CB1.

In another embodiment, the bacteria are from the genus of *Pediococcus*, including but not limited to, *Pediococcus acidilactici*, *Pediococcus acidilactici* 7_4, *Pediococcus acidilactici* D3, *Pediococcus acidilactici* DSM 20284, *Pediococcus acidilactici* MA18/5M, *Pediococcus argentinicus*, *Pediococcus cellicola*, *Pediococcus claussenii*, *Pediococcus claussenii* ATCC BAA-344, *Pediococcus damnosus*, *Pediococcus damnosus* 9-6b, *Pediococcus ethanolidurans*, *Pediococcus inopinatus*, *Pediococcus lolii*, *Pediococcus lolii* NGRI 0510Q, *Pediococcus parvulus*, *Pediococcus parvulus* CIRM 750, *Pediococcus pentosaceus*, *Pediococcus pentosaceus* ATCC 25745, *Pediococcus pentosaceus* IE-3, *Pediococcus siamensis*, *Pediococcus stilesii*, *Pediococcus* sp. 14.8.17, *Pediococcus* sp. BGM59, *Pediococcus* sp. BZ-2005, *Pediococcus* sp. CAT-100BC, *Pediococcus* sp. CR-6S, *Pediococcus* sp. CRA51, *Pediococcus* sp. EDB-LI4, *Pediococcus* sp. epsi2-MSE-E3-2, *Pediococcus* sp. epsi3l-MSE-E3-2, *Pediococcus* sp. FUA 3137, *Pediococcus* sp. FUA 3140, *Pediococcus* sp. FUA 3226, *Pediococcus* sp. GS4, *Pediococcus* sp. IBUN 186, *Pediococcus* sp. 1E3, *Pediococcus* sp. IJ-K1, *Pediococcus* sp. J-11, *Pediococcus* sp. KDLLL3-1, *Pediococcus* sp. L04, *Pediococcus* sp. LAB4012, *Pediococcus* sp. Lact10, *Pediococcus* sp. LQC 1953, *Pediococcus* sp. LQC 1957, *Pediococcus* sp. LQC 1963, *Pediococcus* sp. LQC 1966, *Pediococcus* sp. LQC 1972, *Pediococcus* sp. MB2C, *Pediococcus* sp. MB2D, *Pediococcus* sp. MFC1, *Pediococcus* sp. MMZ60A, *Pediococcus* sp. MUU10, *Pediococcus* sp. MUU13, *Pediococcus* sp. MUU2, *Pediococcus* sp. MUU3, *Pediococcus* sp. MUU4, *Pediococcus* sp. NBRC 106004, *Pediococcus* sp. NBRC 106014, *Pediococcus* sp. NBRC 106015, *Pediococcus* sp. NBRC 106028, *Pediococcus* sp. NBRC 106032, *Pediococcus* sp. NBRC 107178, *Pediococcus* sp. NBRC 107186, *Pediococcus* sp. NBRC 107193, *Pediococcus* sp. NBRC 107213, *Pediococcus* sp. NBRC 107218, *Pediococcus* sp. NBRC 107221, *Pediococcus* sp. NBRC 107222, *Pediococcus* sp. NBRC 107244, *Pediococcus* sp. NBRC 107250, *Pediococcus* sp. NBRC 107256, *Pediococcus* sp. NBRC 107260, *Pediococcus* sp. NBRC 107264, *Pediococcus* sp. NBRC 107299, *Pediococcus* sp. NBRC 107306, *Pediococcus* sp. NBRC 107309, *Pediococcus* sp. NBRC 107310, *Pediococcus* sp. NBRC 107331, *Pediococcus* sp. NBRC 107343, *Pediococcus* sp. NBRC 107346, *Pediococcus* sp. NBRC 107350, *Pediococcus* sp. NIR1, *Pediococcus* sp. NIR3, *Pediococcus* sp. omega41-FH-E3-2, *Pediococcus* sp. P14, *Pediococcus* sp. Pom3, *Pediococcus* sp. Pom4, *Pediococcus* sp. Pom7, *Pediococcus* sp. Pov5, *Pediococcus* sp. Pov7, *Pediococcus* sp. Pov8, *Pediococcus* sp. QCH-42, *Pediococcus* sp. QCH-66, *Pediococcus* sp. QCH-67, *Pediococcus* sp. QMA-03G, *Pediococcus* sp. QMA-06CH, *Pediococcus* sp. QMA-07G, *Pediococcus* sp. QMA-11, *Pediococcus* sp. QMA-21BC, *Pediococcus* sp. QMA-23BC, *Pediococcus* sp. QMA-24BC, *Pediococcus* sp. QMA-27BC, *Pediococcus* sp. Rrt8, *Pediococcus* sp. Rrt9, *Pediococcus* sp. Rrv1, *Pediococcus* sp. Rrv3, *Pediococcus* sp. S17, *Pediococcus* sp. S18, *Pediococcus* sp. SD2, *Pediococcus* sp. Shahsavar, *Pediococcus* sp. siga1, *Pediococcus* sp. T1R1C23, *Pediococcus* sp. T1R4C24, *Pediococcus* sp. Te6, *Pediococcus* sp. YCO-02, *Pediococcus* sp. YCO-04, *Pediococcus* sp. YCO-09, *Pediococcus* sp. YCO-10, *Pediococcus* sp. YCO-11, *Pediococcus* sp. YCO-12, *Pediococcus* sp. YCO-13, *Pediococcus* sp. YCO-16, *Pediococcus* sp. YCO-17, *Pediococcus* sp. YCO-18, *Pediococcus* sp. YCO-23, *Pediococcus* sp. YCO-25, *Pediococcus* sp. YCO-26, *Pediococcus* sp. YCO-28, *Pediococcus* sp. YXC-17, *Pediococcus* sp. Z-17, *Pediococcus acidilactici* strain NP3, *Pediococcus acidilactici*, *Pediococcus acidilactici*, *Pediococcus parvulus*, and *Pediococcus pentosaceus*.

In one embodiment, any bacteria, listed herein or otherwise known that is pathogenic and/or is an opportunistic pathogenic species is excluded. In another embodiment, the bacteria selected for transformation and to be included in the composition is any one of the bacterial genus listed herein or any one of the specific bacterial species listed herein, or any collection of first and second bacteria listed herein.

In one embodiment, the bacterial for use in the composition is any bacteria capable of existing on skin, in particular human skin, and more particularly bacteria that reside on human skin and are GRAS bacteria, excluding pathogenic and/or opportunistic bacteria.

In one embodiment, the composition comprises a population of transformed bacteria and a population of bacteria not transformed to express a compound of interest, e.g., the composition is comprised of a transformed bacteria population and a naturally occurring or probiotic bacteria. Compositions comprising more than one population of bacteria, wherein each population is a collection of individual transformed bacteria for expression of different compounds of interest, as each individual cell able to express more than one compound of interest or each individual cell express one compound, and the collection of different individuals expressing different molecules of interest express different compounds of interest, or wherein one population is transformed and one population is not transformed, are also contemplated. In one embodiment, the composition comprises first and second populations of transformed bacteria formulated for topical application to a subject. In one embodiment, the second population of transformed bacteria is either or both (i) created from a non-pathogenic bacteria that is different from the first population of transformed bacteria in the composition or (ii) transformed to express a compound of interest that is different from the first compound of interest expressed by the first population of transformed bacteria in the composition.

The bacteria may be included in a composition in a live, attenuated, semi-active or inactivated, or dead form. According to one particular embodiment, these bacteria are used in a live form, and are capable of chronically expressing the compound of interest upon topical application of the composition in which they are formulated. They may also be included in the form of cell component fractions or in the form of metabolites. The bacterial species(s), molecule(s) of interest or fraction(s) may also be introduced in the form of a lyophilized powder, of a culture supernatant, of harvested compound, and/or where appropriate, in a concentrated form.

According to one variation, the compositions may also contain a divalent inorganic cation. The compositions may be in any of the galenical forms usually available for the method of administration selected. The active molecule synthesized by the bacteria (which in one embodiment are skin bacteria) could be could either stay in the bacteria or secreted outside to the skin.

Limiting factors can control the bacterial growth. Such limiting factors can exist naturally on the skin and in one embodiment may be included in the composition that is to be applied topically to a subject to be treated. One or more limiting factors may be included in the formulation. In another embodiment the limiting factors are added to complementary products such as soaps, body wash, shampoo, lotion to enrich and nourish the composition, and to keep it active or alive. Examples for limiting factors include amino acids, biotin, nicotinamide and thiamine, pantothenate, riboflavin, folic acid, keratin, lipids, lactate, and melanins. A preferred limiting factor may be the amino acid L-alanin. Bacterial growth can be controlled by the mechanism of origin of replication to limit bacterial cycles. Bacterial cycles can be limited to 50 cycles, or bacterial cycles can be limited to 2-40 cycles. Limitation of bacterial growth can also be achieved by physical environmental factors as pH and temperature.

B. Exemplary Compounds of Interest

As described above, the bacteria species selected for the composition is transformed using known recombinant techniques to express a compound of interest. Exemplary compounds of interest are listed in Table 1 below, along with an indication of the skin disorder or condition or purpose for which the compound is used:

TABLE 1

| Purpose of Compound | Active compound |
| --- | --- |
| UV protection (sunscreen; UVA, UVB) | Mycosporine, gadusols, oxo-mycosporines, imino-mycosporines and mycosporine-like amino acids (MAA; glycosylated or covalently bound to oligosaccharides, oligosaccharide-linked MAAs). Intracellular or extracellular. Examples include: gadusol, deoxygadusol, 4-Deoxygadusol (S2), shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, playthenic acid-337, playthenic acid-335, palythine-serine, palythine-threonine, palythine-threonine-sulphate, playthine-serine-sulphate, euhalothece, mycosporine-alanine (2-(e)-2,3-dihydroxipro-1-enylimino-mycosporine-alanine), scytonemin<br>Molecules with sequence similarity to MAAs, such as dehydroquinate synthase homolog (DHQS homolog) and ATP-grasp<br>Melamines, including eumelanin-(or dihydroxyphenylalanine (DOPA) melanins), pheomelanin allomelanins, pyomelanine, dopamelanin, neuromelanin<br>UV-screening/observing amino acids-like molecules, such as urocanic acid<br>Flavonoids, Anthocyanines and anthoxantins, and Anthocyanidins<br>Betalanines, such as betacyanin and betaxanthins<br>UV-screening/observing Pigments, such as Carotenoids/cartenoproteins, carotens, lycopene, xanthopylls, lutins, zeaxanthin, porphyrin-based/heme-porphyrin based, chlorophyll-II<br>UV-screening/observing co-factors, such as tetrahydrobiopterin and phenylpropanoids<br>Polyphenol, Tannins, Phlorotannins, dieckol, eckol, Flavan-3-ols or flavanols, pycnogenol<br>sargaquinoic acid, sargachromenol, sphaerophorin (depside) pannarin (depsidone)<br>DNA repair enzymes, that repair damage caused by exposure to UV, like photolyase, endonuclease and DNA glycosylases |
| Psoriasis | Retinoid, Vitamin A, beta-caroten, Vit D and it's derivatives, Anti-inflammatory cytokines such as Interleukin-2 (IL-2) |

TABLE 1-continued

| Purpose of Compound | Active compound |
|---|---|
| Dry Skin | Polymers, such as polyol and glycerol; skin related natural compounds, such as collagen, keratin, elastin, linoleic acid, laminin, tretinoin, tazarotene, sargaquinoic acid, sargachromenol, fucoxanthin, retinoid |
| Relief of oxidative stress caused by UV; Anti-Oxidants, Anti-reactive oxygen species (Anti-ROS)/ Anti-Aging, moisturizing and cosmetics | Tyrosinases (and its substrates and products) alpha hydroxy acids (AHAs), such as glycolic acid, lactic acid and citric acid Polysaccharides; Glycosaminoglycans, (GAGs) or mucopolysaccharides; Hyaluronan (also called hyaluronic acid or hyaluronate or HA) Skin related cofactors, such as Vitamin A, Vitamin C or L-ascorbic acid, or simply ascorbate; Biopterin; Coenzyme A (CoA, CoASH, or HSCoA); Coenzyme Q10, ubiquinone, ubidecarenone, coenzyme Q; CoQ10; Molybdopterin Vitamin E; alpha, beta, gamma, delta-tocopherols and alpha, beta, gamma, delta-tocotrienols Polymers, such as Polyol and Glycerol, Skin related natural compounds, such as collagen, keratin, elastin, linoleic acid, laminin, tretinoin, tazarotene, sargaquinoic acid, sargachromenol, fucoxanthin, retinoid, anti-inflammatory cytokines (such as IL-2), cortisone, tacrolimus, cyclosporine, resveratrol, gallocatechol, gallocatechin, epigallocatechin gallate |
| Eczema | cortisone, tacrolimus, cyclosporine |
| Wound healing/ Diabetic wounds/Ulcers | anaerobic bacteria delivering oxygen |
| Intertrigo/ diaper rash | talcum, starch |

In one embodiment, a composition for use in protection of skin from ultraviolet radiation is contemplated. That is, the composition is for use as a sunscreen, to absorb or reflect ultraviolet A radiation, typically at a wavelength of between 320-400 nm, ultraviolet B radiation, typically at a wavelength of between 315-280 nm, or both UVA and UVB absorbing and/or reflecting. The transformed bacteria in the composition express one or more of the following exemplary compounds of interest in Group 1, Group 2, Group 3, Group 4, Group 5, Group 6, Group 7, Group 8, Group 9, Group 10, Group 11 and Group 12:

Group 1—mycosporine, gadusols, oxo-mycosporines, imino-mycosporines and mycosporine-like Amino Acids (MAA; glycosylated or covalently bound to oligosaccharides, oligosaccharide-linked MAAs); and/or intracellular or extracellular gadusol, deoxygadusol, 4-Deoxygadusol (S2), shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, playthenic acid-337, playthenic acid-335, palythine-serine, palythine-threonine, palythine-threonine-sulphate, playthine-serine-sulphate, euhalothece, mycosporine-alanine (2-(e)-2,3-dihydroxipro-1-enylimino-mycosporine-alanine);

Group 2—Scytonemin;

Group 3—Melanines: eumelanin- (or dihydroxyphenylalanine (DOPA) melanins), pheomelanin allomelanins, pyomelanine, dopamelanin, neuromelanin;

Group 4—UV-screening/observing amino acids-like molecules: urocanic acid;

Group 5—Flavonoids: Anthocyanines and anthoxantins, Anthocyanidins;

Group 6—Betalanines: betacyanin, betaxanthins;

Group 7—Molecules with sequence similarity to MAAs: dehydroquinate synthase homolog (DHQS homolog), ATP-grasp;

Group 8—UV-screening/observing pigments: Carotenoids/cartenoproteins, carotens, lycopene, Xanthopylls, lutins, zeaxanthin, porphyrin-based/heme-porphyrin based, chlorophyll-II;

Group 9—UV-screening/observing co-factors, such as tetrahydrobiopterin and biopterin;

Group 10—Phenylpropanoids;

Group 11—Tannins: Phlorotannins, dieckol, eckol; and

Group 12—Sargaquinoic acid, sargachromenol, sphaerophorin (depside), pannarin (depsidone);

Group 13—DNA repair enzymes that repair damage caused by exposure to UV, such as photolyase, endonuclease, and DNA glycosylase.

In one embodiment, the compound of interest is any one of the compounds listed in any one of Groups 1-13 alone.

In another embodiment, a composition for use in providing relief of oxidative stress is contemplated, for use as a cosmetic or anti-aging composition. The composition may provide relief form UV exposure, as an anti-oxidant composition. The transformed bacteria in the composition express one or more of the following exemplary compounds of interest in Group 1, Group 2, Group 3, Group 4, Group 5, Group 6 and Group 7:

Group 1—Tyrosinases (and its substrates and products);

Group 2—Alpha hydroxy acids (AHAs): Glycolic acid, lactic acid, and citric acid;

Group 3—Polysaccharides: glycosaminoglycans, (GAGs), mucopolysaccharides, hyaluronan (also called hyaluronic acid or hyaluronate or HA);

Group 4—Skin related cofactors: Vitamin C or L-ascorbic acid, or simply ascorbate, Vitamin A, Biopterin, Coenzyme A (CoA, CoASH, or HSCoA), Coenzyme Q10 (ubiquinone, ubidecarenone, coenzyme Q, CoQ10), Molybdopterin;

Group 5—Vitamin E: alpha, beta, gamma, delta-tocopherols, alpha, beta, gamma, delta-tocotrienols;

Group 6—Polymers: Polyol, Glycerol;

Group 7—Additional skin related natural compounds, such as collagen, keratin, elastin, linoleic acid, laminin, tretinoin, tazarotene, sargaquinoic acid, sargachromenol, fucoxanthin, retinoid, anti-inflammatory cytokines (such as IL-2), cortisone, tacrolimus, ciclosporin, resveratrol, gallocatechol, gallocatechin, and epigallocatechin gallate.

In other embodiments, a composition for use in treating active dermatitis, acne, burns, insect bites, hives, dandruff and body odor is contemplated. A person of skill in the art can identify compounds of interest to be expressed in the transformed bacteria for treatment of these conditions.

Compounds having sequence similarity to the sequences of the compounds listed in the table above are also contemplated and may be regarded as identical compounds. Two sequences are said to be "substantially identical and identical" if the sequence of nucleotides or amino acid residues, respectively, in the two sequences has similarity of at least 40%, when aligned for maximum correspondence as described below. Alternatively, percent identity can be any integer from 20% to 100%. More preferred embodiments include at least: 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98 or 99% compared to a reference sequence (e.g., SEQ ID NO:1, 2, 3, 4, 5, 6, 7, 8, 9, 10, 11, 12, 13, 14, 18) using the programs described herein, such as BLAST using standard parameters, as described below. This definition also refers to the complement of a test sequence, when the test sequence has substantial identity to a reference sequence.

Compounds having a conserved protein domain with sequence similarity to the sequences of the domains of the proteins of the compounds listed in the table above, are also contemplated and may be regarded as identical compounds.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

Methods of alignment of sequences for comparison are well-known in the art. As the use of the following programs (provided by the National Center for Biotechnology Information) may be used to determine homologies/identities: BLAST, gapped BLAST, BLASTN and PSI-BLAST, which may be used with default parameters. Optimal alignment of sequences for comparison can be conducted by different methods known in the art, such as, but not limited to, the algorithms of Waterman, Needleman, Pearson, or by manual alignment and visual inspection.

Because of the degeneracy of the genetic code, a large number of functionally identical nucleic acids encode any given protein. One of skill will recognize the individual codon usage to a nucleic acid, peptide, polypeptide, or protein sequence that alters, adds or deletes a single amino acid or a small percentage of amino acids in the encoded sequence to allow the coding of the compound of interest.

It will be appreciated that the composition can be used in combination with existing topical compositions intended for treatment of the same or another disorder or condition. For example, the composition described herein for use as a sunscreen may be used in combination with a known sunscreen product, including: titanium dioxide (TiO2), zinc oxide (ZnO), para-aminobenzoic acid, avobenzone, butyl methoxydibenzoylmethane, ensulizole, 2-phenylbenzimidazole-5-sulfonic acid, homosalate, homomenthylsalicylat, meradimate, menthyl 2-aminobenzoate, menthylanthranilate, octinoxate, menthyl 2-aminobenzoate menthylanthranilate, octisalate, 2-ethylhexyl salicylate, octyl salicylate, octocrylene, 2-ethylhexyl-2-cyano-3,3 diphenylacrylate, oxybenzone, benzophenone-3,2-hydroxy-4-methoxybenzophenone, sulisobenzone, benzophenone-4, drometrizoletrisiloxane, mexoryl XL, enzacamene, 4-Methylbenzylidene camphor, padimate-O, octyl dimethyl PABA, σ-PABA, terephthalylidene dicamphor sulfonic acid, mexoryl SX, 3,3'-(1,4-phenylenedimethylidene) bis[7,7-dimethyl-2-oxobicylclo[2.2.1]hept-1-yl methanesulfonic acid), cinoxate, 2-ethoxyethyl 3-(4-methoxyphenyl) propenoate, diethanolamine-methoxycinnamate, dioxybenzone, benzophenone-8, (2-hydroxy-4-methoxyphenyl)-(2-hydroxyphenyl) methanone, triethanolamine salicylate, and trolamine salicylate.

Nucleic acid sequences coding for the compound of interest can be identified by those of skill in the art, and several examples are set forth herein as:

SEQ ID NO:1 DNA sequence for shinorine operon;
SEQ ID NO:2 DNA sequence for shinorine nostoc;
SEQ ID NO:3 AA sequence for Amino acid adenylation_Ava_3855;
SEQ ID NO:4 AA sequence for ATP-grasp enzyme-like protein_Ava_3856;
SEQ ID NO:5 AA sequence for O-methyltransferase, family 3_Ava_3857;
SEQ ID NO:6 AA sequence for 3-dehydroquinate synthase_Ava_3858;
SEQ ID NO:7 DNA Ava_3858_3_dehydroquinate synthase;
SEQ ID NO:8 DNA spacer1_4804128_4803953;
SEQ ID NO:9 DNA Ava_3857_O-methyltransferase;
SEQ ID NO:10 DNA spacer2_4803114_4803099;
SEQ ID NO:11 DNA Ava_3856_ATP-grasp enzyme-like protein;
SEQ ID NO:12 DNA Spacer3_4804128_4803953;
SEQ ID NO:13 DNA Ava_3855_Amino acid adenylation;
SEQ ID NO:16 DNA forward_primer_for shinorine_operon;
SEQ ID NO:17 DNA reverse_primer_for shinorine_operon; and
SEQ ID NO:18 DNA sequence for tyrosynase.

C. Recombinant Molecular Techniques

Techniques for transformation of any of the bacterial species listed herein or otherwise known in the art are understood by skilled artisans. Several techniques are briefly described herein, and factors to consider in such techniques are now discussed, including 1. Modular organization; 2. Vector types; 3. Expression and improving impression techniques; 4. Expression of insert and validation; and 5. Transformation.

1. Modular Organization

The transformed bacterial strains can be regarded as cell factory, or vehicles, producing by any method known in the art recombinant proteins (U.S. Pat. No. 4,259,444, incorporated by reference herein), and would typically include cloning of the isolated nucleic acid molecule that encodes for the compound of interest into an appropriate vector. The expression vector is built in a modular organization, allowing independent design of each component in separate conditions and an easy exchange of all essential elements. In such a modular vector the essential elements typically include: replicon, promoter (constitutive or inducible with regulation system), gene of interest, marker or reporter, resistance or limiting factor, Multiple cloning site (MCS), shine-delgarno (ribosomal binding site), and terminators, as shown in several systems, as the NICE system (Mierau I and Kleerebezem M., *Appl Microbiol Biotechnol.* 68:705-17 (2005), or based on cryptic plasmids (Shareck J. et al., *Crit Rev Biotechnol.* 24:155-208 (2004).

Suitable vectors can be chosen or constructed, containing appropriate regulatory sequences, including promoter sequences, terminator fragments, polyadenylation sequences, enhancer sequences, and other sequences as appropriate. Additional sequences may be added as described above which sequences include a ribosome binding site and a translation start codon.

Appropriate bacterial expression vectors are known to the person skilled in the art as described in Molecular Cloning: a Laboratory Manual: 2nd edition, Sambrook et al., 1989, Cold Spring Harbor Laboratory Press, and there are several studies shown expression vectors for LAB strains, as by Wang T. T. and Lee B. H., *Plasmids in Lactobacillus. Crit Rev Biotechnol.* 17:227-72 (1997), and specifically in the food industry by Nguyen T. T. et al., *J Agric Food Chem.* 59:5617-24 (2011).

Exemplary essential building blocks of a vector are listed in Table 2 below, allowing modular configuration of a backbone plasmid, with different combinations, for a suitable expression of the molecule of interest:

TABLE 2

| Replicon | Promoter-inducible (inducer) | Promoter-constitutive | Marker or reporter | Terminator |
|---|---|---|---|---|
| Ori + repA, p15A, p353-1, p353-2, P8014-2, pA1-derived, pAI, pAM-beta-1, pBG10, pBM02, pC194, pCI305, pCI528, pD125, pFX1/3, pG+, pGK12, pGT633, pLA106, pLAB1000, pLB10, pLC2, PLF1311, pLJ1, pLP1, pLP825, pLPE323, PLUL631, pND302, pND324, pOri+, pPM4, pPSC, pPSC20/22, pSH71, pSK11L, pVS40, pWC1, pWS97, pWV01, pWV02, rep256, repD + E | Bacteriocin, dnaJ (from usp45; High Temp), FOS, gadC-GdR (low pH), grac-lac (IPTG), lacA/lacC/lacR (Lactose), lacA/T7 (Lactose), lacF, lacG, lacS-GalR (Lactose), lacZ, NICE system, nisA/F/R/K/P (Nisin), orfX of sakacin Pregulon, PA170 (low pH, low temp.), pgm, phi31 (and ori; phi infection), Porf1, Porf330, PorfX, PpfkA, prtP or ptrM (absence of peptides), PsapA, PsapA (sakacin A), PsapiP, PslpA, PspplP (Sakacin P), PsspA, PsspQ, Ptuf (CDM), Pusp45, rep/op phi rlt (Mitomycin C), represser/operator phirlt (Mytomycin C), sodA (Aeration), tec-Rro12 (high temp), hyA, tre, trpE (absence of tryptophan), xylA (Xylose) | PermB, PldhL, P1 (SPL), P10 (SPL), P11 (SPL), P13 (SPL), P14 (SPL), P15 (SPL), P16 (SPL), P17 (SPL), P20 (SPL), P21, P21 (SPL), P22 (SPL), P23, P23 (SPL), P25 (SPL), P27 (SPL), P29 (SPL), P3 (SPL), P30 (SPL), P31 (SPL), P32 (weak), P33 (SPL), P34 (SPL), P35 (SPL), P38 (SPL), P4 (SPL), P40 (SPL), P41 (SPL), P42 (SPL), P43 (SPL), P44 (SPL), P44 (weak), P46 (SPL), P47 (SPL), P48(SPL), P5 (SPL), P59, P6 (SPL), P8 (SPL), P9 (SPL), Pami, Ppgm, Pspac, Pveg, PrRNA1-a, PrRNA1-b, PrRNA2-b, PrRNA3-a, PrRNA3-b, PrRNA4-a, PrRNA4-b, PrRNA5-a, PrRNA5-b, Pslp | cml-chloramphenicol, (alr) alanin racemase gene, Abr, amp (Ap)-ampicillin, amyS, ccpA, cloxacillin, Cmr, ermL, ery/em-erythromycin resistance marker, estA, genes for TTFC, gentamycin, GusA (beta-glucuronidas), Kanamycin, LacZ, luxAB, msmR, neomycin, nisI, nsr, penicillin, PepN (aminopeptidase N), pepO, ptsH, streptomycin, tetracycline | LacZ terminator, lollypop structure, T1T2, Tcat194, term667, term908, TpepA, TpepN, TsaiA |

The modular organization is a construct that is capable of expression of the coding sequence by the bacterial host cell. In particular such a vector is either an expression vector or a chromosomal integration vector, such as for example described in Steidler L. et al., Nature Biotechnology, 21(7): 785-789 (2003), or by Pérez-Arellano I. et al., *Plasmid* 46:106-16 (2001).

Figure 1B:
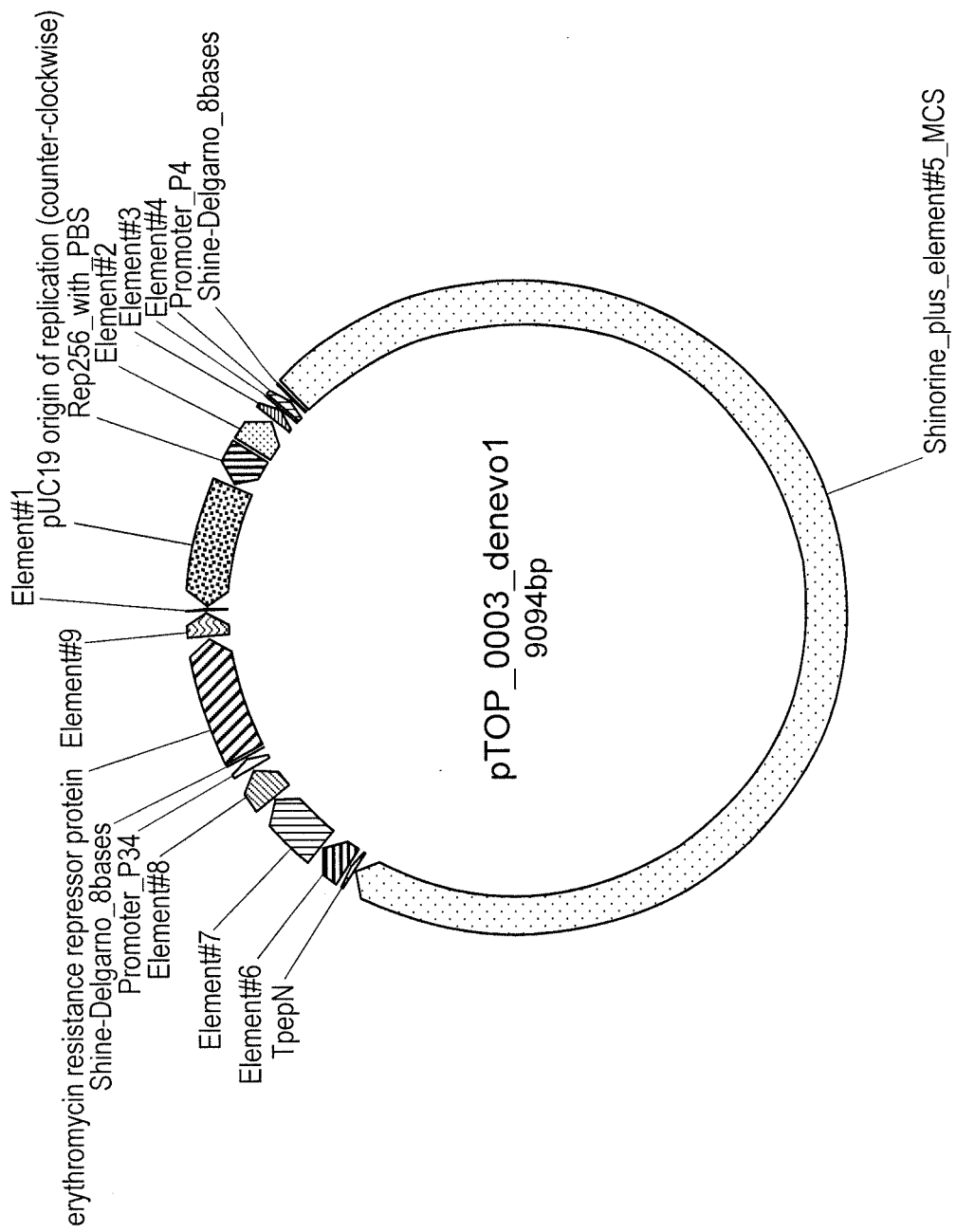
Figure 1C:
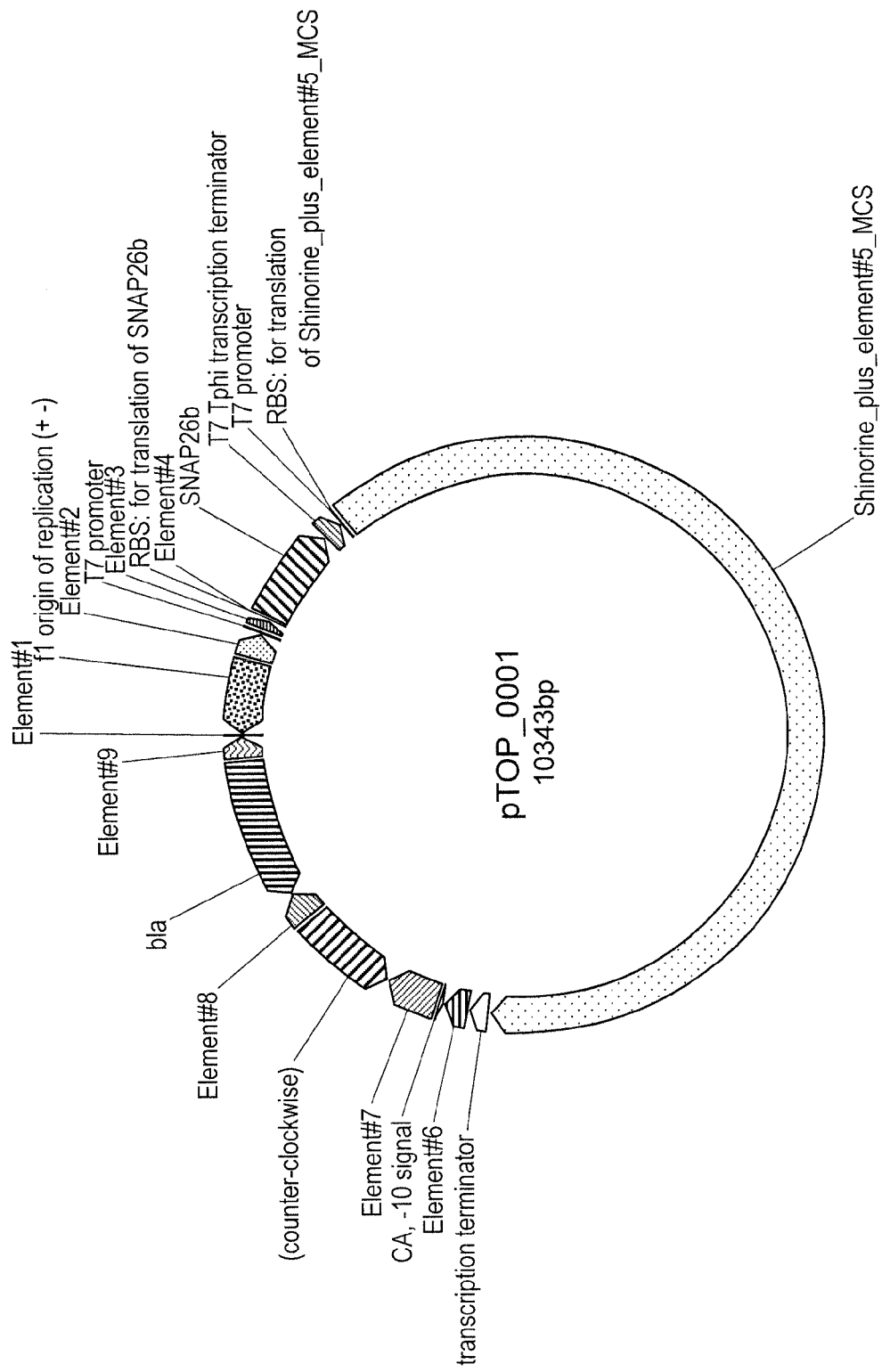

Vectors for transformation of the bacteria can be designed by skilled artisans. Examples are set forth in FIGS. 1A-C, and as a sequence in SEQ ID NO:15 (with restriction enzyme recognition sites (FIG. 1A)), and as in SEQ ID NO:14 (one embodiment of a shinorine operon). In one embodiment, the vector contains a compatible backbone origin of replication to the bacteria strain in use, a compatible promoter for the expression of molecule of interest, and a compatible resistance gene. The plasmid can contain sequences of restriction enzymes. Table 3 sets forth the sequences corresponding to the restriction enzyme recognition sites indicated on the map of FIG. 1A by a respective SEQ ID NO:

TABLE 3

| Seq. ID No. | Sequence |
|---|---|
| 19 | GCAnnnnnnTGCnnnnnnnnnn_nn' |
| 20 | GGAGnnnnnGTnnnnnnnnn_nnn' |
| 21 | ACnnnnnCTCCnnnnnnnn_nnn' |
| 22 | C'GGCC_G |
| 23 | GTA'TAC |
| 24 | GACCGAnnnnnnnnnn_nn' |
| 25 | Cy'CG_rG |
| 26 | C'yCGr_G |
| 27 | TCG'CGA |
| 28 | GCAnnnnnnTGCnnnnnnnnnn_nn' |
| 29 | GACnn_n'nnGTC |
| 30 | Gr'CG_yC |
| 31 | C'GGCC_G |
| 32 | AGT'ACT |
| 33 | AGG'CCT |
| 34 | T'CCnGG_A |
| 35 | GACCGAnnnnnnnnnn_nn |
| 36 | G'TCGA_C |
| 37 | ACnnnnGTAyCnnnnnnn_nnnnn' |
| 38 | AAGnnnnnCTTnnnnnnnn_nnnnn' |
| 39 | GrTACnnnnGTnnnnnnnnnn_nnnnn |
| 40 | T'CTAG_A |
| 41 | CACCTGCnnnn'nnnn_ |
| 42 | CGTCTCn'nnnn_ |
| 43 | GAT'ATC |
| 44 | CTGAAGnnnnnnnnnnnnnnn_nn' |
| 45 | CC'TCA_GC |
| 46 | GAGGAGnnnnnnnn_nn' |
| 47 | CGTCTCn'nnnn_ |
| 48 | CC'TnA_GG |
| 49 | TGAnnnnnnnTCAnnnnnnnnnn_nn' |
| 50 | GrTACnnnnGTnnnnnnnnnn_nnnnn' |
| 51 | ACnnnnGTAyCnnnnnnn_nnnnn' |
| 52 | TGAnnnnnnnTCAnnnnnnnnnn_nn' |
| 53 | CC'TCA_GC |

TABLE 3-continued

| Seq. ID No. | Sequence |
|---|---|
| 54 | GAT'ATC |
| 55 | GTA'TAC |
| 56 | CCAnnnn_n'nnnnTGG |
| 57 | rG'GnC_Cy |
| 58 | CTGAAGnnnnnnnnnnnnnnn_nn' |
| 59 | T'CCnCG_A |
| 60 | T'CTAG_A |
| 61 | T'GTAC_A |
| 62 | G_AGCT'C |
| 63 | G_rGCy'C |
| 64 | GAG'CTC |
| 65 | CACCTGCnnnn'nnnn_ |
| 66 | G_CATG'C |
| 67 | r_CATG'y |
| 68 | TGC'GCA |
| 69 | Cy'CG_rG |
| 70 | C'TCGA_G |
| 71 | C'yCGr_G |
| 72 | AAGnnnnnCTTnnnnnnnn_nnnnn' |
| 73 | G_kGCm'C |
| 74 | A_TGCA'T |
| 75 | Caynn'nnrTG |
| 76 | G_rGCy'C |
| 77 | y'CCGG_r |
| 78 | AGG'CCT |
| 79 | TTA_AT'TAA |
| 80 | G_kGCm'C |
| 81 | r_GCAn_nnn'nTGC |
| 82 | r_CATG'y |
| 83 | A_TGCA'T |
| 84 | CAynn'nnrTG |
| 85 | GGATCnnnn'n_-dam methylated |
| 86 | G'GTnAC_C |
| 87 | GTT'AAC |
| 88 | C'CATG_G |
| 89 | GCTCTTCn'nnn_ |
| 90 | y'CCGG_r |
| 91 | C'CATG_G |

2. Vector Types

The four major types of vectors are plasmids, viral vectors, cosmids, and artificial chromosomes. Common to all engineered vectors are an origin of replication, a multi-cloning site, and a selectable marker. Any of these are suitable for use herein.

The sequence codes for the molecule of interest can be inserted into a clone, vector, shuttle, plasmid, BAC, or can also be integrated into the bacterial genome.

The copy number of the plasmid can be between 5-500 copy numbers per cell.

Exemplary plasmids and expression vectors include but are not limited to:

p252, p256, p353-2 (Leer et al. 1992), p8014-2, pA1, pACYC, pAJ01, pA1-derived (Vujcic & Topisirovic 1993), pall, pAM-beta1,2,3,5,8 (simon and chopin 1988), pAR1411, pBG10, pBK, pBM02, pBR322, pBR328, pBS-slpGFP, pC194 (McKenzie et al. 1986, 1987; Horinouchi & Weisblum 1982b), PC194/PUB110, pC30i1, pC30i1 (Skaugen 1989), pCD034-1, pCD034-2, pCD256, pCI2000, pCI305, pCI528, pCIS3, pCL2.1, pCT1138, pD125, pE194, pE194/PLS1, pEGFP-C1, pEH, pF8801, pFG2, pFK-series, pGK-series, pGK12, pGK13, pIA, pIAV1,5,6,7,9, pIL.CatT, pIL252/3, pIL253, pIL7, pISA (low for $e.\ coli$), pJW563, pKRV3, pLAB1000 (Josson et al. 1990), pLB4 (Bates & Gilbert 1989, pLBS, pLE16, pLEB124, pLEB590, pLEB591, pLEB600, pLEB604, pLEP24Mcop, pLJ1 (Taki-guchi et al. 1989), pLKS, pLTK2, pWCFS101 and pMD5057 (Bates & Gilbert, 1989; Skaugen, 1989; Leer et al., 1992; Vujcic & Topisirovic, 1993; Eguchi et al., 2000; Kaneko et al., 2000; Danielsen, 2002; Daming et al., 2003; de las Rivas et al., 2004; van Kranenburg et al., 2005), pLP1/18/30, pLP18, pLP317, pLP317cop, pLP3537, pLP3537xy1, pLP402, pLP825, pLP825 and pLPE323, pLP82H, pLPC37, pLPE23M, pLPE323, pLPE350, pLPI (Bouia et al. 1989), pLS1, pLS1 and pE194 (Lacks et al. 1986; Horinouchi & Weisblum 1982a), plu1631, pLUL631 from $L.\ reuteri$ carrying an erythromycin-resistance gene, pM3, pM4, pMD5057, pMG36e, pND324, pNZ-series, pPSC series, pSH71 (de vos, 1987), pSIP-series, pSK11L, pSL2, PSN2, pSN2 (Khan & Novick 1982), pT181 (Koepsel et al. 1987), (Khan & Novick 1983), pT181, pC194 and pE194 are not functional in $B.\ subtilis$ (Gruss et al. 1987), pT181, pE194/pLS1, pC194/pUB110 and pSN2 (Khan, 2005), pTL, pTRK family, pTRT family, pTUAT35, pUB110 and pC194 (McKenzie et al. 1986, 1987; Horin-ouchi & Weisblum 1982b), pUCL22, pULP8/9, pVS40, pWC1, pWCFS101, pWV02, pWV04, pWV05, RepA, system BetL.

In one embodiment, the lactose phosphotransferase system, optionally linked to the $E.\ coli$ bacteriophage T7 promoter; the $L.\ lactis$ nisA promoter system; vectors comprising promoters regulated by environmental conditions, such as for example the P170 promoter that is only active at low pH. Another exemplary vector is a cosmid, a hybrid plasmid (often used as a cloning vector) that contains a Lambda phage cos sequence. (cos sites+plasmid=cosmid). DNA sequences are originally from the lambda phage, and cosmids can be used to build genomic libraries. Another example is a bacterial artificial chromosome (BAC), which is a DNA construct, based on a functional fertility plasmid (or F-plasmid), used for transforming and cloning in bacteria, usually $E.\ coli$. Suitable vectors can be chosen or constructed, containing appropriate regulatory sequences, including promoter sequences, terminator fragments, poly-adenylation sequences, enhancer sequences, marker genes and other sequences as appropriate. Appropriate bacterial expression vectors are known to the person skilled in the art as described in Nouaille S. et al., $Genetics\ and\ Molecular\ Research,$ 2:102-111 (2003), and in Maniatis, Sambrook and Fritsch, 1982. Molecular Cloning: A Laboratory Manual, 3. Expression and Improving Expression Techniques The term heterologous expression means that a protein, or gene of interest, is experimentally put into a cell that does not normally make (i.e., express) that protein e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under-expressed or not expressed at all. Also, the nucleic acid is typically recombinantly produced, can have two or more sequences from unrelated genes arranged to make a new functional nucleic acid, e.g., a promoter from one source and a coding region to a molecule of interest, from another source.

The nucleic acid, generated recombinantly or synthetically, with a series of specified nucleic acid elements that permit transcription of a particular nucleic acid in a host cell is called an "expression cassette". The expression cassette can be part of a plasmid, virus, or nucleic acid fragment. Typically, the expression vector includes a nucleic acid to be transcribed operably linked to a promoter.

Moreover, expression cassettes can include a variety of components to regulate expression and localization of the compound of interest of the invention. For example, expression cassettes can include promoter elements, sequences encoding signal sequences, a coding sequence for the compounds of interest, terminators and anchor sequences.

Promoters—Expression of the heterologous compound of interest can be constitutive or inducible. The promoter to be used can be, for example, inducible $lactobacillus$ lac promoter, LdhL, Slp, ernB, orfX, or artificially constitutive (Rud I. et al., $Microbiology,$ 152:1011-92 (2006).

Examples of promoters are listed in the table of the modular construction, and for example can be, but not limited to: $P_{59}$ (van der Vossen et al., $Appl.\ Environ.\ Microbiol.$ 58:3142-3149 (1992)), $P_{23}$ (Elliot et al., $Cell$ 36:211-219 (1984)) promoters), $Lactobacillus\ casei$ L(+)-lactate dehydrogenase promoter (Pouwels et al., 1993, Genetics of lactobacilli: plasmids and gene expression, Antonie van Leeuwenhoek 64:85-107), Promoter of $Bacillus$ amylase (Weickert et al., $J.\ Bacteriol.$ 171:3656-66 (1989)) or xylose (Kim et al. $Gene$ 181:71-76 (1996)) promoters as well as the $Lactococcus\ nisin$ promoter (Eichenbaum et al., $Appl.\ Environ.\ Microbiol.$ 64:2763-2769 (1998)) can be used to drive inducible expression. Additional promoters can be: p32 promoter which controls expression of $Lactococcus\ lactis$ fructose-1,6-diphosphate aldolase (Van de Guchte et al., 1990, Appl. Environ. Microbiol. 56:2606-2611), T7 gene 10 promoter (Wells et al, 1993, Mol. Microbiol. 8:1155-1162), alpha amylase promoter sequence of $Lactobacillus$ amylo-virus (Pouwels et al., 1993, Genetics of lactobacilli; plasmids and gene expression, Antonie van Leeuwenhoek 64:85-107), and promoters which control expression of: LdhL, Slp, ermB, orfX, p6 (pLA6), pLT71, T7, p11, lacTp, dltp, ccpAp, plp, and inducible $lactobacillus$ as lac promoter, LdhL, Slp, ernB, orfX, as shown by Kim J H, and Mills D A. $Plasmid.$ 58:275-83 (2007).

Several recombinant techniques to improve expression, or cloning and expression of elements are known, including molecular biology methods, nucleic acid and clone construction, mutagenesis, sequencing, introduction of DNA into cells, and analysis of proteins, are described in detail in Current Protocols in Molecular Biology, Ausubel et al. eds., John Wiley & Sons, 1992, and in Molecular Cloning: a Laboratory Manual: 2nd edition, Sambrook et al., 1989, Cold Spring Harbor Laboratory Press Also, it is possible to configure the number of promoters and their length, for better expression (Yagur-Kroll S. et al., *Bioeng Bugs*, 2010 1:151-3 (2010).

The mechanism of replication of the replicon can be of RCR mechanism or by theta-replicating plasmids. The resistance gene can be based on, but not limited to: antibiotics, bacterium marker, heat-shock, or sugar utilization abilities, such as: thymidylate synthase (thyA), lactose phosphotransferase (lacF), phosph-beta-galactosidase (lac G), or alanine recemase (alr). Terminator can be added at different positions to provide more efficient expression. A variety of signal and anchor sequences are known to direct expression of polypeptides to the membrane, extracellular space or the cell wall (e.g., by covalent attachment to peptidoglycan).

In addition to comprising the desired gene, the microorganism may also be manipulated to encode other sequence elements which facilitate production of the desired expression of the molecule of interest by the bacterium. Such sequence elements include, but are not limited to, promoter/regulatory sequences which facilitate constitutive or inducible expression of the protein or which facilitate overexpression of the protein in the bacterium. Additional sequence elements may also include those that facilitate secretion of the protein from the bacterium, accumulation of the protein within the bacterium, and/or programmed lysis of the bacterium in order to release the protein from the same. Many of the sequence elements referred to above are known to those skilled in the art (Maniatis, Sambrook and Fritsch. 1982. Molecular Cloning: A Laboratory Manual).

4. Expression of Insert and Validation

Expression of heterologous genes is widely used in biotechnology, especially in industrial food fermentation, contributing to flavor, texture and preservation.

Sequences can be inserted in the vector by de-novo sequencing or by PCR amplification. de-novo synthesized is done by the Capillary Electrophoresis method, or based on Sanger sequencing techniques (Sanger et al. (1974)), when the DNA sequence is copied with high fidelity because at each base on the DNA template, DNA polymerase incorporates only the nucleotide that is complementary to that base. Thymine (T) is complementary to adenine (A) and guanine (G) is complementary to cytosine (C) because they can form hydrogen bonds with each other.

The sequence of the cloned genes and synthetic sequences can be verified after cloning using, e.g., the chain termination method for sequencing double-stranded templates of Wallace et al., *Gene* 16:21-26 (1981).

Appropriate primers and probes for identifying the genes encoding for the compounds of interest of the invention can be derived from the sequences described in the art. For a general overview of PCR, see, Innis et al., *PCR Protocols: A Guide to Methods and Applications*, Academic Press, San Diego (1990).

The concentration of molecule of interest expressed in the host bacteria can be varied from 0.1 mM to 100 mM. This concentration can be controlled by various parameters, such as: the concentration of bacteria, the copy number of the plasmid, the activity of the promoter, and the kinetics of the molecule of interest.

Known sequences of compounds of interest can be identified in commercially available databases, as described in more detail herein.

Exemplary sequences of molecules of interest within the vector are those with genes coding for molecules screening UV. In particular, genes coding for molecules screening UV in the range of 100-500 nm are contemplated. Sequences for molecules of interest within the vector are those with genes coding for molecules reducing oxidative stress, such as genes coding for molecules reducing oxidative stress caused by UV; anti-Oxidants, anti-reactive oxygen species (Anti-ROS). Sequences coding for the genes of interest may be scyA-F, from Cyanobacteria sp. Sun screen compounds, such as shinorine, can be obtained from corals (*Stylophora pistallata*), fish (*Scarus schlegeli* and *Chlorurus sordidus*), algea (*Porphyra umbilicalis*), microalgea and, bacteria, as from *cyanobacterium Nostoc* spp., (like as *Nostoc flagelliforme* or *Nostoc* sp. PCC 7524) *Lyngbya* spp., *Anabaena* spp., and *Nodularia* spp. *Nostoc punctiforme* PCC 73102 *Anabaena* sp., *Anabaena variabilis*, *Anabaena cylindrica* PCC 7122, *Cyanothece* sp. PCC 7424, *Cyanothece* sp. PCC 8802, *Rivularia* sp. PCC 7116, *Chroococcidiopsis thermalis* PCC 7203, *Cylindrospermum stagnate* PCC 7417, *Stanieria cyanosphaera* PCC 7437, *Crinalium epipsammum* PCC 9333, *Crinalium epipsammum* PCC 9333, *Anabaena* sp. 90 chromosome chANA01, *Gloeocapsa* sp. PCC 7428, *Chlorogloeopsis fritschii*, *Trichodesmium erythraeum* IMS101, *Microcystis aeruginosa* PCC 7806, *Microcystis aeruginosa* strain UV027, *Planktothrix rubescens* NIVA-CYA 98, *Microcystis* sp. NIVA-CYA 172/5, *Nostoc* sp. GSV224, or *Oscillatoria nigro-viridis* PCC 7112.

In one embodiment, the sequence for expression of the compound of interest incorporates into the genome of the bacteria.

The copy number of the plasmid can be between 5-500 copy numbers per cell. The promoters can be constitutive or inducible.

In one embodiment, it is possible to add to the vector DNA and amino acid elements like His-tag to allow purification of the molecule of interest. It is also possible to add an element like usp45, which allows exerting the molecule of interest out of the membrane.

In one embodiment, codon usage can be improved to better express the molecule of interest. Also GC % of the expression vector can be changed and/or reduced.

In one embodiment, the vector includes a limiting factor, or in another embodiment, a limiting factor is incorporated into the bacterial genome via homologous recombination.

5. Transformation

With regard to transformation techniques, appropriate bacterial host strains are selected for, e.g. their transformation ability, ability for heterologous protein expression. The bacterial host will be rendered competent for transformation using standard techniques, such as the rubidium chloride method or electroporation (Maniatis, Sambrook and Fritsch. 1982. Molecular Cloning: A Laboratory Manual).

Particular methods for the transformation of LAB strains are provided in the experimental part hereinafter, but are illustrative of techniques known in the art, and are not intended to be limiting.

Transformation of *Lactococcus lactis* by electroporation can be performed by modifying standard methods as described in, e.g., Luchansky et al. (*J. Dairy Sci.* 74: 3293-3302 (1991). Briefly, freshly inoculated *Lactobacillus* spp. are cultured in MRS broth (e.g., to 0.4-0.8 at $OD_{600}$ at 37° C. and 5% $CO_2$). The bacterial cells are harvested, washed and re-suspended in a cold (e.g., 4° C.) solution of sucrose and MgCl₂. Competent cells are then mixed with DNA and placed in a chilled gap cuvette and electroporated. Afterward, cells are allowed to recover in pre-warmed broth (e.g., for about two hours at 37° C.), prior to being plated on selective agar plate containing an antibiotic other selective agent.

Optimization of electroporation in *lactobacillus*: To support cloning and heterologous protein expression in these vaginal *lactobacillus* strains, electroporation methods were developed for application to skin bacteria. Various parameters, including culture media, cell growth stages, DNA concentration, wash or electroporation buffer composition, cuvette gap size, and voltage were evaluated to determine conditions that improved transformation frequencies for the WT *lactobacillus* strains in our collection. *E. coli*-derived plasmids were transformed into *Lactobacillus* strains by electroporation according to Luchansky et al. (*J. Dairy Sci.* 74:3293-302 (1991)) with modifications. Briefly, freshly inoculated *Lactobacillus* strain were cultured in MRS broth to 0.6-0.7 at $OD_{600}$ at 37° C. and 5% $CO_2$. The bacterial cells were harvested, washed and re-suspended in 952 mM sucrose and 3.5 mM $MgCl_2$ at 4° C. Using a pre-chilled 0.2 cm gap cuvette, competent cells were added with 1~2 μg of plasmid DNA) and electroporated immediately at 2.5 kV/cm and 200 ohms. Afterward, cells were allowed to recover in pre-warmed MRS broth for two hours at 37° C., prior to being plated on selective MRS agar plate containing antibiotic, as 20 μg/ml erythromycin.

6. Harvesting

Genetic manipulations allows over production, in different cell lines, of various expressed heterologous desired protein. Over expression, recovering the biological recombinant molecule from the skin bacteria, and harvesting a desired molecule, is the essence of the biotechnology industry, and is known to the person skill in the art (Eugene Russo, Nature, 421 456-457 (2003).

The extracted molecule from the bacteria will be used for dermatological benefits, as for UV protection.

The harvesting procedure may include mechanical, as bead-beating the bacterial cells, or chemically breaking them, by using lysozyme.

Isolation of the expressed molecule can be at various cleaning levels, as from 5%-90%, and can be used by molecular and chemical techniques, e.g. HPLC, HIS-tag, and known to the person skill in the art.

The concentration of the harvested compound can be 1-50% of the biomass before extraction.

Various compounds including bacterial cells and/or particles of the bacterial cells may be dissolved or suspended in the extracts. The final extract may include lipoproteins, lipopeptides, peptidoglycans, lipooligosaccharides, lipoteichoic acids, and teichoic acids. During the lysis process, molecules in the bacterial cells, may become chemically modified. Variose parameters, as pH, starting volume and temperature, may be range to increase yield of harvesting.

D. Exemplary Topical Compositions

The transformed, non-pathogenic populations of bacteria are formulated for topical application to the skin of a subject. Without intending to be limiting, but for purposes of exemplary embodiments, it is contemplated that the formulation may be a gel, ointment, lotion, emulsion, cream, foam, mousse, liquid, spray, suspension, dispersion or aerosol. The formulation includes one or more excipients to provide the desired form and a desired viscosity, flow or other physical or chemical characteristics for effective application, coverage and adhesion to the skin.

Excipients in the formulation are selected based on the type of formulation intended. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars, and starches.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", 4$^{th}$ Ed., a Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components. Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal. In one embodiment, a concentration of a preservative that is effective to prevent fungal growth is selected, without affecting the effectiveness of the composition for its intended purposed upon topical application.

Penetration enhancers are frequently used to promote transdermal delivery of drugs across the skin, in particular across the stratum corneum. Some penetration enhancers cause dermal irritation, dermal toxicity and dermal allergies. However, the more commonly used ones include urea, (carbonyldiamide), imidurea, N, N-diethylformamide, N-methyl-2-pyrrolidine, 1-dodecal-azacycloheptane-2-one, calcium thioglycate, 2-pyyrolidine, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly (10)oxyethylene ether), and BRIJ® 721 (stearyl poly (21) oxyethylene ether) (ICI Americas Inc. Corp.).

The microorganisms may be delivered in effective amounts per unit dose, (or per cm$^2$), of at least $10^2$ colony forming units (cfu) to $10^{20}$ cfu per cm$^2$, in particular between $10^5$ cfu to $10^{12}$ cfu per cm$^2$. In accordance with the method as described in Balskus, et al. (Science 2010) UV elements are produced to at least 0.5 mM to 1 mM for $10^6$ cfu. Based thereon, the skilled person in the art can calculate the range of produced element at any other dose of cfu.

The biological compositions may further include one or more beneficial compounds in the formulation, for example, UV protection and chemically (or biologically produced) may include added vitamin A.

The compositions can be prepared by any known or otherwise effective method for formulating or manufacturing the selected product form. In one embodiment, the composition is formulated for application to a skin epidermal surface of a subject, intending to exclude mucosal surfaces, such as nasal, vaginal, rectal, oral surfaces. In one embodiment, topical application excludes the oral cavity, as well as other mucosal surfaces of the body.

The composition can be formulated to comprise the transformed bacterial at a particular concentration to yield a desired concentration of the compound of interest. For example, the composition can comprise an amount of transformed bacterial such that the microorganisms may be delivered in effective amounts per unit dose, (or per cm$^2$), of at least about $10^2$ colony forming units (cfu) to about $10^{20}$ cfu per cm$^2$, in particular between about $10^2$ cfu to about $10^{20}$ cfu per cm$^2$. The composition may be formulated with the transformed bacteria in a proportion of at least about 0.0001% (expressed by dry weight), in particular in a proportion of from about 0.0001% to about 99%, and more particularly in a proportion of from about 0.001% to about 90% by weight, in particular from about 0.01% to about 80% by weight, and especially from about 0.1% to about 70% by weight, relative to the total weight of the composition. In general, a composition intended to be administered topically, may comprise, for living microorganisms, from about 10 to about $10^{15}$ cfu/g, in particular from about $10^5$ to about $10^{15}$ cfu/g, and more particularly from about $10^7$ to about $10^{12}$ cfu/g of microorganisms per gram of carrier, or at equivalent doses calculated for inactive or dead microorganisms or for bacterial fractions or for metabolites produced. In one embodiment, the compositions that have to be administered topically, the concentration of each bacterial strain and/or corresponding fraction and/or metabolite can be adjusted so as to correspond to doses (expressed as bacterial equivalent) ranging from about $5\times10^5$ to about $10^{15}$ cfu/d, and in particular from about $10^7$ to about $10^{12}$ cfu/d. A composition for topical application may generally comprise from about $10^2$ to about $10^{15}$ cfu/g, in particular from about $10^5$ to about $10^{12}$ cfu/g, and more particularly from about $10^6$ to about $10^{12}$ cfu/g of bacteria. When a composition comprises compounds of interest, the contents of compounds of interest in the compositions correspond substantially to the contents capable of being produced by about $10^3$ to about $10^{15}$ cfu, in particular about $10^5$ to about $10^{12}$ cfu, and more particularly about $10^6$ to about $10^{12}$ cfu of compounds of interest per gram of carrier.

In one embodiment, a composition for topical application to the skin for UV protection is contemplated. Photoaging is the alteration in the structure, function and appearance of the skin as a result of prolonged or repeated exposure to ultraviolet radiation from the sun. It accounts for 90% of age associated cosmetic skin problems in both men and women, and moderate to severe photoaging signs were observed in 72% of men and 47% of women under 30 years of age. Ultraviolet radiation is light in the non-visible area of the spectrum that is of shorter wavelength and higher energy; it ranges roughly from 150 nm to 400 nm. Most of the highest energy UV radiation (UVC radiation at wavelengths less than 280 nm) is absorbed by ozone and stratospheric oxygen. UVB radiation comprised of wavelengths from 280-320 nm and UVA radiation made up of wavelengths from 320-400 nm is the two significant causes of damage in organisms. UVB is particularly harmful to organisms because its absorption by DNA creates cyclobutane pyrimidine dimers, which do damage to other DNA, lipids and proteins within the body. It is a common cause of skin cancer. UVA is particularly harmful to organisms because it penetrates deeper into the skin layers. The composition contemplated herein in one embodiment comprises one or more transformed bacteria to express one or more compounds of interest to protect from one or both of UVA and UVB. The composition can be applied to the skin in combination with existing sunscreens of either a chemical (e.g., aminobenzoic acid(PABA), avobenzone, cinoxate, dioxybenzone, ensulizole, homosalate, menthylanthranilate, meradimate, octocrylene, octyl methoxycinnamate, octisalate, octyl salicylate, oxybenzone, padimate-O, phenylbenzimidazole sulfonic acid, sulisobenzone, and minerals: titanium dioxide, trolamine salicylate, zinc oxide or physical nature.

The composition of transformed bacteria preferably expresses a compound that protects from UV absorption by the skin, and can be shinorine which a natural mycosporine-like amino acid (MAA) small molecule, absorbing UV radiation, which being synthesized by various organisms as cyanobacteria, fungi and algae. In one embodiment, the composition comprising the population of transformed bacteria is a soap or a body wash composition that is applied to the skin.

The microorganisms may be delivered in effective amounts per unit dose, (or per cm$^2$), of at least about $10^2$ colony forming units (cfu) to about $10^{20}$ cfu per cm$^2$, in particular between about $10^2$ cfu to about $10^{20}$ cfu per cm$^2$. In embodiments where the compound of interest is for UV protection, UV elements are produced to at least about 0.1 mM to about 100 mM for $10^2$-$10^{20}$ cfu. Based thereon, the skilled person in the art can calculate the range of produced element at any other dose of cfu. In the particular case of the compositions that have to be administered topically, the concentration of each bacterial strain and/or corresponding fraction and/or metabolite can be adjusted so as to correspond to doses (expressed as bacterial equivalent) ranging from about $5\times10^5$ to about $10^{15}$ cfu/d, and in particular from about $10^7$ to about $10^{12}$ cfu/d.

A composition for topical application may generally comprise from about $10^2$ to about $10^{15}$ cfu/g, in particular from about $10^5$ to about $10^{12}$ cfu/g, and more particularly from about $10^6$ to about $10^{12}$ cfu/g of bacteria.

In one embodiment—the transformed bacteria is applied to an animal's skin, such as pets; including dogs and cats—to prevent UV damage, improve odor, and address veterinarian dermatological needs.

III. Methods of Treatment

In another aspect, methods of treating or preventing disorders or conditions associated with the skin are contemplated. The compositions described above comprising one or more populations of transformed bacteria expressing one or more compounds of interest are applied to the skin in an amount effective to provide a therapeutically effective amount of the compound(s) of interest. As used herein, a therapeutically effective amount is an amount of the topical composition that when administered to a patient or subject, ameliorates, eliminates and/or inhibits the skin disorder or condition in the local region or vicinity of the application of the topical composition.

In one embodiment, a method of protecting the skin from damage due to sun exposure is provided. Methods of treatment for relief of oxidative stress caused by UV, methods of providing an anti-oxidant, an anti-reactive oxygen species (Anti-ROS)), method for providing skin moisturizing, method for promoting anti-aging, and methods for treating psoriasis, eczema, active dermatitis, acne, wound healing (including diabetic wounds or ulcers), intertrigo/diaper rush, burns, insects bites, hives, dandruff (scales), and methods for providing odor control or removal are contemplated.

IV. Packaging of the Composition

After formulation, the composition is packaged in a manner suitable for delivery and use by an end user.

In one embodiment, the composition is placed into an appropriate dispenser and shipped to the end user. Examples of final container may include a pump bottle, squeeze bottle, jar, tube, capsule or vial.

In some embodiments, the packaging is mindful of the nature of the transformed bacteria in the composition. For example, Lactococci grown via respiration survive markedly better after long time storage than fermenting cells (Gaudu et al., Antonie van Leeuwenhoek, 82:263-269 (2002)). This long time survival is probably due to the induction of cytochromes which may protect the cells from oxidative stress. The presence of intracellular glutathione, which is also protecting against oxidative stress, can also result in an improved viability of *Lactococcus lactis* upon storage (Li et al., Appl. Environ. Microbiol, 69(10):5739 (2003)). Another approach to improve the viability of Lactococci upon storage lays in the adaptation of the spray-drying process, and in the use of process aids, such as microcrystalline cellulose, carboxymethylcellulose, hydroxypropylmethylcellulose acetate succinate, or sodium alginate, which may be used to coat the bacterial particles (EP 1789529 A2). These examples for *Lactococcus* are intended to be illustrative of the types of packaging approaches that a skilled artisan can identify for any of the bacteria described herein.

In another embodiment, the bacteria in the composition are lyophilized or freeze dried, for reconstitution before or after application to the skin. In one embodiment, lyophilization or freeze drying is conducted with one or more excipients, such as glycerol or other sugar alcohols, to improve the shelf life of the transformed bacteria. In one embodiment, the lyophilized composition does not include trehalose (α-D-glucopyranosyl-1,1-α-D-glucopyranosyde).

The packaging for the composition may be in a kit form of one or more containers. For example, a single bottle, tube, container, or capsule may be divided to two equal or unequal parts wherein one part contains the bacteria, in their packing form (freeze dried/inactive, etc.), and the other part contains an activation material, which can be a liquid or a gel. The single bottle or container can be designed so that an end user can dispense with a single force applied to the container all or a portion of the contents in the two container parts, to dispense onto the skin or other surface the transformed bacteria and the activation material. The kit may also be of the form that comprises two or more containers, one container with the population(s) of transformed bacteria and the other with a formulation for admixture with the populations of transformed bacteria. In another example, two or more containers, one container with the population of transformed bacteria, the other container with natural non pathogenic skin bacteria that are not transformed, and a third container with a formulation for admixture with the populations of transformed bacteria. In another example, the two or more containers composing the single bottle had one pump connected to two separate tubes, each draining from a different chamber. The kit may also include one or more complementary products, such as soaps, body washes or moisturizing lotions with certain pH, lotions or creams containing active compounds, bacteria and limiting factors etc. In another embodiment, the complementary product is a limiting factor that will enhance the growth, activity and/or expression of the compound of interest to provide a lasting or continuous expression of the compound. The complementary product may include any compound beneficial to the activity of the original product, and enhance its activity for lasting efficacy.

Another contemplated packaging is one wherein the population of transformed bacteria is maintained as a layer on a bandage or film that is combined with a second layer of bandage/film that will allow activation of the bacteria, and that optionally may also limit reproduction/growth factors.

In another embodiment, the final product could be stored refrigerated, with the bacteria being in their active state.

In another embodiment, the bacteria is stored in a small bead of water soluble cellulose. The beads can be mixed in any solution such as sunscreen/moisturizing/body wash or soap.

V. Examples

The following example is illustrative in nature and is in no way intended to be limiting.

Example 1

*Lactococcus lactis* with the element shinorine using vector pBTOP1-shinorine1

A. Bacteria

Bacteria of the *L. lactis* strain are used. A stock solution of the strain is stored in −20° C. in 50% glycerol in GM17/M17 broth with 0.5% sugar. Bacteria are cultured in GM17 medium/M17 broth with 0.5% sugar or in MRS medium. After 16 hours of incubation, bacteria are harvested by centrifugation and 10-fold concentrated in BM9 medium at $2 \times 10^9$ bacteria/100 µl. On plate or slant, the strain will survive 2-3 weeks.

A stock preparation of the bacteria is prepared by inoculating 5 mL broth with cells from the slant. The cells are grown overnight at 30° C. Then 3 mL fully grown culture is added to 1 ml 60% glycerol and stored at −80° C.

B. Genomic Integration into the Vector pBTOP_shinorine contains the complete operon for shinorine DNA sequence (SEQ ID NO: 1,2,3,4,5,6,7,8,9,10,11, 12,13,14) and is used production of the compound of interest. Shinorine's operon was integrated in the vector using two exemplary procedures: molecular cloning procedures (Balskus et al., *Science,* 329:1653-1656 (2010)), and de-novo sequencing synthesizing of the plasmid sequences together with the shinorine operon.

B1: Molecular Cloning

The sequence of shinorine, can be obtained from several sources, such as amplification from genomic *Anabaena variabilis* ATCC 29413, de-novo sequencing according to the complete genome of *Anabaena variabilis* or *Nostoc* spp, or amplification from growth culture of *Anabaena variabilis*. In accordance with the method as described in Balskus, et al. (supra), the complete shinorine gene cluster is PCR amplified from genomic DNA of *Anabaena variabilis*, using the forward primer ava3858-start1 (with NdeI restriction site-5'-GAGATCCCATATGAGTATCG TCCAAGCAAAG-3'; SEQ ID NO: 16) and reverse primer ava3855-stop1 (with XhoI restriction site 5'-GTACCTCGAGTCATGAATT-ATTTTCCAGACAATCTTG-3' SEQ ID NO: 17). Primers are designed for ligation into pBTOP1 vector so as to encode untagged gene products. PCR reactions contained 25 µL of master mix, 2 ng of DNA template, and 17 pmoles of each primer in a total volume of 50 µL. Thermocycling is carried out in a PCR machine using the following parameters: denaturation for 1 min at 95° C., followed by 50 cycles of 30 sec at 95° C., 1 min at 50° C., 6 min at 70° C., and a final extension time of 10 min at 70° C.

Amplified fragments are digested with the restriction enzymes NdeI and XhoI for 2.5 hours at 37° C. Digests contain 2 μL water, 6 μL of NEB Buffer 4 (10×), 6 μL of BSA (10×), 40 μL of PCR product, 3 μL of NdeI (20 U/μL), and 3 μL of XhoI (20 U/μL). Restriction digests are purified directly using agarose gel electrophoresis; gel fragments are further purified using the Illustra GFX kit. The digests are ligated into linearized pBTOP1 expression vector using T4 DNA ligase. Ligations are incubated at room temperature for 2 h and contained 3 μL water, 1 μL T4 Ligase Buffer (10×), 1 μL digested vector, 3 μL digested insert DNA, and 2 μL T4 DNA Ligase (400 U/μL). 5 μL of each ligation is used to transform a single tube of the chosen bacterial strain. The identity of the resulting pBTOP1 constructs (shinorine sequence) is confirmed by sequencing of purified plasmid DNA.

B2: Sequencing

The full sequence of shinorine's operon was searched using known databases as the NCBI and identified, and set forth herein as SEQ ID NO:1,2,3,4,5,6,7,8,9,10,11,12,13,18 which can be used as a template for de-novo sequencing, to be synthesized as an insert to the plasmid, or can be synthesized within the plasmid.

C. Transformation

A vector shinorine harboring shinorine sequence (e.g. SEQ ID NO 1), or any vector constructed for the purpose of blocking UV radiation to be applied on human skin is transformed into *L. lactis* strain, according to the following protocol, including the following steps: Preparation of the bacterial cells, transformation, plasmid extraction, growth of bacteria, Spectrophotometer measurements, and storage of transformed bacteria Preparation of the Cells: briefly, 1-10 ml *L. lactis* strain from a −80° C. stock grown at 30° C. for 24 hours is inoculated. The culture is diluted by 10×, grown at 30° C., for 24 hours. The 50 mL culture is diluted by 10× and grow until OD600 is 0.2-0.3 (ca. 3 h.), Spin down cells for 20 min 6000×g, at 4° C., Wash cells with 400 μL 0.5 M sucrose, 10% glycerol (4° C.) and spin down (6000×g), Resuspend the cells in 200 μL 0.5 M sucrose, 10% glycerol, 50 mM EDTA (4° C.), keep the suspension on ice for 15 min and spin down. Wash cells with 100 mL 0.5 M sucrose, 10% glycerol (4° C.) and spin down (6000×g). Resuspend the cells in 4 ml 0.5 M sucrose, 10% glycerol (4° C.) Use 40 μL per sample (on ice), or keep the cells in small portions in −80° C., let them defreeze on ice before use.

A protocol to transform the cells via electroporation: place 10-100 μL cells in a pre-chilled electroporation cuvette with 1 μL DNA (reconstituted in TE buffer), and keep the cuvette on ice. Use a Biorad GENE PULSER® with following adjustments: 2000 V, 25F, 200Ω. Pulse (normal reading is 4.5-5 msec), add 1 ml growth medium+20 mg $MgCl_2$+2 mM $CaCl_2$. Keep the cuvette for 5 min on ice and incubate 1-1.5 h at 30° C. Plate 10 μL, 100 μl, 900 μL on M17 agar with glucose or lactose and limiting element (depends on plasmid). Incubate 1-2 days at 30° C.; and grow the bacteria in liquid for spectrophotometer analysis, and plasmid extraction.

The cells can also be transformed via heat shock.

Three samples (transformed bacteria (*L. lactis* transformed with molecule of interest inserted into vector (e.g. SEQ ID NO 15), only bacterial cells (not transformed); and bacterial strain with a designed vector without the shinorine sequence inserted are checked in a regular spectrophotometer using UV wavelengths of 270 nm, 310 nm, 330 nm, and 360 nm, every 10 min for an hour up to 10 days, or 200-400 nm every 10 min for an hour up to 10 days.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A composition comprising a population of transformed bacteria formulated for topical application to a subject, the population of transformed bacteria comprising non-pathogenic, Gram-positive bacteria that have been genetically modified to express a mycosporine-like amino acid at a level of about 0.1 mM to about 100 mM of $10^2$-$10^{20}$ cfu of the transformed bacteria.

2. The composition of claim 1 wherein the population of transformed bacteria comprises bacteria selected from the group consisting of *Lactobacillus cesei, Lactobacillus reuteri, Lactobacillus acidophilus, Lactobacillus jensenii, Bifidobacterium lognum, Bifidobacterium reuteri, Bifidobacterium lactis, Bifidobacterium breve, Bifidobacterium animalis, Propionibacterium acidipropionici, Propionibacterium freudenreichii, Propionibacterium thoenii, Propionibacterium jensenii, Lactobacillus lactis, Lactobacillus rhamnosus, Lactococcus lactis,* and *Lactococcus plantarum.*

3. The composition of claim 2 wherein the population of transformed bacteria is selected from the group consisting of transformed *Lactobacillus lactis* and *Lactococcus lactis.*

4. The composition of claim 1 wherein the transformed bacteria is present in a topical composition at a concentration of at least 0.1% by weight of the total composition.

5. The composition of claim 1 further comprising a titanium dioxide, zinc oxide, para-aminobenzoic acid, avobenzone, butyl methoxydibenzoylmethane, ensulizole, 2-phenylbenzimidazole-5-sulfonic acid, homosalate, homomethylsalicylat, meradimate, methyl 2-aminobenzoate, methylanthranilate, octinoxate, methyl 2-aminobenzoate methylanthranilate, octisalate, 2-ethylhexyl salicylate, octyl salicylate, octocrylene, 2-ethylhexyl-2-cyano-3,3diphenylacrylate, oxybenzone, benzophenone-3,2-hydroxy-4-methoxybenzophenone, sulisobenzone, benzophenone-4, drometrizoletrisiloxane, mexoryl XL, enzacamene, 4-Methylbenzylidene camphor, padimate-O, octyl dimethyl PABA, ΣPABA, terephthalylidene dicamphor sulfonic acid, mexoryl SX, 3,3'-(1,4-phenylenedimethylidene)bis[7,7-dimethyl-2-oxobicylclo[2.2.1] hept-1-yl methanesulfonic acid), cinoxate, 2-ethoxyethyl 3-(4-methoxyphenyl) propenoate, diethanolamine-methoxycinnamate, dioxybenzone, benzophenone-8, (2-hydroxy-4-methoxyphenyl) -(2-hydroxyphenyl) methanone, triethanolamine salicylate, or trolamine salicylate.

6. The composition of claim 1 further comprising a sunscreen active ingredient that absorbs UVB radiation.

7. The composition of claim 6 wherein the sunscreen active ingredient that absorbs UVB radiation is avobenzone.

8. The composition of claim 1 further comprising a sunscreen.

9. The composition of claim 8 wherein the sunscreen comprises zinc oxide.

10. The composition of claim 1 wherein the mycosporine-like amino acid is selected from the group consisting of gadusol, deoxygadusol, 4-deoxygadusol, shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, palythenic acid-337, palythenic acid-335, palythenic-serine, palythine-threonine, palythine-threonine-sulphate, palythenic-serine-sulphate, euhalothece, mycosporine-alanine, 2-(e)-2,3-dihydroxipro-1-enylimino-mycosporine-alanine, and scytonemin.

11. The composition of claim 1 wherein the population of transformed bacteria is formulated in the composition for topical application as a cream, lotion, emulsion, gel, ointment or liquid.

12. A composition comprising a population of transformed bacteria formulated for topical application to a subject, the population of transformed bacteria comprising non-pathogenic, Gram-positive bacteria selected from the group consisting of *Lactobacillus lactis* and *Lactococcus lactis* that have been genetically modified to express a mycosporine-like amino acid at a level of about 0.1 mM to about 100 mM for $10^2$-$10^{20}$ cfu of the transformed bacteria.

13. The composition of claim 12 wherein the transformed bacteria is present in a topical composition at a concentration of at least 0.1% by weight of the total composition.

14. The composition of claim 12 further comprising a sunscreen.

15. The composition of claim 12 wherein the sunscreen comprises avobenzone or zinc oxide.

16. The composition of claim 12 wherein the mycosporine-like amino acid is selected from the group consisting of gadusol, deoxygadusol, 4-deoxygadusol, shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, palythenic acid-337, palythenic acid-335, palythenic-serine, palythine-threonine, palythine-threonine-sulphate, palythenic-serine-sulphate, euhalothece, mycosporine-alanine, 2-(e)-2,3-dihydroxipro-1-enylimino-mycosporine-alanine, and scytonemin.

17. A composition comprising a sunscreen active ingredient that absorbs UVB radiation and a population of transformed bacteria formulated for topical application to a subject, the population of transformed bacteria comprising non-pathogenic, Gram-positive bacteria that have been genetically modified to express a mycosporine-like amino acid at a level of about 0.1 mM to about 100 mM for $10^2$-$10^{20}$ cfu of the transformed bacteria.

18. The composition of claim 17 wherein the transformed bacteria is present in a topical composition at a concentration of at least 0.1% by weight of the total composition.

19. The composition of claim 17 further comprising a sunscreen.

20. The composition of claim 17 wherein the mycosporine-like amino acid is selected from the group consisting of gadusol, deoxygadusol, 4-deoxygadusol, shinorine, porphyra-334, palythine, palythene, asterina-330, palythinol, mycosporine-glycine, mycosporine serinol, mycosporine-taurine, mycosporine-glycine-valine, mycosporine-2-glycine, mycosporine-glycine-glutamic acid, mycosporine-glutamic acid-glycine, mycosporine-methylamine-serine, mycosporine-methylamine-threonine, usujirene, dehydroxylusujirene, palythenic acid-337, palythenic acid-335, palythenic-serine, palythine-threonine, palythine-threonine-sulphate, palythenic-serine-sulphate, euhalothece, mycosporine-alanine, 2-(e)-2,3-dihydroxipro-1-enylimino-mycosporine-alanine, and scytonemin.

* * * * *

SEQUENCE LISTING

```
<160> NUMBER OF SEQ ID NOS: 91

<210> SEQ ID NO 1
<211> LENGTH: 6459
<212> TYPE: DNA
<213> ORGANISM: Anabaena variabilis

<400> SEQUENCE: 1
atgaattatt ttccagacaa tcttgtaaac gctgtgctaa aacctgtaca tggggttcta      60
gaacaaacga ataatggttt ccagggacat caataatctt aatttcttga gccgccatta     120
cagaaaataa ttctacccaa actaaggtcg ggtcaggagc cataatatgt ttttccctgg     180
ctcgaaatac agtgactttt cctggatatg gttgtcttat ataggaataa gttgcttta      240 aagttcccac caaaacatca agaatacggc gattattttg acgttctaca ccaggcggga     300
atattctagc gctccgtgct ttatcaatga tgtaattaat ttttcttct acagttaaat      360 tttctatttc ttcaggtgtg actagattat cttgaccaaa cataccgcca aaaactctgg     420
agagaacacc aactaaataa acgtcatcaa tgggttttttg tttatccagc agaatcggta     480
cgtaagaatc taatattgct agtaaagata cttcttgtcc ttgtctatgt aactgctgtg     540
ctacttcata agctacgact ccaccaaatg accaccccc gacacgataa ggccttggg      600
```

```
gttgaaattc tctaatagtt ttgacgtaga gactagccat atcttcaact cgcgtcaagg    660
gtgcttcatc tccataaaat ccttgagctt gtaagccata aaatggttgg tcagttccta    720
tatattgtgc gagtttaaaa tagcataaaa catgaccacc agcaggatgt atacaaaaga    780
aaggctgctg cttaccttgt ggttgaattg aactaggggg tgaattatgg atttggttgt    840
ttgcttgaat aaccttggct aaatctgcaa ttactggatt tgttaaaagt gttgctaagg    900
atatctcttt agcaaataac tcttcaattt gagaaattaa atgtagagct ttagggaat     960 taccaccaat agcgaaaaag ttttctgtca cacctacttt aggtaaatgc agaatattcg   1020
accagatttg tactaatttt tcttcaactt cattccgagg cgctacatag gaattatgtt   1080
cactataatt aaataaatca ggcttaggta atgccttacg gtctacttta ccactgggag   1140
ttaaaggaag atgctccagc atcacaaaag cggctggaat cataaaatca ggtagccttg   1200 ctttaggaa atcacgcaga ttatcaagct gaggtttgat ggagttatag gtaatataag    1260
cgatgatttg ttttctctga gcgttatcat cccgcgctat gactcagct tctctgactt    1320 gtgggtgtga agataaaaca ttttcaatct cgccaatttc aattctataa ccccgaattt   1380
ttacttgata atctgttcta ccaagatatt caatatttcc atcgggtaaa taacgagcta   1440
aatcacctgt tttataaagt cgcttaaact cagaattggg aaagggatta ataataaatt   1500
tttctttggt caattcttct ttattcaaat aaccacgagc aacccctaca ccaccaatat   1560
aaatttcacc agtgacacca atatttactg gttgtaaatc ggcatcaaga atataaattt   1620
gagtattagc aatgggacga ccaataggta cactctttaa attactatct tttctacatt   1680
gccaaaatgt gacatcaatt gctgcttctg tcgggccata gaggttatgt aattcacatt   1740
gcaaatgctg gaaaaatcta ttttgtaaat ctatagataa agcttcaccg ctacaaataa   1800 ctcttttag agagctgcat ttgcttacat ggcgattttg taaaaacact tgcagcattg    1860
aggggacaaa atgcaacgta gtgatttgtt cttgagtaat taaatcgatg aggtaagcac   1920
tatctttatg tccgcctggt ttggctatta ccaaacgtgc gccagttaat aaagtccaaa   1980
agaactccca aacggaaaca tcaaaactaa aggggttttt tgtaaaatg ctatctgtgg    2040 aatcgatttg ataagcttcc tgcatccaca ataagcgatt acagatacct ttgtgggtgt   2100
tcattgcacc ttttggttta ccagtggaac cagaggtgta aattacataa gcaagattat   2160 ccgttttttat attactttg ggattggtat tagcttgtgt ggaaatttttc tcccattccc   2220 tatctcacaca gatagtttgt gcttgatggt ggggaatttg attgagtaat ttttcttgag   2280
ttagtagtac cttcacctga gaatcttcta gcatataagc tatgcgttct tgaggatatt   2340
cagggtcaat aggaacataa gcaccccag ctttgaggat tcctaaaaga cagataacca    2400
tttctaagga acgttctaaa caaacgccta ccagggtttc tggctggact cctaatgttt   2460
gtaaataatg tcctagctgg tttgctttat gatttagttc ttgataagtt agttgttgct   2520
tgtcaaaggt gacagcgatc gcctcaggtg ttcgttctac ttgagctaca attagttcat   2580
gtaaactctg ggaagatca taatctctgt gggtcgcgtt ccactctaca agtaacttac    2640
gaatattaaa atctatagtc tgcatatctt ctaactttgc tcaataataa aaaatttctc   2700
acgcagagac gcagagaaaa cacactccgc gtccctctct cttgaaaagt ttcctacgga   2760
gggaaaccct cctccagaac ttttcgctgc gctaacctca gcgtccctct gcgtttaaaa   2820
actaatctcc ccccaattcc accaacttcc caatattgaa atctatccgc gtccaacctt   2880
taagacgacg caaattattc aataacagta ggggaatttg ccaatgatgt accatcaaaa   2940
```

```
acggtaaggg gtcatctggc tgataaatcg catcagtccc gcgccaaata ttccccagcc    3000
atctttgcaa ctgggtgaaa gaacggatac cagttaaacg ccaaacttcg tgataagtcc    3060
aataggtagg cttgcttgtc gttagtggtt gtatggtttc agtcgtcggt gcttgactca    3120
agtacgcttc tgctacctgg gggtggtcgt aaaatgtggt aattgctgaa tgtgtgcggg    3180
ggttacactc gatggcgtaa actgttccgt cttcggcttg ataaagtca aggaaatct    3240 gtcctgtcag tttcagttcc ttgacaaaat gctgtaccca ttcggtaatt tgcgggttat    3300
ttacattctc ataattaact tggaaggctg aagattcgca acagcaatgc agtctgagtt    3360
ccccattccg aacggtgcta tgggtgcaga attccttacc ggggataaat tcctgcataa    3420
tccacggttt ttcgggagta attggcaaac ttctgacgaa tgctgctgtt tcctctggag    3480
tagcacaggg gagtttggtt aagtccaacc gccgcactga gtcgtaggga atgcttttga    3540
ggatgtattt acgtgtctct ccagaaaaat cgaagttgat gacttgttct ggtgaggtaa    3600
ttttaaagga tttgggtact gataaaccaa gcgatcgcgc tttttgtgtc aacgcaaatt    3660
tatcatccaa catttgggta atatctgcgt caaagtgaaa cacttcgcaa taatgggata    3720
actctggttt ggctaatgag tcgtagtagc tacccactgg actggtgacg ggaatataaa    3780
catcgatgtt ttcttgtttg acgatatcta ccaaagcctg aatgtaagct tggggattgt    3840
cctggggtgc ggggactgtg taaaacttat ccactgcttg ggaaaaacga tgaccagtca    3900
accagtattt atgggtttcc accaagacaa ctctatgtcc agccgcgtgg aatgaccttg    3960
ctagttgtaa agctttggtc atcttaccgc cactgataag aatggtttgg gggtttgctg    4020 cttttgacctt ttgcggtcgg aagactaaca aggatataaa aacaatggtg gcattaatgg    4080
gcaatgctag taataacaaa gccaaagtgc agatattttg gataattgcg gctattttcg    4140
tctgggaagg aagagacggt gtagcaggtg cggaagaaag gggaagggat tgtgccatag    4200
tcgattggac aattaaggtt gtattctgcg gataattgtt aaaccatctc gcaacggcaa    4260
caaaacctgt tctacacggg ggtctatagc tactgtatga ttaaattgcg cgatcgcttc    4320
accattgacg ctacgttcct ctgctggtag ataaacttcc ccttgtaata aggtgttatc    4380
tacacaaata aagccatctg gtgctaacaa actgctacct agcaacttgt gaaaataggc    4440
tacatactct tttttatctg cgtcgataaa taccaagtca aaagactccc cagcttctgc    4500
taacttatca agagttgcta aggctgcatc caattccaca cgaatctttc accgtgggg    4560 agattgttga aaggctttct gtccaatttc cgccgcgtaa gggtcaactt cacaagccac    4620
aagcagtcca tcctctggta atgcttccgc catcgccagc gccgaataac cggtaaacat    4680
cccaatttct aagactttt tagctttggt catgtgaaca aacatcttta aggtttgtcc    4740
ttcgatatga ccagaaagca tctcttgttc tagaggacgg acggttgtac ctccgtggaa    4800
gtgttctccc caggcttcgg tggctgtggt ttttgccaat gcagcgagtt caggagattc    4860
tggagtggtg cattcttcca aataagggtc tatacctgcg gctaaacgcc aagcctgatg    4920
gatgtttgct atcaattccc caggtaaatc tggatgttgc ttaacctctt ggactatggc    4980
ttctaactgc ttggttaaaa ttcccaatgg tgtaacaggt ctagctgttg gttggacaat    5040
cacatttgtc aagtcgcttc gctccaattc aaaattcaaa attcaaaatt caaaattaaa    5100
gacaattagt gtccgattat ttgcgtagcc ttctctttcc ctacgggacg ctccgcgaac    5160
agaaatgcta ccgcgctcgc gcagtgtatc cgtggagtat tttgcatttt gaattcaaaa    5220
aagtcattat ttaacactcc cgattaattc ttttgataa acgggataca catccacacc    5280
ttcaccacca cggggataac tggtacaaag ttctttgtgg tcagctaatg cggctgctaa    5340
```

-continued

```
ttcttctctt gtcaggtcat tgacgaagac acaatcacca atgggttttg gcatagcagc    5400
tcttaacaaa ccatcacgag ttaatgtgat agattcagta ccacgccaca aaatatctat    5460
atccaacatg ggatggtcga gggatagacc aacgcgactc attaatccta aaatacgatc    5520
gcgttctgca attgtaatat atcctctacg ggcggcgatc gttgccgaga aagccatatc    5580
tacattaacg gcgtgtccgt ggaacatggg tagacgaggc gcaagttcca aggtgggact    5640
ccaagtgtga ccgtaagcaa tcaccctatc taggtctaac tcatgcaggt tgggaacttc    5700
caattccaac atcttatgga tagctttgta agtcaaacga tgggctattt ctttaatctc    5760
tggagttgca tctatattgc caaaatgagt acgtagtaat tcttcgccgt acttctccaa    5820
caattcaaaa acttcttgat gcgctactac agcgattttt accaattccg ccatcccgtt    5880
acgtacttgg tctgtaggga gagtacgcaa caaggagaaa tctaaaaata ctttgcgaga    5940
agcatgataa gcacccaaac ggttttcag tttgcgatga ttaactgcta ccttaattgc     6000
tacactggca tcaattaatc caatcaatgt agtaggaatg cggatgtaat tgctgctgcg    6060
acgatatgta gaacaagcaa agccgacaac atctgtaatt aaaccgccac ccacgactaa    6120
tactggttct ttgcggacta atttgaaatc tgcaaagaca tctataactc tctcgaaagt    6180
ttgaatagtc ttatctggtt cagtaatggt aataggaaat agcctcagtt ctataccata    6240
atactggaaa tatgcctgaa tttgattacc atacaaccga ctgacgttag catctacaat    6300
cgccaagcat cgtccaaaac cttgatatac atctgctagt gcagaattct ggatttcaaa    6360
aataccatct acatacacca aatcatactc aatctttttcg taaccttcta catgaaaaga    6420
tgtttcctta gcttcaaact ttgcttggac gatactcat                          6459
```

<210> SEQ ID NO 2
<211> LENGTH: 7210
<212> TYPE: DNA
<213> ORGANISM: Nostoc sp.

<400> SEQUENCE: 2

```
cttttaaaca ttctgctaaa acctgtacat gaggttctaa acaaacgaa taatgatttc      60 ctggcacatc aataatatta atttcctctg ctgccattac agaaaataac tccacccaaa    120
ctaaagtggg atcaggagcc ataatatgtt tctccctagc tctaaaaatt gttacttttc    180
caggatatgg ctgtcttta taggaataag ttgcttttaa agttcccacc aatacatcta    240
aaatgcggcg attattttga cgttccacac caggaggaaa aattttcgct tttctggctt    300
tgtcaatgat ataattaatt ttttcttcta aacttaaatg ctggatttct tctggtgtaa    360
ctaaattatc ttgaccaaac attccccga agactctaga agtacacccc acgagataaa    420
catcatcaat ttgttttttgt ttatctaata aaatgggtac gtaagaatca agtatggcta    480
acaaagatac ttcttgtcct tgctttatta gctgctgtgc tacctcataa gcaaccactc    540
ccccaaacga ccaaccccct aattgataag gcccttgggg ttgaaattct ctgatagttt    600
tcacatagag gctggccata tcttcaactt tagttaaagg ttcctctttc ccataaaaac    660
cctgagcttg caaaccataa aacggttgtt cattgcccat gttatgggct aatttgaagt    720
aacataaaac atgaccaccg gcaggatgta tacaaaagaa aggttgcttc ttaccttgtg    780
gctgaatggg aactaaagga gaattctgaa tcagattact ggaatcttga ataactgctg    840
ctaaatctgt aattactggg ttcttttaata gtgttgctag agggattttct tttccaaaat    900 cttgttcaat tttagagatt aaatgtagtg ctttaagtga atttccacct aacgcgaaaa    960
```

```
agttatcttt tactcctatt tgtggtaaat ttaggatgtc tgaccaaatt tttactaatt    1020
gtgcttctac ttgattacga ggagcgacaa aatcattaat ttcaatgaaa tgagaaatat    1080
caggttgtgg taaagcttta cggtctactt ttccactagg agttaaaggt agtgcttcca    1140
gcatgacaaa agcggctgga atcataaaat caggtagctt tgctttcaaa aaatcacgta    1200
ggctgttaag tgttggtttt tctgaatcgt aggtaatgta agcaacaagt tgttttcta     1260 aattttgatg attacgcgca ataattacag cttctcgcac ttgcgaatgt aagcagagag    1320
tattttcaat ttcgccaatt tcaatccgat aacctcggat ttttacttga tagtctactc    1380
tgccaatata ttcaagattg ccatctggta aataacgagc taaatcacca gttttgtaga    1440
gacgttccga tactaatttt gattttttaa aaggattggg aataaatttt tcattagtta    1500
attctggacg attccagtaa ccacgtgcta cgccgacacc accaatatac atttcaccga    1560
tgacaccgac atctacaggc tgcaagtgtt cattaaggat gtaaatttgg gtgttagcaa    1620
tgggacgacc aattggtaca gttttaaat tactgtgctt ttgacactgc caaaaagtga    1680
catcaatagc tgcttctgta gggccgtaca ggttatataa ttcgcagtcc aaacgctcaa    1740
aaaatctatt ttgtaaatct acaggtaaag cttcaccact acaaattact ctttgaagag    1800
aagtacattt ttctatacca cgactagcta aaaacatttg cagcatggag gggacaaaat    1860
gcacagtagt gatttgctct tgaataatca gattaattaa ataattacta tctctatgtc    1920
cacccggttg agcaattact aggcgcgcgc ctgttaataa agtccaaaag aattcccaga    1980
cagagacatc aaagctaaaa ggtgtttttt gtaaatgct atctgtagaa tttatttgat    2040
aagtttcttg catccacagc aagcgattac atataccttt gtgggtgttc attgcaccct    2100
tgggtttacc agtagaacca gaagtgtaga tgcataagc aagattatct gcttttactt    2160
cactttgggg attagtcttt ggttgtgtag aaattttgtt ccattctgta tctacacaaa    2220
tagtatgtgc ttgatggtgg ggaatttgat ttagtaattt ttcttgggtt agtaatacct    2280
gaatttggga atcttctagc atataagcta tgcgttcttg gggatattct gggtcaatgg    2340
gtacataagc accaccagct ttgagaattc ccaataaaca cacaaccatt tctaaggaac    2400
gttctagaca aacaccaact aatgtttctt gttgaactcc tagtgtgtgt aaatgatgtg    2460
ctagttgatt ggctctatta tttaattctt gataggttat ttgttgctgt tcaaacttta    2520
cagctatggc gttggggtg cgttctactt gcgttgtaaa taactcatgt aaaccttgag    2580
aaaggtcgta atctctgtgt gtagcgtcgg gatttatttg tgtggttgc attttaaat     2640 cagggaaaaa tgtcggttaa tggctttgtg gaatgggggt gatttactca cccagagatg    2700
caaagacgca aaaaaaccta atcttttctt ctttgcgcct tgcgccttt gcgtgagata     2760 aaaaaaatcc ttaatctccc ccgaattcga ctaatttacc gatgttgaaa tctatccgcg    2820
tccagccttt gagttgacgg agattattta acaacaacag aggaatttgc cagtgatgta    2880
ccatcaaaaa tggtagggga tcatgtagct gtaaaattgc atctgttccg cgccaaatgt    2940
ttttcagcca tgtcttcaac tgggtgaagg aacgaatacc agtcaagcgc caaatttcgt    3000
gataagtcca ataggttggt ttgctggttg ctaatggttg taaggtttcc gccattggtt    3060
gtttaccaat gtaagcttct gcaacttggg ggtggttgta gaaggtggta atagctgagt    3120
gtgtgcgggg gttacactcg atcgcgtata cttgtccgtc ttcagtttgg atgaagtcga    3180
aggatatctg tcctgtgagt ttgagttctt tgacaaagtg tctcacccat tccaagattt    3240
gcgggttttc tatgttctca tagttgactt ggaaggctga tgattcgcaa caacagtgta    3300
gtcgaatttc tccgtcccta actgtgctgt gggtgcagaa ttctttttcct gggatgaatt    3360
```

```
cttgcataat ccacggtttt tcgggactga tgggtagttt tctgacgaag gctgctgttt    3420
cctctggggt ggcgcagggg agtttggtta agtccaaacg ccgcactgag tcgtaagcaa    3480
tgcttttgag gatgtatttg cgagtctcac gggaaaagtc gaagttgatg acttgttcgc    3540
cagaggtgat tttaaaggat ttgggtactg ataaaccaag cgatcgcgct ttctctgcca    3600
ttgcaaattt atcatccaac atttgggtga tctctgcatc aaaatgaaac acttcgcaat    3660
ggtgagataa ctctggtttg gctaaggagt cgtaataact cccgacagga ctggtaacgg    3720
gaatgtatac atcaatgttt tcccgtttga ctatatctac taaagctttg atatagtctt    3780
ctggtttttt ttgcggtgcg ggagttgtgt aaaatttatc gaccgcttgg gaaaatcgat    3840
gtcccgttaa ccaatattta tgtgtttcca gcaataccac ccgatgtcca tctgcgtgga    3900
atgaccttgc tagttgcaaa gctttggtca tttttccgcc actgatcagg atattttggg    3960
ggttgctggt ttttgtagtt tggggacgga agatagtacc caaaccaaa gctatgcaaa     4020 caataatggc gttgatgggc aatgctaata gtagcaaagc caaagtcaga atattttgga    4080
taattgcggc tattttttgtc tctaaaccta gagacggtgt agcaggtgag gagtcaaagg   4140
aaatagattg tgccatagtt tacactcggc ggataatcgt caaaccgtcg cgcaggggaa    4200
gtaaaacctg ttctacacgg atatcaaggg ctacggtacg attgaagtca gcgatcgctt    4260
gaccgttagc actgcgtttt tggggaggta aatatacctc tccttgtagg agtgtgttat    4320
caacacaaat aaagccttgc ggtgctaaca aattagtatc tagcagcatt tgcaagtaag    4380
ctgtgtactc ttttttatcg gcatcaataa ataccaagtc aaaagtttct ccagccgttg    4440
ctaatttctc caaagttgct aaagctgcac ccaattccac acgtatcttt ccaccgtggg    4500
gagattggtt aaaagccttc tgtgcaactt ccgccgcata agggtctact tcacaagcca    4560 ccaataccc atcttctggt aaagcttccg ccatcgctaa ggctgaataa cccgtgaaca     4620
tcccaatttc cagaactctt ttcgctttag tcatgtgaac aaacatcttt aaagtttgtc    4680
cttcgatatg accagaaagc atttcctgtt ctagaggacg cacagttgca ccggctgtaa    4740
aatgctcacc ccaagcctct tttacagtta tcttagcgag tgctgctaaa gcctctgatt    4800
ctggggtagt acattcctct aaataagggt caatacctgc tgctaactcc caagcttggg    4860
taatctcagc taccaaatca gcaggtaaat cttggcgttg tttaacctct cgaacaacag    4920
cttccaactt cttagttaaa attcccaagg gtgtgacagg tctagctgtc ggtatgtcta    4980
tcaaattcgt catgatttaa aggtgtagcc acataaatta gaaaattgct gattgctcaa    5040
agcctgaaag caactgaatt aagactcagc actcatcact ttcctacagc actccctaca    5100
agttccttct gactgctgag aggatacata tctacaccct caccaccacg aggatattga    5160
ctacaaagtt cctatgttc agctaaagct gcggctgatt cggcttttgt caggtcattg     5220
acgaagaaac attctccaat aggtcttggc atagcagctc tgagtaaacc atctctagtt    5280
agggtgatag actcagtagc acgccataat aactcctcat ccaacagagg atggtcgagg    5340
gctagaccta tacgactcat caatcctaaa atgcgatcgc gctcttgagt agtaatgtag    5400
cctctccgtg ctgcaatagt cgcagacaaa gccatatcaa tattgactgc gtgaccgtgg    5460
aacataggta tatgtggcgc aagttccaag gtcggactcc aagtatgacc gtaagcaatt    5520
accctatcta ggtctaattc gtggaggttg ggtacttcca actccaacat cttttttaatc   5580 gctttgtagg tcacttcatg ggctacatct ttaatttctg gcatagcgtc aatattgcca    5640
aaatgcgtat gcagtaagtc ttccccgtac ttctccaaca actcaaatac ttctttgtga    5700
```

```
gcaactacgg cgattttgac taattccgcc ataccgttac gtacttggtc agttggtaga    5760
gtccgtaaaa aggagaaatc taagaaaact tgacgagaag catgatatgc acccaaacgg    5820 ttttttcagct tcttgtggtt aactgcgacc ttgatggcaa cactagcatc aattaagcca    5880
attaatgtag taggaatacg gatataatta ctgctgcgac ggtatgcaga gcaagcaaaa    5940
ccgacaacat ctgtaatcaa gccaccacca actactaata ctggttcttt gcgaactaat    6000
ttgaaatctg caaagacatc taccactttc tcaaatgttt gaatggtctt gtttggctca    6060
gtaatagtaa tggggaaaag agtcaagtca atgccgtgat actggaaata tttttgaatt    6120
tgtgtactgt agaactgact cacattagca tctacaacag ccaagcaacg tccaaaattt    6180
ttgtagatat ctgctaattg gtgattttta atctcaaaaa ctccatctac ataaactaag    6240
tcgtactcaa ttttttcgta gccttcaatg tgaaaagctg ctgcttgcgc ttcaaacttt    6300
gcttggacga tgctcatatt cttttgacct tagtgcagta aatgactgta tgtgttgact    6360
ggaatatttg actcaagcca aaattgaata attctagtcc tagaattaaa ccgattgatt    6420
ggcataccaa ataactctaa tttctcatca agaaatagag gtaatcgctg gcagaatttg    6480
aggtaatcaa aacttgattg taaaaagcag aacgttgatt atatataacg tacagctttt    6540
taaatatagt gaatgacttg tgagtcttgg ttgaactgta agactctgca aatacgagca    6600
aactacatta agtttctact gttttgcagt gatggtacta aatgaagtcc atcatgattg    6660
atctgattgt agacagatat agtatgccag aagttagtag aaatttgctc aaaaatctta    6720
agattttctt cacgatttta aagataacat tatttgcgaa atatttgtac ataattatga    6780
gatttttcta agaaatctca taactataag ctgcaactta gtttatataa gcatcataat    6840
ttttgatctg aactgcaaac caaagaaatt agaggagagt ttgatattaa tttttatcat    6900
aagtatcagc actactaaaa accatgaatt ttaatcaaca cacagcaaat gtttccccta    6960
attctgaatc aagaacagga gtatggaagg aaaatttaca gcagattgtt gttaattaga    7020
aatacaaaaa tggagtgcta agataaagc acatctactt ttatgagcgc agcagaaatg    7080
tcattggcat tggctaaaac ttaaggcttc taccaatact tgtaacaaaa cttaactaat    7140
ttgctctcat ttttaagtta gtgacactaa tgaaagtcct aagcaatagc ggactttttg    7200
cagttgggca                                                         7210
```

<210> SEQ ID NO 3
<211> LENGTH: 888
<212> TYPE: PRT
<213> ORGANISM: Anabaena variabilis

<400> SEQUENCE: 3

Met Gln Thr Ile Asp Phe Asn Ile Arg Lys Leu Leu Val Glu Trp Asn
1               5                   10                  15

Ala Thr His Arg Asp Tyr Asp Leu Ser Gln Ser Leu His Glu Leu Ile
            20                  25                  30

Val Ala Gln Val Glu Arg Thr Pro Glu Ala Ile Ala Val Thr Phe Asp
        35                  40                  45

Lys Gln Gln Leu Thr Tyr Gln Glu Leu Asn His Lys Ala Asn Gln Leu
    50                  55                  60

Gly His Tyr Leu Gln Thr Leu Gly Val Gln Pro Glu Thr Leu Val Gly
65                  70                  75                  80

Val Cys Leu Glu Arg Ser Leu Glu Met Val Ile Cys Leu Leu Gly Ile
                85                  90                  95

Leu Lys Ala Gly Gly Ala Tyr Val Pro Ile Asp Pro Glu Tyr Pro Gln

-continued

```
                100                 105                 110
Glu Arg Ile Ala Tyr Met Leu Glu Asp Ser Gln Val Lys Val Leu Leu
        115                 120                 125

Thr Gln Glu Lys Leu Leu Asn Gln Ile Pro His His Gln Ala Gln Thr
130                 135                 140

Ile Cys Val Asp Arg Glu Trp Glu Lys Ile Ser Thr Gln Ala Asn Thr
145                 150                 155                 160

Asn Pro Lys Ser Asn Ile Lys Thr Asp Asn Leu Ala Tyr Val Ile Tyr
                165                 170                 175

Thr Ser Gly Ser Thr Gly Lys Pro Lys Gly Ala Met Asn Thr His Lys
        180                 185                 190

Gly Ile Cys Asn Arg Leu Leu Trp Met Gln Glu Ala Tyr Gln Ile Asp
        195                 200                 205

Ser Thr Asp Ser Ile Leu Gln Lys Thr Pro Phe Ser Phe Asp Val Ser
        210                 215                 220

Val Trp Glu Phe Phe Trp Thr Leu Leu Thr Gly Ala Arg Leu Val Ile
225                 230                 235                 240

Ala Lys Pro Gly Gly His Lys Asp Ser Ala Tyr Leu Ile Asp Leu Ile
                245                 250                 255

Thr Gln Glu Gln Ile Thr Thr Leu His Phe Val Pro Ser Met Leu Gln
                260                 265                 270

Val Phe Leu Gln Asn Arg His Val Ser Lys Cys Ser Ser Leu Lys Arg
        275                 280                 285

Val Ile Cys Ser Gly Glu Ala Leu Ser Ile Asp Leu Gln Asn Arg Phe
        290                 295                 300

Phe Gln His Leu Gln Cys Glu Leu His Asn Leu Tyr Gly Pro Thr Glu
305                 310                 315                 320

Ala Ala Ile Asp Val Thr Phe Trp Gln Cys Arg Lys Asp Ser Asn Leu
                325                 330                 335

Lys Ser Val Pro Ile Gly Arg Pro Ile Ala Asn Thr Gln Ile Tyr Ile
                340                 345                 350

Leu Asp Ala Asp Leu Gln Pro Val Asn Ile Gly Val Thr Gly Glu Ile
        355                 360                 365

Tyr Ile Gly Gly Val Gly Val Ala Arg Gly Tyr Leu Asn Lys Glu Glu
        370                 375                 380

Leu Thr Lys Glu Lys Phe Ile Ile Asn Pro Phe Pro Asn Ser Glu Phe
385                 390                 395                 400

Lys Arg Leu Tyr Lys Thr Gly Asp Leu Ala Arg Tyr Leu Pro Asp Gly
                405                 410                 415

Asn Ile Glu Tyr Leu Gly Arg Thr Asp Tyr Gln Val Lys Ile Arg Gly
                420                 425                 430

Tyr Arg Ile Glu Ile Gly Glu Ile Glu Asn Val Leu Ser Ser His Pro
        435                 440                 445

Gln Val Arg Glu Ala Val Val Ile Ala Arg Asp Asp Asn Ala Gln Glu
        450                 455                 460

Lys Gln Ile Ile Ala Tyr Ile Thr Tyr Asn Ser Ile Lys Pro Gln Leu
465                 470                 475                 480

Asp Asn Leu Arg Asp Phe Leu Lys Ala Arg Leu Pro Asp Phe Met Ile
                485                 490                 495

Pro Ala Ala Phe Val Met Leu Glu His Leu Pro Leu Thr Pro Ser Gly
                500                 505                 510

Lys Val Asp Arg Lys Ala Leu Pro Lys Pro Asp Leu Phe Asn Tyr Ser
        515                 520                 525
```

Glu His Asn Ser Tyr Val Ala Pro Arg Asn Glu Val Glu Glu Lys Leu
        530                 535                 540

Val Gln Ile Trp Ser Asn Ile Leu His Leu Pro Lys Val Gly Val Thr
545                 550                 555                 560

Glu Asn Phe Phe Ala Ile Gly Gly Asn Ser Leu Lys Ala Leu His Leu
                565                 570                 575

Ile Ser Gln Ile Glu Glu Leu Phe Ala Lys Glu Ile Ser Leu Ala Thr
            580                 585                 590

Leu Leu Thr Asn Pro Val Ile Ala Asp Leu Ala Lys Val Ile Gln Ala
        595                 600                 605

Asn Asn Gln Ile His Asn Ser Pro Leu Val Pro Ile Gln Pro Gln Gly
    610                 615                 620

Lys Gln Gln Pro Phe Phe Cys Ile His Pro Ala Gly Gly His Val Leu
625                 630                 635                 640

Cys Tyr Phe Lys Leu Ala Gln Tyr Ile Gly Thr Asp Gln Pro Phe Tyr
                645                 650                 655

Gly Leu Gln Ala Gln Gly Phe Tyr Gly Asp Glu Ala Pro Leu Thr Arg
            660                 665                 670

Val Glu Asp Met Ala Ser Leu Tyr Val Lys Thr Ile Arg Glu Phe Gln
        675                 680                 685

Pro Gln Gly Pro Tyr Arg Val Gly Gly Trp Ser Phe Gly Gly Val Val
    690                 695                 700

Ala Tyr Glu Val Ala Gln Gln Leu His Arg Gln Gly Gln Glu Val Ser
705                 710                 715                 720

Leu Leu Ala Ile Leu Asp Ser Tyr Val Pro Ile Leu Leu Asp Lys Gln
                725                 730                 735

Lys Pro Ile Asp Asp Val Tyr Leu Val Gly Val Leu Ser Arg Val Phe
            740                 745                 750

Gly Gly Met Phe Gly Gln Asp Asn Leu Val Thr Pro Glu Glu Ile Glu
        755                 760                 765

Asn Leu Thr Val Glu Glu Lys Ile Asn Tyr Ile Ile Asp Lys Ala Arg
    770                 775                 780

Ser Ala Arg Ile Phe Pro Pro Gly Val Glu Arg Gln Asn Asn Arg Arg
785                 790                 795                 800

Ile Leu Asp Val Leu Val Gly Thr Leu Lys Ala Thr Tyr Ser Tyr Ile
                805                 810                 815

Arg Gln Pro Tyr Pro Gly Lys Val Thr Val Phe Arg Ala Arg Glu Lys
            820                 825                 830

His Ile Met Ala Pro Asp Pro Thr Leu Val Trp Val Glu Leu Phe Ser
        835                 840                 845

Val Met Ala Ala Gln Glu Ile Lys Ile Ile Asp Val Pro Gly Asn His
    850                 855                 860

Tyr Ser Phe Val Leu Glu Pro His Val Gln Val Leu Ala Gln Arg Leu
865                 870                 875                 880

Gln Asp Cys Leu Glu Asn Asn Ser
                885

<210> SEQ ID NO 4
<211> LENGTH: 458
<212> TYPE: PRT
<213> ORGANISM: Anabaena variabilis

<400> SEQUENCE: 4

Met Ala Gln Ser Leu Pro Leu Ser Ser Ala Pro Ala Thr Pro Ser Leu

-continued

```
1               5                   10                  15
Pro Ser Gln Thr Lys Ile Ala Ile Ile Gln Asn Ile Cys Thr Leu
                20                  25                  30

Ala Leu Leu Leu Ala Leu Pro Ile Asn Ala Thr Ile Val Phe Ile
                35                  40                  45

Ser Leu Leu Val Phe Arg Pro Gln Lys Val Lys Ala Ala Asn Pro Gln
50                      55                  60

Thr Ile Leu Ile Ser Gly Gly Lys Met Thr Lys Ala Leu Gln Leu Ala
65                      70                  75                  80

Arg Ser Phe His Ala Ala Gly His Arg Val Val Leu Val Glu Thr His
                85                  90                  95

Lys Tyr Trp Leu Thr Gly His Arg Phe Ser Gln Ala Val Asp Lys Phe
                100                 105                 110

Tyr Thr Val Pro Ala Pro Gln Asp Asn Pro Gln Ala Tyr Ile Gln Ala
                115                 120                 125

Leu Val Asp Ile Val Lys Gln Glu Asn Ile Asp Val Tyr Ile Pro Val
                130                 135                 140

Thr Ser Pro Val Gly Ser Tyr Tyr Asp Ser Leu Ala Lys Pro Glu Leu
145                     150                 155                 160

Ser His Tyr Cys Glu Val Phe His Phe Asp Ala Asp Ile Thr Gln Met
                165                 170                 175

Leu Asp Asp Lys Phe Ala Leu Thr Gln Lys Ala Arg Ser Leu Gly Leu
                180                 185                 190

Ser Val Pro Lys Ser Phe Lys Ile Thr Ser Pro Glu Gln Val Ile Asn
                195                 200                 205

Phe Asp Phe Ser Gly Glu Thr Arg Lys Tyr Ile Leu Lys Ser Ile Pro
210                     215                 220

Tyr Asp Ser Val Arg Arg Leu Asp Leu Thr Lys Leu Pro Cys Ala Thr
225                     230                 235                 240

Pro Glu Glu Thr Ala Ala Phe Val Arg Ser Leu Pro Ile Thr Pro Glu
                245                 250                 255

Lys Pro Trp Ile Met Gln Glu Phe Ile Pro Gly Lys Glu Phe Cys Thr
                260                 265                 270

His Ser Thr Val Arg Asn Gly Glu Leu Arg Leu His Cys Cys Cys Glu
                275                 280                 285

Ser Ser Ala Phe Gln Val Asn Tyr Glu Asn Val Asn Asn Pro Gln Ile
                290                 295                 300

Thr Glu Trp Val Gln His Phe Val Lys Glu Leu Lys Leu Thr Gly Gln
305                     310                 315                 320

Ile Ser Phe Asp Phe Ile Gln Ala Glu Asp Gly Thr Val Tyr Ala Ile
                325                 330                 335

Glu Cys Asn Pro Arg Thr His Ser Ala Ile Thr Thr Phe Tyr Asp His
                340                 345                 350

Pro Gln Val Ala Glu Ala Tyr Leu Ser Gln Ala Pro Thr Thr Glu Thr
                355                 360                 365

Ile Gln Pro Leu Thr Thr Ser Lys Pro Thr Tyr Trp Thr Tyr His Glu
                370                 375                 380

Val Trp Arg Leu Thr Gly Ile Arg Ser Phe Thr Gln Leu Gln Arg Trp
385                     390                 395                 400

Leu Gly Asn Ile Trp Arg Gly Thr Asp Ala Ile Tyr Gln Pro Asp Asp
                405                 410                 415

Pro Leu Pro Phe Leu Met Val His His Trp Gln Ile Pro Leu Leu Leu
                420                 425                 430
```

```
Leu Asn Asn Leu Arg Arg Leu Lys Gly Trp Thr Arg Ile Asp Phe Asn
        435                 440                 445

Ile Gly Lys Leu Val Glu Leu Gly Gly Asp
    450                 455
```

<210> SEQ ID NO 5
<211> LENGTH: 279
<212> TYPE: PRT
<213> ORGANISM: Anabaena variabilis

<400> SEQUENCE: 5

```
Met Thr Asn Val Ile Val Gln Pro Thr Ala Arg Pro Val Thr Pro Leu
1               5                   10                  15

Gly Ile Leu Thr Lys Gln Leu Glu Ala Ile Val Gln Glu Val Lys Gln
            20                  25                  30

His Pro Asp Leu Pro Gly Glu Leu Ile Ala Asn Ile His Gln Ala Trp
        35                  40                  45

Arg Leu Ala Ala Gly Ile Asp Pro Tyr Leu Glu Cys Thr Thr Pro
    50                  55                  60

Glu Ser Pro Glu Leu Ala Ala Leu Ala Lys Thr Thr Ala Thr Glu Ala
65                  70                  75                  80

Trp Gly Glu His Phe His Gly Thr Thr Val Arg Pro Leu Glu Gln
                85                  90                  95

Glu Met Leu Ser Gly His Ile Glu Gly Gln Thr Leu Lys Met Phe Val
            100                 105                 110

His Met Thr Lys Ala Lys Lys Val Leu Glu Ile Gly Met Phe Thr Gly
        115                 120                 125

Tyr Ser Ala Leu Ala Met Ala Glu Ala Leu Pro Glu Asp Gly Leu Leu
    130                 135                 140

Val Ala Cys Glu Val Asp Pro Tyr Ala Ala Glu Ile Gly Gln Lys Ala
145                 150                 155                 160

Phe Gln Gln Ser Pro His Gly Gly Lys Ile Arg Val Glu Leu Asp Ala
                165                 170                 175

Ala Leu Ala Thr Leu Asp Lys Leu Ala Glu Ala Gly Glu Ser Phe Asp
            180                 185                 190

Leu Val Phe Ile Asp Ala Asp Lys Lys Glu Tyr Val Ala Tyr Phe His
        195                 200                 205

Lys Leu Leu Gly Ser Ser Leu Leu Ala Pro Asp Gly Phe Ile Cys Val
    210                 215                 220

Asp Asn Thr Leu Leu Gln Gly Glu Val Tyr Leu Pro Ala Glu Glu Arg
225                 230                 235                 240

Ser Val Asn Gly Glu Ala Ile Ala Gln Phe Asn His Thr Val Ala Ile
                245                 250                 255

Asp Pro Arg Val Glu Gln Val Leu Leu Pro Leu Arg Asp Gly Leu Thr
            260                 265                 270

Ile Ile Arg Arg Ile Gln Pro
        275
```

<210> SEQ ID NO 6
<211> LENGTH: 410
<212> TYPE: PRT
<213> ORGANISM: Anabaena variabilis

<400> SEQUENCE: 6

```
Met Ser Ile Val Gln Ala Lys Phe Glu Ala Lys Glu Thr Ser Phe His
1               5                   10                  15
```

Val Glu Gly Tyr Glu Lys Ile Glu Tyr Asp Leu Val Tyr Val Asp Gly
            20                  25                  30

Ile Phe Glu Ile Gln Asn Ser Ala Leu Ala Asp Val Tyr Gln Gly Phe
            35                  40                  45

Gly Arg Cys Leu Ala Ile Val Asp Ala Asn Val Ser Arg Leu Tyr Gly
50                  55                  60

Asn Gln Ile Gln Ala Tyr Phe Gln Tyr Gly Ile Glu Leu Arg Leu
65                  70                  75                  80

Phe Pro Ile Thr Ile Thr Glu Pro Asp Lys Thr Ile Gln Thr Phe Glu
                85                  90                  95

Arg Val Ile Asp Val Phe Ala Asp Phe Lys Leu Val Arg Lys Glu Pro
                100                 105                 110

Val Leu Val Val Gly Gly Leu Ile Thr Asp Val Val Gly Phe Ala
                115                 120                 125

Cys Ser Thr Tyr Arg Arg Ser Ser Asn Tyr Ile Arg Ile Pro Thr Thr
130                 135                 140

Leu Ile Gly Leu Ile Asp Ala Ser Val Ala Ile Lys Val Ala Val Asn
145                 150                 155                 160

His Arg Lys Leu Lys Asn Arg Leu Gly Ala Tyr His Ala Ser Arg Lys
                165                 170                 175

Val Phe Leu Asp Phe Ser Leu Leu Arg Thr Leu Pro Thr Asp Gln Val
                180                 185                 190

Arg Asn Gly Met Ala Glu Leu Val Lys Ile Ala Val Ala His Gln
                195                 200                 205

Glu Val Phe Glu Leu Leu Glu Lys Tyr Gly Glu Gly Leu Leu Arg Thr
                210                 215                 220

His Phe Gly Asn Ile Asp Ala Thr Pro Glu Ile Lys Glu Ile Ala His
225                 230                 235                 240

Arg Leu Thr Tyr Lys Ala Ile His Lys Met Leu Glu Leu Glu Val Pro
                245                 250                 255

Asn Leu His Glu Leu Asp Leu Asp Arg Val Ile Ala Tyr Gly His Thr
                260                 265                 270

Trp Ser Pro Thr Leu Glu Leu Ala Pro Arg Leu Pro Met Phe His Gly
                275                 280                 285

His Ala Val Asn Val Asp Met Ala Phe Ser Ala Thr Ile Ala Ala Arg
                290                 295                 300

Arg Gly Tyr Ile Thr Ile Ala Glu Arg Asp Arg Ile Leu Gly Leu Met
305                 310                 315                 320

Ser Arg Val Gly Leu Ser Leu Asp His Pro Met Leu Asp Ile Asp Ile
                325                 330                 335

Leu Trp Arg Gly Thr Glu Ser Ile Thr Leu Thr Arg Ala Gly Leu Leu
                340                 345                 350

Arg Ala Ala Met Pro Lys Pro Ile Gly Asp Cys Val Phe Val Asn Asp
                355                 360                 365

Leu Thr Arg Glu Glu Leu Ala Ala Leu Ala Asp His Lys Glu Leu
                370                 375                 380

Cys Thr Ser Tyr Pro Arg Gly Gly Glu Gly Val Asp Val Tyr Pro Val
385                 390                 395                 400

Tyr Gln Lys Glu Leu Ile Gly Ser Val Lys
                405                 410

<210> SEQ ID NO 7
<211> LENGTH: 1233

```
<212> TYPE: DNA
<213> ORGANISM: Anabaena variabilis

<400> SEQUENCE: 7
atgagtatcg tccaagcaaa gttttgaagct aaggaaacat cttttcatgt agaaggttac      60
gaaaagattg agtatgattt ggtgtatgta gatggtattt tgaaatcca gaattctgca      120
ctagcagatg tatatcaagg ttttggacga tgcttggcga ttgtagatgc taacgtcagt      180
cggttgtatg gtaatcaaat tcaggcatat ttccagtatt atggtataga actgaggcta      240
tttcctatta ccattactga accagataag actattcaaa cttcgagag agttatagat      300
gtctttgcag atttcaaatt agtccgcaaa gaaccagtat tagtcgtggg tggcggttta      360
attacagatg ttgtcggctt tgcttgttct acatatcgtc gcagcagcaa ttacatccgc      420
attcctacta cattgattgg attaattgat gccagtgtag caattaaggt agcagttaat      480
catcgcaaac tgaaaaaccg tttgggtgct tatcatgctt ctcgcaaagt attttagat      540
ttctccttgt tgcgtactct ccctacagac aagtacgta acgggatggc ggaattggta      600
aaaatcgctg tagtagcgca tcaagaagtt tttgaattgt tggagaagta cggcgaagaa      660
ttactacgta ctcattttgg caatatagat gcaactccag agattaaaga aatagcccat      720
cgtttgactt acaaagctat ccataagatg ttggaattgg aagttcccaa cctgcatgag      780
ttagacctag ataggatgat tgcttacggt cacacttgga gtcccacctt ggaacttgcg      840
cctcgtctac ccatgttcca cggacacgcc gttaatgtag atatggcttt ctcggcaacg      900
atcgccgccc gtagaggata tattacaatt gcagaacgcg atcgtatttt aggattaatg      960
agtcgcgttg gtctatccct cgaccatccc atgttggata tagatatttt gtggcgtggt     1020
actgaatcta tcacattaac tcgtgatggt ttgttaagag ctgctatgcc aaaacccatt     1080
ggtgattgtg tcttcgtcaa tgacctgaca agagaagaat tagcagccgc attagctgac     1140
cacaaagaac tttgtaccag ttatccccgt ggtggtgaag gtgtggatgt gtatcccgtt     1200
tatcaaaaag aattaatcgg gagtgttaaa taa                                   1233

<210> SEQ ID NO 8
<211> LENGTH: 174
<212> TYPE: DNA
<213> ORGANISM: Anabaena variabili

<400> SEQUENCE: 8
tgactttttt gaattcaaaa tgcaaaatac tccacggata cactgcgcga gcgcggtagc       60
atttctgttc gcggagcgtc ccgtagggaa agagaaggct acgcaaataa tcggacacta      120
attgtcttta attttgaatt tgaattttg aattttgaat tggagcgaag cgac             174

<210> SEQ ID NO 9
<211> LENGTH: 840
<212> TYPE: DNA
<213> ORGANISM: Anabaena variabilis

<400> SEQUENCE: 9
ttgacaaatg tgattgtcca accaacagct agacctgtta caccattggg aatttttaacc      60
aagcagttag aagccatagt ccaagaggtt aagcaacatc cagatttacc tggggaattg      120
atagcaaaca tccatcaggc ttggcgttta gccgcaggta tagacccttta tttggaagaa      180
tgcaccactc cagaatctcc tgaactcgct gcattggcaa aaaccacagc caccgaagcc      240
tggggagaac acttccacgg aggtacaacc gtccgtcctc tagaacaaga gatgctttct      300
```

| | |
|---|---:|
| ggtcatatcg aaggacaaac cttaaagatg tttgttcaca tgaccaaagc taaaaaagtc | 360 |
| ttagaaattg ggatgtttac cggttattcg gcgctggcga tggcggaagc attaccagag | 420 |
| gatggactgc ttgtggcttg tgaagttgac ccttacgcgg cggaaattgg acagaaagcc | 480 |
| tttcaacaat ctccccacgg tggaaagatt cgtgtggaat tggatgcagc cttagcaact | 540 |
| cttgataagt tagcagaagc tggggagtct tttgacttgg tatttatcga cgcagataaa | 600 |
| aaagagtatg tagcctattt tcacaagttg ctaggtagca gtttgttagc accagatggc | 660 |
| tttatttgtg tagataacac cttattacaa ggggaagttt atctaccagc agaggaacgt | 720 |
| agcgtcaatg gtgaagcgat cgcgcaattt aatcatacag tagctataga cccccgtgta | 780 |
| gaacaggttt tgttgccgtt gcgagatggt ttaacaatta ccgcagaat acaaccttaa | 840 |

<210> SEQ ID NO 10
<211> LENGTH: 14
<212> TYPE: DNA
<213> ORGANISM: Anabaena variabili

<400> SEQUENCE: 10

| | |
|---|---:|
| ttgtccaatc gact | 14 |

<210> SEQ ID NO 11
<211> LENGTH: 1377
<212> TYPE: DNA
<213> ORGANISM: Anabaena variabilis

<400> SEQUENCE: 11

| | |
|---|---:|
| atggcacaat cccttcccct ttcttccgca cctgctacac cgtctcttcc ttcccagacg | 60 |
| aaaatagccg caattatcca aaatatctgc actttggctt tgttattact agcattgccc | 120 |
| attaatgcca ccattgtttt tatatccttg ttagtcttcc gaccgcaaaa ggtcaaagca | 180 |
| gcaaaccccc aaaccattct tatcagtggc ggtaagatga ccaaagcttt acaactagca | 240 |
| aggtcattcc acgcggctgg acatagagtt gtcttggtgg aaacccataa atactggttg | 300 |
| actggtcatc gttttttccca agcagtggat aagttttaca cagtccccgc accccaggac | 360 |
| aatccccaag cttacattca ggctttggta gatatcgtca acaagaaaaa catcgatgtt | 420 |
| tatattcccg tcaccagtcc agtgggtagc tactacgact cattagccaa accagagtta | 480 |
| tcccattatt gcgaagtgtt tcactttgac gcagatatta cccaaatgtt ggatgataaa | 540 |
| tttgcgttga cacaaaaagc gcgatcgctt ggtttatcag tacccaaatc ctttaaaatt | 600 |
| acctcaccag aacaagtcat caacttcgat ttttctggag agacacgtaa atacatcctc | 660 |
| aaaagcattc cctacgactc agtgcggcgg ttggacttaa ccaaactccc ctgtgctact | 720 |
| ccagaggaaa cagcagcatt cgtcagaagt ttgccaatta ctcccgaaaa accgtggatt | 780 |
| atgcaggaat ttatccccgg taaggaattc tgcacccata gcaccgttcg gaatggggaa | 840 |
| ctcagactgc attgctgttg cgaatcttca gccttccaag ttaattatga gaatgtaaat | 900 |
| aacccgcaaa ttaccgaatg ggtacagcat tttgtcaagg aactgaaact gacaggacag | 960 |
| atttcctttg actttatcca agccgaagac ggaacagttt acgccatcga gtgtaacccc | 1020 |
| cgcacacatt cagcaattac cacattttac gaccacccccc aggtagcaga agcgtacttg | 1080 |
| agtcaagcac cgacgactga aaccatacaa ccactaacga caagcaagcc taccttattgg | 1140 |
| acttatcacg aagtttggcg tttaactggt atccgttctt tcacccagtt gcaaagatgg | 1200 |
| ctggggaata tttggcgcgg gactgatgcg atttatcagc cagatgaccc cttaccgttt | 1260 |
| ttgatggtac atcattggca aattcccctta ctgttattga ataatttgcg tcgtcttaaa | 1320 |

```
ggttggacgc ggatagattt caatattggg aagttggtgg aattgggggg agattag      1377
```

<210> SEQ ID NO 12
<211> LENGTH: 156
<212> TYPE: DNA
<213> ORGANISM: Anabaena variabilis

<400> SEQUENCE: 12

```
tttttaaacg cagagggacg ctgaggttag cgcagcgaaa agttctggag gagggtttcc    60
ctccgtagga aacttttcaa gagagaggga cgcggagtgt gttttctctg cgtctctgcg   120
tgagaaattt tttattattg agcaaagtta gaagat                             156
```

<210> SEQ ID NO 13
<211> LENGTH: 2667
<212> TYPE: DNA
<213> ORGANISM: Anabaena variabilis

<400> SEQUENCE: 13

```
atgcagacta tagattttaa tattcgtaag ttacttgtag agtggaacgc gacccacaga    60
gattatgatc tttcccagag tttacatgaa ctaattgtga ctcaagtaga acgaacacct   120
gaggcgatcg ctgtcacctt tgacaagcaa caactaactt atcaagaact aaatcataaa   180
gcaaaccagc taggacatta tttacaaaca ttaggagtcc agccagaaac cctggtaggc   240
gtttgtttag aacgttcctt agaaatggtt atctgtcttt taggaatcct caaagctggg   300
ggtgcttatg ttcctattga ccctgaatat cctcaagaac gcatagctta tgctagaa    360
gattctcagg tgaaggtact actaactcaa gaaaaattac tcaatcaaat tccccaccat   420
caagcacaaa ctatctgtgt agataggaa tgggagaaaa tttccacaca agctaatacc   480
aatcccaaaa gtaatataaa aacggataat cttgcttatg taatttacac ctctggttcc   540
actggtaaac caaaggtgc aatgaacacc cacaaaggta tctgtaatcg cttattgtgg   600
atgcaggaag cttatcaaat cgattccaca gatagcattt tacaaaaaac cccctttagt   660
tttgatgttt ccgtttggga gttcttttgg actttattaa ctggcgcacg tttggtaata   720
gccaaaccag gcggacataa agatagtgct tacctcatcg atttaattac tcaagaacaa   780
atcactacgt tgcattttgt cccctcaatg ctgcaagtgt ttttacaaaa tcgccatgta   840
agcaaatgca gctctctaaa aagagttatt tgtagcggtg aagctttatc tatagattta   900
caaaatagat ttttccagca tttgcaatgt gaattacata acctctatgg cccgacagaa   960
gcagcaattg atgtcacatt ttggcaatgt agaaaagata gtaatttaaa gagtgtacct  1020
attggtcgtc ccattgctaa tactcaaatt tatattcttg atgccgattt acaaccagta  1080
aatattggtg tcactggtga aatttatatt ggtggtgtag gggttgctcg tggttatttg  1140
aataaagaag aattgaccaa agaaaaattt attattaatc cctttcccaa ttctgagttt  1200
aagcgacttt ataaaacagg tgatttagct cgttatttac ccgatggaaa tattgaatat  1260
cttggtagaa cagattatca agtaaaaatt cggggttata gaattgaaat tggcgagatt  1320
gaaaatgttt tatcttcaca cccacaagtc agagaagctg tagtcatagc gcgggatgat  1380
aacgctcaag aaaaacaaat catcgcttat attacctata actccatcaa acctcagctt  1440
gataatctgc gtgatttcct aaaagcaagg ctacctgatt ttatgattcc agccgctttt  1500
gtgatgctgg agcatcttcc tttaactccc agtggtaaag tagaccgtaa ggcattacct  1560
aagcctgatt tatttaatta tagtgaacat aattcctatg tagcgcctcg gaatgaagtt  1620
```

```
gaagaaaaat tagtacaaat ctggtcgaat attctgcatt tacctaaagt aggtgtgaca   1680
gaaaactttt tcgctattgg tggtaattcc ctcaaagctc tacatttaat ttctcaaatt   1740
gaagagttat ttgctaaaga gatatcctta gcaacacttt taacaaatcc agtaattgca   1800
gatttagcca aggttattca agcaaacaac caaatccata attcacccct agttccaatt   1860
caaccacaag gtaagcagca gcctttcttt tgtatacatc ctgctggtgg tcatgtttta   1920
tgctatttta aactcgcaca atatatagga actgaccaac catttatgg cttacaagct    1980 caaggatttt atggagatga agcacccttg acgcgagttg aagatatggc tagtctctac   2040
gtcaaaacta ttagagaatt caaccccaa gggccttatc gtgtcgggg gtggtcattt     2100 ggtggagtcg tagcttatga agtagcacag cagttacata gacaaggaca agaagtatct   2160
ttactagcaa tattgattc ttacgtaccg attctgctgg ataaacaaaa acccattgat    2220
gacgtttatt tagttggtgt tctctccaga gttttttggcg gtatgtttgg tcaagataat  2280
ctagtcacac ctgaagaaat agaaaattta actgtagaag aaaaaattaa ttacatcatt   2340
gataaagcac ggagcgctag aatattcccg cctggtgtaa acgtcaaaaa taatcgccgt   2400
attcttgatg ttttggtggg aactttaaaa gcaacttatt cctatataag acaaccatat   2460
ccaggaaaag tcactgtatt tcgagccagg gaaaaacata ttatggctcc tgacccgacc   2520
ttagtttggg tagaattatt ttctgtaatg gcggctcaag aaattaagat tattgatgtc   2580
cctggaaacc attattcgtt tgttctagaa ccccatgtac aggttttagc acagcgttta   2640
caagattgtc tggaaaataa ttcataa                                       2667

<210> SEQ ID NO 14
<211> LENGTH: 6469
<212> TYPE: DNA
<213> ORGANISM: Artificial Sequence
<220> FEATURE:
<223> OTHER INFORMATION: synthetic sequence

<400> SEQUENCE: 14
tcgagatgaa ttattttcca gacaatcttg taaacgctgt gctaaaacct gtacatgggg    60
ttctagaaca aacgaataat ggtttccagg gacatcaata atcttaattt cttgagccgc   120
cattacagaa aataattcta cccaaactaa ggtcgggtca ggagccataa tatgtttttc   180
cctggctcga aatacagtga cttttcctgg atatggttgt cttatatagg aataagttgc   240
ttttaaagtt cccaccaaaa catcaagaat acggcgatta ttttgacgtt ctacaccagg    300
cgggaatatt ctagcgctcc gtgctttatc aatgatgtaa ttaatttttt cttctacagt    360 taaatttct atttcttcag gtgtgactag attatcttga ccaaacatac cgccaaaaac    420
tctggagaga acaccaacta aataaacgtc atcaatgggt ttttgtttat ccagcagaat    480
cggtacgtaa gaatctaata ttgctagtaa agatacttct tgtccttgtc tatgtaactg    540
ctgtgctact tcataagcta cgactccacc aaatgaccac cccccgacac gataaggccc    600
ttggggttga aattctctaa tagttttgac gtagagacta gccatatctt caactcgcgt    660
caagggtgct tcatctccat aaaatccttg agcttgtaag ccataaaatg gttggtcagt    720
tcctatatat tgtgcgagtt taaaatagca taaaacatga ccaccagcag gatgtataca    780
aaagaaaggc tgctgcttac cttgtggttg aattggaact aggggtgaat tatggatttg    840
gttgtttgct tgaataacct tggctaaatc tgcaattact ggatttgtta aaagtgttgc    900
taaggatatc tctttagcaa ataactcttc aatttgagaa attaaatgta gagctttgag    960
ggaattacca ccaatagcga aaagttttc tgtcacacct actttaggta aatgcagaat    1020
```

```
attcgaccag atttgtacta attttcttc aacttcattc cgaggcgcta cataggaatt    1080
atgttcacta taattaaata aatcaggctt aggtaatgcc ttacggtcta ctttaccact    1140
gggagttaaa ggaagatgct ccagcatcac aaaagcggct ggaatcataa aatcaggtag    1200
ccttgctttt aggaaatcac gcagattatc aagctgaggt ttgatggagt tataggtaat    1260
ataagcgatg atttgttttt cttgagcgtt atcatcccgc gctatgacta cagcttctct    1320
gacttgtggg tgtgaagata aacatttc aatctcgcca atttcaattc tataaccccg    1380 aattttact tgataatctg ttctaccaag atattcaata tttccatcgg gtaaataacg    1440
agctaaatca cctgttttat aaagtcgctt aaactcagaa ttgggaaagg gattaataat    1500 aaattttct ttggtcaatt cttctttatt caaataacca cgagcaaccc ctacaccacc    1560
aatataaatt tcaccagtga caccaatatt tactggttgt aaatcggcat caagaatata    1620
aatttgagta ttagcaatgg gacgaccaat aggtacactc tttaaattac tatctttct    1680 acattgccaa aatgtgacat caattgctgc ttctgtcggg ccatagaggt tatgtaattc    1740
acattgcaaa tgctggaaaa atctattttg taaatctata gataaagctt caccgctaca    1800
aataactctt tttagagagc tgcatttgct tacatggcga ttttgtaaaa acacttgcag    1860
cattgagggg acaaaatgca acgtagtgat ttgttcttga gtaattaaat cgatgaggta    1920
agcactatct ttatgtccgc ctggtttggc tattaccaaa cgtgcgccag ttaataaagt    1980
ccaaaagaac tcccaaacgg aaacatcaaa actaaggggg ttttttgta aaatgctatc    2040 tgtggaatcg atttgataag cttcctgcat ccacaataag cgattacaga taccttgtg    2100 ggtgttcatt gcacctttg gtttaccagt ggaaccagag gtgtaaatta cataagcaag    2160
attatccgtt tttatattac tttgggatt ggtattagct tgtgtggaaa ttttctccca    2220
ttccctatct acacagatag tttgtgcttg atggtgggga atttgattga gtaatttttc    2280
ttgagttagt agtaccttca cctgagaatc ttctagcata taagctatgc gttcttgagg    2340
atattcaggg tcaataggaa cataagcacc cccagctttg aggattccta aaagacagat    2400
aaccatttct aaggaacgtt ctaaacaaac gcctaccagg gtttctggct ggactcctaa    2460
tgtttgtaaa taatgtccta gctggtttgc tttatgattt agttcttgat aagttagttg    2520
ttgcttgtca aaggtgacag cgatcgcctc aggtgttcgt tctacttgag ctacaattag    2580
ttcatgtaaa ctctgggaaa gatcataatc tctgtgggtc gcgttccact ctacaagtaa    2640
cttacgaata ttaaaatcta tagtctgcat atcttctaac tttgctcaat aataaaaaat    2700
ttctcacgca gagacgcaga gaaaacacac tccgcgtccc tctctcttga aaagtttcct    2760
acggagggaa accctcctcc agaactttc gctgcgctaa cctcagcgtc cctctgcgtt    2820 taaaactaa tctcccccca attccaccaa cttcccaata ttgaaatcta tccgcgtcca    2880
acctttaaga cgacgcaaat tattcaataa cagtagggga atttgccaat gatgtaccat    2940
caaaaacggt aaggggtcat ctggctgata aatcgcatca gtcccgcgcc aaatattccc    3000
cagccatctt tgcaactggg tgaaagaacg gataccagtt aaacgccaaa cttcgtgata    3060
agtccaatag gtaggcttgc ttgtcgttag tggttgtatg gtttcagtcg tcggtgcttg    3120
actcaagtac gcttctgcta cctggggggtg gtcgtaaaat gtggtaattg ctgaatgtgt    3180 gcggggggtta cactcgatgg cgtaaactgt tccgtcttcg gcttggataa agtcaaagga    3240
aatctgtcct gtcagtttca gttccttgac aaaatgctgt acccattcgg taatttgcgg    3300
gttatttaca ttctcataat taacttggaa ggctgaagat tcgcaacagc aatgcagtct    3360
```

```
gagttcccca ttccgaacgg tgctatgggt gcagaattcc ttaccgggga taaattcctg      3420
cataatccac ggttttttcgg gagtaattgg caaacttctg acgaatgctg ctgtttcctc      3480
tggagtagca caggggagtt tggttaagtc caaccgccgc actgagtcgt agggaatgct      3540
tttgaggatg tatttacgtg tctctccaga aaaatcgaag ttgatgactt gttctggtga      3600 ggtaattttta aaggatttgg gtactgataa accaagcgat cgcgcttttt gtgtcaacgc      3660
aaatttatca tccaacattt gggtaatatc tgcgtcaaag tgaaacactt cgcaataatg      3720
ggataactct ggtttggcta atgagtcgta gtagctaccc actggactgg tgacgggaat      3780
ataaacatcg atgttttctt gtttgacgat atctaccaaa gcctgaatgt aagcttgggg      3840
attgtcctgg ggtgcgggga ctgtgtaaaa cttatccact gcttgggaaa aacgatgacc      3900
agtcaaccag tatttatggg tttccaccaa gacaactcta tgtccagccg cgtggaatga      3960
ccttgctagt tgtaaagctt tggtcatctt accgccactg ataagaatgg tttgggggtt      4020
tgctgctttg accttttgcg gtcggaagac taacaaggat ataaaaacaa tggtggcatt      4080
aatgggcaat gctagtaata acaaagccaa agtgcagata ttttggataa ttgcggctat      4140
tttcgtctgg gaaggaagag acggtgtagc aggtgcggaa gaaaggggaa gggattgtgc      4200
catagtcgat tggacaatta aggttgtatt ctgcggataa ttgttaaacc atctcgcaac      4260
ggcaacaaaa cctgttctac acggggggtct atagctactg tatgattaaa ttgcgcgatc      4320
gcttcaccat tgacgctacg ttcctctgct ggtagataaa cttccccttg taataaggtg      4380
ttatctacac aaataaagcc atctggtgct aacaaactgc tacctagcaa cttgtgaaaa      4440
taggctacat actcttttttt atctgcgtcg ataaatacca agtcaaaaga ctccccagct      4500
tctgctaact tatcaagagt tgctaaggct gcatccaatt ccacacgaat cttttccaccg      4560 tggggagatt gttgaaaggc tttctgtcca atttccgccg cgtaagggtc aacttcacaa      4620
gccacaagca gtccatcctc tggtaatgct tccgccatcg ccagcgccga taaccggta      4680 aacatcccaa tttctaagac tttttttagct ttggtcatgt gaacaaacat ctttaaggtt      4740
tgtccttcga tatgaccaga aagcatctct tgttctagag acggacggt tgtacctccg      4800 tggaagtgtt ctccccaggc ttcggtggct gtggttttg ccaatgcagc gagttcagga      4860
gattctggag tggtgcattc ttccaaataa gggtctatac ctgcggctaa acgccaagcc      4920
tgatggatgt ttgctatcaa ttccccaggt aaatctggat gttgcttaac ctcttggact      4980
atggcttcta actgcttggt taaaattccc aatggtgtaa caggtctagc tgttggttgg      5040
acaatcacat ttgtcaagtc gcttcgctcc aattcaaaat tcaaaattca aaattcaaaa      5100
ttaaagacaa ttagtgtccg attatttgcg tagccttctc tttccctacg ggacgctccg      5160
cgaacagaaa tgctaccgcg ctcgcgcagt gtatccgtgg agtatttgc attttgaatt      5220 caaaaaagtc attatttaac actcccgatt aattcttttt gataaacggg atacacatcc      5280
acaccttcac caccacgggg ataactggta caaagttctt tgtggtcagc taatgcggct      5340
gctaattctt ctcttgtcag gtcattgacg aagacacaat caccaatggg ttttggcata      5400
gcagctctta acaaaccatc acgagttaat gtgatagatt cagtaccacg ccacaaaata      5460
tctatatcca acatgggatg gtcgagggat agaccaacgc gactcattaa tcctaaaata      5520
cgatcgcgtt ctgcaattgt aatatatcct ctacgggcgg cgatcgttgc cgagaaagcc      5580
atatctacat taacgcgtg tccgtggaac atgggtagac gaggcgcaag ttccaaggtg      5640
ggactccaag tgtgaccgta agcaatcacc ctatctaggt ctaactcatg caggttggga      5700
acttccaatt ccaacatctt atggatagct ttgtaagtca aacgatgggc tatttctttta      5760
```

```
atctctggag ttgcatctat attgccaaaa tgagtacgta gtaattcttc gccgtacttc    5820
tccaacaatt caaaaacttc ttgatgcgct actacagcga tttttaccaa ttccgccatc    5880
ccgttacgta cttggtctgt agggagagta cgcaacaagg agaaatctaa aaatactttg    5940
cgagaagcat gataagcacc caaacggttt ttcagtttgc gatgattaac tgctacctta    6000
attgctacac tggcatcaat taatccaatc aatgtagtag gaatgcggat gtaattgctg    6060
ctgcgacgat atgtagaaca agcaaagccg acaacatctg taattaaacc gccacccacg    6120
actaatactg gttctttgcg gactaatttg aaatctgcaa agacatctat aactctctcg    6180
aaagtttgaa tagtcttatc tggttcagta atggtaatag gaaatagcct cagttctata    6240
ccataatact ggaaatatgc ctgaatttga ttaccataca accgactgac gttagcatct    6300
acaatcgcca agcatcgtcc aaaaccttga tatacatctg ctagtgcaga attctggatt    6360
tcaaaaatac catctacata caccaaatca tactcaatct tttcgtaacc ttctacatga    6420
aaagatgttt ccttagcttc aaactttgct tggacgatac tcatagctc                6469
```

<210> SEQ ID NO 15
<211> LENGTH: 11078
<212> TYPE: DNA
<213> ORGANISM: Artificial Sequence
<220> FEATURE:
<223> OTHER INFORMATION: synthetic vector sequence
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (3343)..(3343)
<223> OTHER INFORMATION: n is a, c, g, or t
<220> FEATURE:
<221> NAME/KEY: misc_feature
<222> LOCATION: (3345)..(3345)
<223> OTHER INFORMATION: n is a, c, g, or t
<220> FEATURE:
<221> NAME/KEY: misc_feature
<222> LOCATION: (3347)..(3347)
<223> OTHER INFORMATION: n is a, c, g, or t
<220> FEATURE:
<221> NAME/KEY: misc_feature
<222> LOCATION: (9883)..(9883)
<223> OTHER INFORMATION: n is a, c, g, or t

<400> SEQUENCE: 15

```
actbactsan tartmasmdm ccgctcattt ttggggtcca gctggttcag ctggtcagta      60
tggctgaaag ccatggtctt aaaaagcagt tcggcgattt tgctgatct gcttttggg      120 ggttgaaacc gtcgtttttt cgacggtttc ttcttatctt gatactatta gaaacaacgt     180
cattttaaaa aaccgggata aaccttgac acaactgggc ttaggcgtat tatgagttta     240
taaaatgaat aaagaaaaaa cccacgtgag aattcctagt ttggcgaccc ggaacacgtg     300
agttaatctt gaatattcgt atttactaga catagtttaa agcttgagtt agcaagcgtc     360
aagcccttgg ctttagtaaa tacataaaag attagctctt ctcacgtggc tgaatgaggg     420 gagctttta gtttggctga tagaaaagtt ttagttgatc gatcgcagtc gggcaaagta     480
cgaccatggc gagaacataa gttagaaaat ttacagtatg tgattatttt acaaatgttg    540
cactacaaga aagcccatcg agttaaagag tgtggtgaag tattacgttt tgtggaagat    600
aaaaatggtc acaaaaaact ggctcagact tggttttgcc attcccgttt gtgtccgtta    660
tgtaattggc ggcggtcaat gaaacaatct aaccagttaa ctcaaatttt gacagaagca    720
```

```
gttaaacagc gaaaaacggg tcggttcttg tttttaacat tgacggtaga gaatactaca    780
ggggatttgt tgaagagtga attacggcag atgggacgag ccattgcaaa gatctttcag    840
tataaaaaag tggctaaaaa tttgttgggc tatgtacgtt caactgaggt taccattaat    900
cacgaagcgg atcagccgat gtatcaccac catatgcatg ttttgctttt tatgaaatct    960
agttatttta caggaactga taattatatt tcacaaacag aatggactag atattggcaa   1020
cgagcgatga aattagctta tgtgccggtt gtgaatgttg aagcggttaa accgaatgtg   1080
aaacgccaga aaaattcctt actggctagt gcccaagaaa cggctaagta tcaggtgaag   1140
tccaaagata ttttaactaa taatcaagaa caagatttac aagtaattga tgatttggaa   1200
caagctttgg ctggttcccg gcaaattagc tatgggggtt tgttaaaaga aattcgtaag   1260
caattgcaac tagaagatgt tgaaaatggt gatttaatta tacggatag tgatgatcaa    1320
aaagttgacc aagtggtacg cgagattgtt gctaagtggg actatcagcg aaaaaattac   1380
tttatttgaa tgagtgctat attatatata aagacaggaa atcatttgtc tagcgggggg   1440
aactctttta tgatttatgc tactgctgtt aaatttgaag atgaaaattc tgatagaaca   1500
cctaaagcga ttgattctat ttatttagat tctacttcgg atgaaacttg gcattttgga   1560
gagggagaaa acactactcc tattaagggt tggtatgata acatgatgt ttatcgttgg    1620
ttatttttga atttttgataa aggccttgtg atgaaggttg ttactggtga aaaaccggat   1680
ataaagcctg ttggtaaaga taaagatgac ccggatggat atgttagatc tgaaaagaat   1740
ggtattgttg ttgataatct tgaaatgctt ccagattcgc cttctccttt gtgatattaa   1800
agaatggaga acgtttattt tgattttgaa tttgtttttt attaataatc attgggagcg   1860
aaagcgacct ttgattattt ttttgccaac ggcaaaaatc gcctcgcaga gcccaaactt   1920
tacaaggtaa agtatattgg gctataacctt gcatggaggt ttgccgaatt ctgtgctatg   1980
ctctaaccaa atttagctgt ttggaaatgg agtggtgaaa tgagttattt agtggctaat   2040
atgcagaaat taaagctga taatttagtt ggcttgggta atcatgatca acgccgaacg    2100
caacatcaca aaaatactga tattgacgtt gaccgttctg gcttaaatta tgatttagtt   2160
gctggtcgga ctaaccattt caaaacggat attgcggctt atattaacga gcataaaacc   2220
agtcagcgag cggtcagaaa agatgccgtt ttagtcaatg aatggattat ttcgagcgat   2280
agcaattttct ttgctaattt aacggcggct gatacgcgca atatttttga aacagctaaa   2340
gcttactttg ctgaaaaatt tggtgaagaa atatattcgct atgcaattgt tcaccttgat   2400
gagagtacgc cacatatgca tatgggaatt gtgccctttg atgatgaata taagttgtct   2460
gctaaacggg tgtttaatcg tgcggctttg caaaacgttc aagatcaatt gccgacttat   2520
ttgcaacagc atggttttaa tattcaacgt ggggttcaag aatcggaacg caaaagttta   2580
acggtgccag aatataaagc tatgcgggaa gatttgaaaa aggcgacgct tcaaaaacaa   2640
gaaatacaag ctgaacttga agatgccaga aaacgccttg ctgaacttaa acctcgtgat   2700
cagcaggaaa ttgagagcaa acctactttt ttaagcaagg ataaagtggt tgttagaaaa   2760
agtgatcttc atgacttaga atctcgagca gctgtcagtg atatttataa tcaacaacag   2820
aaccgtttaa aacttgataa tcaaagccta aattatcaac tgcttgaagt taagacaat   2880
aattatgagt taagcaagaa aaatgagaag ctccaaaaat tagtggatac gttacaagga   2940
attgttcgga gcgttgaccg gttcttacag cgcaaattag gtgttggctt accaagtgag   3000
tggctagaac gagctggact aaaagaaccg tctaaaaacg cccctcagag gccgcaggaa   3060
cgttcggagg gacagcatga tgaattagat ggtccaagtc tttgaatttg tcctatggct   3120
```

```
ttaaattacc cgctgatgag cattgaagct ggttaatggc cgtcagtcaa cggtaaatcg    3180
aattaaaggg acttactgct ttagcagtta gtcccttttt gaggctttaa ggagttgact    3240
gactcactag accaagacac ttttgcgcat gcaaagaaaa gcacacctgc ttttttttgcc   3300 tgcctcacgc cgagtgcggg gtgagtttga gcgggagctc shnrnrnwth rmtragatct    3360
agcgctatag ttgttgacag aatggacata ctatgatata ttttgctata gcgatgaatt    3420
attttccaga caatcttgta aacgctgtgc taaaacctgt acatgggtt  ctagaacaaa    3480 cgaataatgg tttccaggga catcaataat cttaatttct tgagccgcca ttacagaaaa    3540
taattctacc caaactaagg tcgggtcagg agccataata tgttttttccc tggctcgaaa   3600 tacagtgact tttcctggat atggttgtct tatataggaa taagttgctt ttaaagttcc    3660
caccaaaaca tcaagaatac ggcgattatt ttgacgttct acaccaggcg ggaatattct    3720
agcgctccgt gctttatcaa tgatgtaatt aattttttct tctacagtta aattttctat    3780
ttcttcaggt gtgactagat tatcttgacc aaacataccg ccaaaaactc tggagagaac    3840
accaactaaa taaacgtcat caatgggttt ttgtttatcc agcagaatcg gtacgtaaga    3900
atctaatatt gctagtaaag atacttcttg tccttgtcta tgtaactgct gtgctacttc    3960
ataagctacg actccaccaa atgaccaccc cccgacacga taaggcccctt ggggttgaaa   4020 ttctctaata gttttgacgt agagactagc catatcttca actcgcgtca agggtgcttc    4080
atctccataa aatccttgag cttgtaagcc ataaaatggt tggtcagttc ctatatattg    4140
tgcgagttta aaatagcata aaacatgacc accagcagga tgtatacaaa agaaaggctg    4200
ctgcttacct tgtggttgaa ttggaactag gggtgaatta tggatttggt tgtttgcttg    4260 ataaccttg  gctaaatctg caattactgg atttgttaaa agtgttgcta aggatatctc    4320
tttagcaaat aactcttcaa tttgagaaat taaatgtaga gctttgaggg aattaccacc    4380
aatagcgaaa aagttttctg tcacacctac tttaggtaaa tgcagaatat tcgaccagat    4440
ttgtactaat ttttcttcaa cttcattccg aggcgctaca taggaattat gttcactata    4500
attaaataaa tcaggcttag gtaatgcctt acggtctact ttaccactgg gagttaaagg    4560
aagatgctcc agcatcacaa aagcggctgg aatcataaaa tcaggtagcc ttgcttttag    4620
gaaatcacgc agattatcaa gctgaggttt gatggagtta taggtaatat aagcgatgat    4680 ttgttttttct tgagcgttat catcccgcgc tatgactaca gcttctctga cttgtgggtg    4740
tgaagataaa acatttttcaa tctcgccaat ttcaattcta taaccccgaa ttttttacttg   4800 ataatctgtt ctaccaagat attcaatatt tccatcgggt aaataacgag ctaaatcacc    4860
tgttttataa agtcgcttaa actcagaatt gggaaaggga ttaataataa attttttcttt   4920 ggtcaattct tctttattca aataaccacg agcaaccccct acaccaccaa tataaatttc    4980
accagtgaca ccaatatttta ctggttgtaa atcggcatca agaatataaa tttgagtatt    5040
agcaatggga cgaccaatag gtacactctt taaattacta tcttttctac attgccaaaa    5100
tgtgacatca attgctgctt ctgtcgggcc atagaggtta tgtaattcac attgcaaatg    5160
ctggaaaaat ctattttgta aatctataga taaagcttca ccgctacaaa taactctttt    5220
tagagagctg catttgctta catggcgatt ttgtaaaaac acttgcagca ttgaggggac    5280
aaaatgcaac gtagtgattt gttcttgagt aattaaatcg atgaggtaag cactatcttt    5340
atgtccgcct ggtttggcta ttaccaaacg tgcgccagtt aataaagtcc aaaagaactc    5400
ccaaacggaa acatcaaaac taaggggggt ttttgtaaa  atgctatctg tggaatcgat    5460
```

```
ttgataagct tcctgcatcc acaataagcg attacagata cctttgtggg tgttcattgc    5520 acctttggt  ttaccagtgg aaccagaggt gtaaattaca taagcaagat tatccgtttt    5580
tatattactt tgggattgg  tattagcttg tgtggaaatt ttctcccatt ccctatctac    5640
acagatagtt tgtgcttgat ggtggggaat ttgattgag  aattttttctt gagttagtag   5700 taccttcacc tgagaatctt ctagcatata agctatgcgt tcttgaggat attcagggtc    5760
aataggaaca taagcacccc cagctttgag gattcctaaa agacagataa ccatttctaa    5820
ggaacgttct aaacaaacgc ctaccagggt ttctggctgg actcctaatg tttgtaaata    5880
atgtcctagc tggtttgctt tatgatttag ttcttgataa gttagttgtt gcttgtcaaa    5940
ggtgacagcg atcgcctcag gtgttcgttc tacttgagct acaattagtt catgtaaact    6000 ctggaaaga  tcataatctc tgtgggtcgc gttccactct acaagtaact tacgaatatt    6060
aaaatctata gtctgcatat cttctaactt tgctcaataa taaaaatttt ctcacgcaga    6120
gacgcagaga aaacacactc cgcgtccctc tctcttgaaa agtttcctac ggagggaaac    6180
cctcctccag aacttttcgc tgcgctaacc tcagcgtccc tctgcgttta aaaactaatc    6240 tcccccaat  tccaccaact tcccaatatt gaaatctatc cgcgtccaac ctttaagacg    6300
acgcaaatta ttcaataaca gtaggggaat ttgccaatga tgtaccatca aaaacggtaa    6360
ggggtcatct ggctgataaa tcgcatcagt cccgcgccaa atattcccca gccatctttg    6420
caactgggtg aaagaacgga taccagttaa acgccaaact tcgtgataag tccaataggt    6480
aggcttgctt gtcgttagtg gttgtatggt ttcagtcgtc ggtgcttgac tcaagtacgc    6540
ttctgctacc tggggtggt  cgtaaaatgt ggtaattgct gaatgtgtgc gggggttaca    6600
ctcgatggcg taaactgttc cgtcttcggc ttggataaag tcaaaggaaa tctgtcctgt    6660
cagtttcagt tccttgacaa aatgctgtac ccattcggta atttgcgggt tatttacatt    6720
ctcataatta acttggaagg ctgaagattc gcaacagcaa tgcagtctga gttccccatt    6780
ccgaacggtg ctatgggtgc agaattcctt accggggata aattcctgca taatccacgg    6840
tttttcggga gtaattggca aacttctgac gaatgctgct gttttcctctg gagtagcaca   6900 ggggagtttg gttaagtcca accgccgcac tgagtcgtag ggaatgcttt tgaggatgta    6960
tttacgtgtc tctccagaaa aatcgaagtt gatgacttgt tctggtgagg taattttaaa    7020
ggatttgggt actgataaac caagcgatcg cgcttttttgt gtcaacgcaa atttatcatc    7080
caacatttgg gtaatatctg cgtcaaagtg aaacacttcg caataatggg ataactctgg    7140
tttggctaat gagtcgtagt agctacccac tggactggtg acgggaatat aaacatcgat    7200
gttttcttgt ttgacgatat ctaccaaagc ctgaatgtaa gcttggggat tgtcctgggg    7260
tgcggggact gtgtaaaact tatccactgc ttgggaaaaa cgatgaccag tcaaccagta    7320
tttatgggtt tccaccaaga caactctatg tccagccgcg tggaatgacc ttgctagttg    7380
taaagctttg gtcatcttac cgccactgat aagaatggtt tgggggtttg ctgctttgac    7440
cttttgcggt cggaagacta acaaggatat aaaaacaatg gtggcattaa tgggcaatgc    7500
tagtaataac aaagccaaag tgcagatatt ttggataatt gcggctattt tcgtctggga    7560
aggaagagac ggtgtagcag gtgcggaaga aaggggaagg gattgtgcca tagtcgattg    7620
gacaattaag gttgtattct gcggataatt gttaaaccat ctcgcaacgg caacaaaacc    7680
tgttctacac gggggtctat agctactgta tgattaaatt gcgcgatcgc ttccaccattg   7740 acgctacgtt cctctgctgg tagataaact tccccttgta ataaggtgtt atctacacaa    7800
ataaagccat ctggtgctaa caaactgcta cctagcaact tgtgaaaata ggctacatac    7860
```

```
tcttttttat ctgcgtcgat aaataccaag tcaaaagact ccccagcttc tgctaactta    7920
tcaagagttg ctaaggctgc atccaattcc acacgaatct ttccaccgtg gggagattgt    7980
tgaaaggctt tctgtccaat ttccgccgcg taagggtcaa cttcacaagc cacaagcagt    8040
ccatcctctg gtaatgcttc cgccatcgcc agcgccgaat aaccggtaaa catcccaatt    8100
tctaagactt ttttagcttt ggtcatgtga acaaacatct ttaaggtttg tccttcgata    8160
tgaccagaaa gcatctcttg ttctagagga cggacggttg tacctccgtg gaagtgttct    8220
ccccaggctt cggtggctgt ggttttttgcc aatgcagcga gttcaggaga ttctggagtg    8280
gtgcattctt ccaaataagg gtctatacct gcggctaaac gccaagcctg atggatgttt    8340
gctatcaatt ccccaggtaa atctggatgt tgcttaacct cttggactat ggcttctaac    8400
tgcttggtta aaattcccaa tggtgtaaca ggtctagctg ttggttggac aatcacattt    8460
gtcaagtcgc ttcgctccaa ttcaaaattc aaaattcaaa attcaaaatt aagacaatt    8520 agtgtccgat tatttgcgta gccttctctt tccctacggg acgctccgcg aacagaaatg    8580
ctaccgcgct cgcgcagtgt atccgtggag tattttgcat tttgaattca aaaagtcat    8640 tatttaacac tcccgattaa ttcttttttga taaacgggat acacatccac accttcacca    8700
ccacggggat aactggtaca aagttctttg tggtcagcta atgcggctgc taattcttct    8760
cttgtcaggt cattgacgaa gacacaatca ccaatgggtt ttggcatagc agctcttaac    8820
aaaccatcac gagttaatgt gatagattca gtaccacgcc acaaaatatc tatatccaac    8880
atgggatggt cgagggatag accaacgcga ctcattaatc ctaaaatacg atcgcgttct    8940
gcaattgtaa tatatcctct acgggcggcg atcgttgccg agaaagccat atctacatta    9000
acggcgtgtc cgtggaacat gggtagacga ggcgcaagtt ccaagtgggg actccaagtg    9060
tgaccgtaag caatcaccct atctaggtct aactcatgca ggttgggaac ttccaattcc    9120
aacatcttat ggatagcttt gtaagtcaaa cgatgggcta tttctttaat ctctggagtt    9180
gcatctatat tgccaaaatg agtacgtagt aattcttcgc cgtacttctc caacaattca    9240
aaaacttctt gatgcgctac tacagcgatt tttaccaatt ccgccatccc gttacgtact    9300
tggtctgtag ggagagtacg caacaaggag aaatctaaaa atactttgcg agaagcatga    9360
taagcaccca aacggttttt cagtttgcga tgattaactg ctaccttaat tgctacactg    9420
gcatcaatta atccaatcaa tgtagtagga atgcggatgt aattgctgct gcgacgtat    9480 gtagaacaag caaagccgac aacatctgta attaaaccgc cacccacgac taatactggt    9540
tctttgcgga ctaatttgaa atctgcaaag acatctataa ctctctcgaa agtttgaata    9600
gtcttatctg gttcagtaat ggtaatagga aatagcctca gttctatacc ataatactgg    9660
aaatatgcct gaatttgatt accatacaac cgactgacgt tagcatctac aatcgccaag    9720
catcgtccaa aaccttgata tacatctgct agtgcagaat tctggatttc aaaaatacca    9780
tctacataca ccaaatcata ctcaatcttt tcgtaacctt ctacatgaaa agatgtttcc    9840
ttagcttcaa actttgcttg gacgatactc atgactbact santartmwc sagatctagc    9900
gctatagttg ttgacagaat ggacatacta tgatatattt tgctatagcg atggttgtaa    9960
ttggggagca ccgccacaca caagtcacag tcgacttgca ggcaattaag acaaatatta   10020
gtaatgaaat ggcgcaaaag gatgagttga ccgagttatg ggcagtcgtt aaagcgaatg   10080 gttatgggaca tggaattatc caagttgctc aggccgccaa agaagccggg gcgaccggct   10140
tttgtgttgc aatcctggat gaggccttag cgttgcgggc cgctggcttt gcggaaccca   10200
```

```
tcctagtact tggaattacg gaaccggaat acgccccact ggtagctgaa aaggatattt    10260
cactagctgt tggaacgcaa gattggctga ctacggccgc agcaattta gcggctaatc    10320 aagtgacgac accacttcac gttcatcttg cattagatac gggtatggga cgaatcgggt    10380
ttcagacgcc cgaagaattg gcaacggcgg ttacgacttt gcgtcaaccg cagtcaccat    10440
ttgactttga agggattttt acgcattttg caacggctga ccaggcagat gatacgtatt    10500
ttactcatca attaaataat tggaaacact tgattgcagt ggtggatgag ctaccacgct    10560
atgtccacgt gtccaattcg gccaccagtc tctggcatca agcttgcaat ggcaacatgg    10620
tgcgctttgg ggttgcactc tatggtctaa atccttctgg tcgcgaactc agcgcaccat    10680
accccttgca acccgcgttg tcgctaacgg cacgcttgac gtttgttaaa cgcttggctc    10740
ggggcaaatc ggtcagctat ggtgccacgt atacggccgc acaggatgaa tggattggca    10800
cggtgccgat tgggtatgcg gacggctatg aacgccgatt acaaggcttc catgtacttg    10860
ttgatggtga gttttgcgaa atcgtcggac gggtctgcat ggaccagctg atggttcgtc    10920
tgccacatga agtaccggtt ggagctaagg taactttggt tggcacggac ggtgctcgta    10980
ccatttcgtt gcaagatatt gctgactatt gtgggacaat tcattatgag attgcttgtg    11040
ggttagcacc acgagtgccg agagtttata tagattaa                           11078
```

<210> SEQ ID NO 16
<211> LENGTH: 31
<212> TYPE: DNA
<213> ORGANISM: Artificial Sequence
<220> FEATURE:
<223> OTHER INFORMATION: synthetic primer

<400> SEQUENCE: 16

```
gagatcccat atgagtatcg tccaagcaaa g                                      31
```

<210> SEQ ID NO 17
<211> LENGTH: 37
<212> TYPE: DNA
<213> ORGANISM: Artificial Sequence
<220> FEATURE:
<223> OTHER INFORMATION: synthetic primer

<400> SEQUENCE: 17

```
gtacctcgag tcatgaatta ttttccagac aatcttg                                37
```

<210> SEQ ID NO 18
<211> LENGTH: 982
<212> TYPE: DNA
<213> ORGANISM: Streptomyces glaucescens

<400> SEQUENCE: 18

```
ggtccccacc ccgcgggccg ccgcccgggc ggcgtcgacg aactccaggg cgcgcggctg     60
ctgccgttcc ccgccaactg acccgccccg cgctctcttg gagcactcgc acatgaccgt    120
ccggaagaac caggccaccc tgaccgccga cgagaagcgg cgcttcgtcg ccgccgtcct    180
ggaactcaag cgcagcggcc gctacgacga gttcgtcacc acccacaacg ccttcatcat    240
cggcgacacc gacgcgggtg agcgcaccgg ccaccgctcg ccctcgttcc tgccctggca    300
ccgcagatac ctgctggagt tcgagcgggc cctgcagagc gtggacgcct cggtcgccct    360
cccctactgg gactggtccg ccgaccgcac cgcacgggcc tcgctgtggg cgcccgactt    420
cctcggcggc accgggcgca gcctggacgg ccgggtcatg gacggaccgt tcgccgcctc    480
ggccggcaac tggccgatca acgtgcgcgt ggacgggcgc gcgtacctgc ggcggtcgct    540
```

```
cggcaccgcg gtgcgggaac tgccgacgcg ggcggaggtg gagtcggtgc tcggcatggc    600
cacgtacgac acggccccct ggaacagcgc ctcggacggc ttccgcaacc acctggaggg    660
ctggcgcggc gtcaacctgc acaaccgcgt ccacgtctgg gtgggcgggc agatggccac    720
cgggatgtcg cccaacgacc cggtgttctg gctgcacaac gcctacgtcg acaagctgtg    780
ggccgagtgg cagcgccgcc acccgggatc cggctacctc cccgccgccg gacgcccga     840 cgtggtggac ctgaacgaca ggatgaagcc ctggaacgac acctcccgg ccgaccttt      900 ggaccacacc gcccactaca ccttcgacac cgactgaccc ggccggccgt cggcaggcat    960
cctcccgcag gtcaggggta cc                                             982

<210> SEQ ID NO 19
<211> LENGTH: 24
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 19
gcannnnnnt gcnnnnnnnn nnnn                                           24

<210> SEQ ID NO 20
<211> LENGTH: 23
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (5)..(9)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 20
ggagnnnnng tnnnnnnnnn nnn                                            23

<210> SEQ ID NO 21
<211> LENGTH: 21
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (3)..(7)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 21
acnnnnnctc cnnnnnnnnn n                                              21

<210> SEQ ID NO 22
```

```
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 22 cggccg                                                                      6

<210> SEQ ID NO 23
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 23 gtatac                                                                      6

<210> SEQ ID NO 24
<211> LENGTH: 17
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(17)
<223> OTHER INFORMATION: n is a, c, g, or t

<400> SEQUENCE: 24
gaccgannnn nnnnnnn                                                         17

<210> SEQ ID NO 25
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 25 cycgrg                                                                      6

<210> SEQ ID NO 26
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 26 cycgrg                                                                      6

<210> SEQ ID NO 27
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 27 tcgcga                                                                      6

<210> SEQ ID NO 28
<211> LENGTH: 24
<212> TYPE: DNA
<213> ORGANISM: Artificial Sequence
```

```
<220> FEATURE:
<223> OTHER INFORMATION: synthesized restriction sequence
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 28
gcannnnnnt gcnnnnnnnn nnnn                                              24

<210> SEQ ID NO 29
<211> LENGTH: 11
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(8)
<223> OTHER INFORMATION: n is a, c, g, or t

<400> SEQUENCE: 29
gacnnnnngt c                                                            11

<210> SEQ ID NO 30
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 30 grcgyc                                                                   6

<210> SEQ ID NO 31
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 31 cggccg                                                                   6

<210> SEQ ID NO 32
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 32 agtact                                                                   6

<210> SEQ ID NO 33
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 33 aggcct                                                                   6
```

<210> SEQ ID NO 34
<211> LENGTH: 7
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(4)
<223> OTHER INFORMATION: n is a, c, g, or t

<400> SEQUENCE: 34 tccngga                                                                7

<210> SEQ ID NO 35
<211> LENGTH: 17
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(17)
<223> OTHER INFORMATION: n is a, c, g, or t

<400> SEQUENCE: 35
gaccgannnn nnnnnnn                                                    17

<210> SEQ ID NO 36
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 36 gtcgac                                                                 6

<210> SEQ ID NO 37
<211> LENGTH: 23
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 37
acnnnngtay cnnnnnnnnn nnn                                             23

<210> SEQ ID NO 38
<211> LENGTH: 24
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

```
<400> SEQUENCE: 38
aagnnnnnct tnnnnnnnnn nnnn                                          24

<210> SEQ ID NO 39
<211> LENGTH: 26
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (6)..(9)
<223> OTHER INFORMATION: n is a, c, g, or t
<220> FEATURE:
<221> NAME/KEY: misc_feature
<222> LOCATION: (12)..(26)
<223> OTHER INFORMATION: n is a, c, g, or t

<400> SEQUENCE: 39
grtacnnnng tnnnnnnnnn nnnnnn                                        26

<210> SEQ ID NO 40
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 40 tctaga                                                              6

<210> SEQ ID NO 41
<211> LENGTH: 15
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (8)..(15)
<223> OTHER INFORMATION: n is a, c, g, or t

<400> SEQUENCE: 41
cacctgcnnn nnnnn                                                    15

<210> SEQ ID NO 42
<211> LENGTH: 11
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(11)
<223> OTHER INFORMATION: n is a, c, g, or t

<400> SEQUENCE: 42
cgtctcnnnn n                                                        11

<210> SEQ ID NO 43
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 43
``` gatatc                                                                6

<210> SEQ ID NO 44
<211> LENGTH: 22
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(22)
<223> OTHER INFORMATION: n is a, c, g, or t

<400> SEQUENCE: 44
ctgaagnnnn nnnnnnnnnn nn                                              22

<210> SEQ ID NO 45
<211> LENGTH: 7
<212> TYPE: DNA
<213> ORGANISM: Artificial Sequence
<220> FEATURE:
<223> OTHER INFORMATION: synthesized restriction sequence

<400> SEQUENCE: 45 cctcagc                                                               7

<210> SEQ ID NO 46
<211> LENGTH: 16
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(16)
<223> OTHER INFORMATION: n is a, c, g, or t

<400> SEQUENCE: 46
gaggagnnnn nnnnnn                                                     16

<210> SEQ ID NO 47
<211> LENGTH: 11
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(11)
<223> OTHER INFORMATION: n is a, c, g, or t

<400> SEQUENCE: 47
cgtctcnnnn n                                                          11

<210> SEQ ID NO 48
<211> LENGTH: 7
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(4)
<223> OTHER INFORMATION: n is a, c, g, or t

<400> SEQUENCE: 48 cctnagg                                                               7

```
<210> SEQ ID NO 49
<211> LENGTH: 24
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 49
tgannnnnnt cannnnnnnnn nnnn                                           24

<210> SEQ ID NO 50
<211> LENGTH: 26
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (6)..(9)
<223> OTHER INFORMATION: n is a, c, g, or t
<220> FEATURE:
<221> NAME/KEY: misc_feature
<222> LOCATION: (12)..(26)
<223> OTHER INFORMATION: n is a, c, g, or t

<400> SEQUENCE: 50
grtacnnnng tnnnnnnnnn nnnnnn                                          26

<210> SEQ ID NO 51
<211> LENGTH: 23
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 51
acnnnngtay cnnnnnnnnn nnn                                             23

<210> SEQ ID NO 52
<211> LENGTH: 24
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(9)
<223> OTHER INFORMATION: n is a, c, g, or t
<220> FEATURE:
<221> NAME/KEY: misc_feature
<222> LOCATION: (13)..(24)
<223> OTHER INFORMATION: n is a, c, g, or t

<400> SEQUENCE: 52
tgannnnnnt cannnnnnnnn nnnn                                           24
```

-continued

```
<210> SEQ ID NO 53
<211> LENGTH: 7
<212> TYPE: DNA
<213> ORGANISM: Artificial Sequence
<220> FEATURE:
<223> OTHER INFORMATION: synthesized restriction sequence

<400> SEQUENCE: 53 cctcagc                                                                  7

<210> SEQ ID NO 54
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 54 gatatc                                                                   6

<210> SEQ ID NO 55
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 55 gtatac                                                                   6

<210> SEQ ID NO 56
<211> LENGTH: 15
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(12)
<223> OTHER INFORMATION: n is a, c, g, or t

<400> SEQUENCE: 56
ccannnnnnn nntgg                                                        15

<210> SEQ ID NO 57
<211> LENGTH: 7
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(4)
<223> OTHER INFORMATION: n is a, c, g, or t

<400> SEQUENCE: 57 rggnccy                                                                  7

<210> SEQ ID NO 58
<211> LENGTH: 22
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (7)..(22)
<223> OTHER INFORMATION: n is a, c, g, or t
```

```
<400> SEQUENCE: 58
ctgaagnnnn nnnnnnnnnn nn                                              22

<210> SEQ ID NO 59
<211> LENGTH: 7
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(4)
<223> OTHER INFORMATION: n is a, c, g, or t

<400> SEQUENCE: 59 tccncga                                                                7

<210> SEQ ID NO 60
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 60 tctaga                                                                 6

<210> SEQ ID NO 61
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 61 tgtaca                                                                 6

<210> SEQ ID NO 62
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 62 gagctc                                                                 6

<210> SEQ ID NO 63
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 63 grgcyc                                                                 6

<210> SEQ ID NO 64
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 64
``` gagctc                                                            6

<210> SEQ ID NO 65
<211> LENGTH: 15
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (8)..(15)
<223> OTHER INFORMATION: n is a, c, g, or t

<400> SEQUENCE: 65
cacctgcnnn nnnnn                                                 15

<210> SEQ ID NO 66
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 66 gcatgc                                                            6

<210> SEQ ID NO 67
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 67 rcatgy                                                            6

<210> SEQ ID NO 68
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 68 tgcgca                                                            6

<210> SEQ ID NO 69
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 69 cycgrg                                                            6

<210> SEQ ID NO 70
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 70 ctcgag                                                            6

```
<210> SEQ ID NO 71
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 71 cycgrg                                                                    6

<210> SEQ ID NO 72
<211> LENGTH: 24
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(8)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 72
aagnnnnnct tnnnnnnnnn nnnn                                                24

<210> SEQ ID NO 73
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 73 gkgcmc                                                                    6

<210> SEQ ID NO 74
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 74 atgcat                                                                    6

<210> SEQ ID NO 75
<211> LENGTH: 10
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(7)
<223> OTHER INFORMATION: n is a, c, g, or t

<400> SEQUENCE: 75 caynnnnrtg                                                               10

<210> SEQ ID NO 76
<211> LENGTH: 6
<212> TYPE: DNA
<213> ORGANISM: Artificial Sequence
<220> FEATURE:
<223> OTHER INFORMATION: synthesized restriction sequence
```

```
<400> SEQUENCE: 76 grgcyc                                                                    6

<210> SEQ ID NO 77
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 77 yccggr                                                                    6

<210> SEQ ID NO 78
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 78 aggcct                                                                    6

<210> SEQ ID NO 79
<211> LENGTH: 8
<212> TYPE: DNA
<213> ORGANISM: Artificial Sequence
<220> FEATURE:
<223> OTHER INFORMATION: synthesized restriction sequence

<400> SEQUENCE: 79 ttaattaa                                                                  8

<210> SEQ ID NO 80
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 80 gkgcmc                                                                    6

<210> SEQ ID NO 81
<211> LENGTH: 12
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (5)..(9)
<223> OTHER INFORMATION: n is a, c, g, or t

<400> SEQUENCE: 81
rgcannnnnt gc                                                            12

<210> SEQ ID NO 82
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 82 rcatgy                                                                    6
```

<210> SEQ ID NO 83
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 83 atgcat                                                                    6

<210> SEQ ID NO 84
<211> LENGTH: 10
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(7)
<223> OTHER INFORMATION: n is a, c, g, or t

<400> SEQUENCE: 84 caynnnnrtg                                                               10

<210> SEQ ID NO 85
<211> LENGTH: 10
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (6)..(10)
<223> OTHER INFORMATION: n is a, c, g, or t

<400> SEQUENCE: 85 ggatcnnnnn                                                               10

<210> SEQ ID NO 86
<211> LENGTH: 7
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (4)..(4)
<223> OTHER INFORMATION: n is a, c, g, or t

<400> SEQUENCE: 86 ggtnacc                                                                   7

<210> SEQ ID NO 87
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 87 gttaac                                                                    6

<210> SEQ ID NO 88
<211> LENGTH: 6
<212> TYPE: DNA
<213> ORGANISM: Artificial Sequence
<220> FEATURE:

-continued

```
<223> OTHER INFORMATION: synthesized restriction sequence

<400> SEQUENCE: 88 ccatgg                                                              6

<210> SEQ ID NO 89
<211> LENGTH: 11
<212> TYPE: DNA
<213> ORGANISM: Artificial Sequence
<220> FEATURE:
<223> OTHER INFORMATION: synthesized restriction sequence
<220> FEATURE:
<221> NAME/KEY: misc_feature
<222> LOCATION: (8)..(11)
<223> OTHER INFORMATION: n is a, c, g, or t

<400> SEQUENCE: 89
gctcttcnnn n                                                       11

<210> SEQ ID NO 90
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 90 yccggr                                                              6

<210> SEQ ID NO 91
<211> LENGTH: 6
<212> TYPE: DNA
<213> ORGANISM: Artificial Sequence
<220> FEATURE:
<223> OTHER INFORMATION: synthesized restriction sequence

<400> SEQUENCE: 91 ccatgg                                                              6
```